(12) United States Patent
Higuchi et al.

(10) Patent No.: US 10,118,995 B2
(45) Date of Patent: Nov. 6, 2018

(54) ORGANIC/HETEROMETALLIC HYBRID POLYMER, PROCESS FOR PRODUCING SAME, FILM OF ORGANIC/HETEROMETALLIC HYBRID POLYMER, ORGANIC/MULTIMETALLIC HYBRID POLYMER, PROCESS FOR PRODUCING SAME, AND FILM OF ORGANIC/MULTIMETALLIC HYBRID POLYMER

(71) Applicant: National Institute for Materials Science, Ibaraki (JP)

(72) Inventors: Masayoshi Higuchi, Ibaraki (JP); Takashi Sato, Ibaraki (JP)

(73) Assignee: National Institute of Materials Science, Ibaraki (JP)

( * ) Notice: Subject to any disclaimer, the term of this patent is extended or adjusted under 35 U.S.C. 154(b) by 165 days.

(21) Appl. No.: 15/307,037

(22) PCT Filed: May 1, 2015

(86) PCT No.: PCT/JP2015/063084
§ 371 (c)(1),
(2) Date: Oct. 27, 2016

(87) PCT Pub. No.: WO2015/167010
PCT Pub. Date: Nov. 5, 2015

(65) Prior Publication Data
US 2017/0044325 A1    Feb. 16, 2017

(30) Foreign Application Priority Data

May 2, 2014    (JP) .................................. 2014-095275
Jan. 26, 2015  (JP) .................................. 2015-012448

(51) Int. Cl.
*C08G 79/14*    (2006.01)
*C08J 5/18*     (2006.01)
(Continued)

(52) U.S. Cl.
CPC ........... *C08G 79/14* (2013.01); *C07D 213/22* (2013.01); *C07D 401/14* (2013.01); *C08G 73/00* (2013.01);
(Continued)

(58) Field of Classification Search
CPC .... C08G 79/14; C07D 213/22; C07D 401/14; C08J 2385/00
See application file for complete search history.

(56) References Cited

U.S. PATENT DOCUMENTS

2009/0270589 A1   10/2009  Higuchi et al.
2012/0307341 A1*  12/2012  Higuchi .............. C07D 213/22
                                                     359/275
(Continued)

FOREIGN PATENT DOCUMENTS

EP    2444839 A1    4/2012
EP    2796488 A1   10/2014
(Continued)

OTHER PUBLICATIONS

Rehahn, M. "Organic/inorganic hybrid polymers." Acta polymerica 49.5 (1998): 201-224.*
(Continued)

Primary Examiner — Nicholas E Hill
(74) Attorney, Agent, or Firm — Hoffmann & Baron, LLP

(57) ABSTRACT

The present invention relates to an organic/heterometallic hybrid polymer including a plurality of organometal complexes and a plurality of transition metals, the organic/heterometallic hybrid polymer, wherein
(Continued)

the plurality of organometal complexes are linked in a linear manner by sandwiching each of the plurality of transition metals therebetween, the organometal complexes include two ligands each having a terpyridyl group and one connector having Ru(dppe)$_2$ and two ethynylene groups, and the two ligands are linked by the connector, so that a nitrogen atom at position 1' of the terpyridyl group is directed toward the terminal side of the molecule of the organometal complex, and the terpyridyl groups of at least two different organometal complexes of the plurality of organometal complexes are bound to one of the transition metals through a coordinate bond, thereby linking the plurality of organometal complexes while sandwiching the plurality of transition metals alternately therebetween.

25 Claims, 34 Drawing Sheets

(51) Int. Cl.
| | | |
|---|---|---|
| | *C07D 401/14* | (2006.01) |
| | *C07D 213/22* | (2006.01) |
| | *C08G 79/00* | (2006.01) |
| | *C08G 73/00* | (2006.01) |
| | *G01N 27/04* | (2006.01) |
| | *G02F 1/15* | (2006.01) |
| | *H01B 1/06* | (2006.01) |
| | *H01M 8/02* | (2016.01) |

(52) U.S. Cl.
CPC ............... *C08G 79/00* (2013.01); *C08J 5/18* (2013.01); *G01N 27/04* (2013.01); *G02F 1/15* (2013.01); *H01B 1/06* (2013.01); *H01M 8/02* (2013.01); *C08J 2385/00* (2013.01)

(56) References Cited

U.S. PATENT DOCUMENTS

2014/0009812 A1* 1/2014 Higuchi ............... C07D 213/22
　　　　　　　　　　　　　　　　　　　　　　　　　　　359/270
2015/0021180 A1* 1/2015 Higuchi ............... H01B 1/128
　　　　　　　　　　　　　　　　　　　　　　　　　　　204/415

FOREIGN PATENT DOCUMENTS

| JP | 2009-265437 A | 11/2009 |
|---|---|---|
| JP | 2012-188517 A | 10/2012 |
| WO | WO2014021208 A1 | 2/2014 |

OTHER PUBLICATIONS

Stefopoulos, Andreas A., et al. "Carbon nanotubes decorated with terpyridine-ruthenium complexes." Journal of Polymer Science Part A: Polymer Chemistry 47.10 (2009): 2551-2559.*

Breul, Alexander M., et al. "Synthesis and Characterization of Poly (methyl methacrylate) Backbone Polymers Containing Side-Chain Pendant Ruthenium (II) Bis-Terpyridine Complexes With an Elongated Conjugated System." Macromolecular Chemistry and Physics 213.8 (2012): 808-819.*

Barthelmes, Kevin, et al. "New Ruthenium Bis (terpyridine) Methanofullerene and Pyrrolidinofullerene Complexes: Synthesis and Electrochemical and Photophysical Properties." Inorganic chemistry 54.7 (2015): 3159-3171.*

Office Action from corresponding Japanese Application No. 2016-516422, pp. 1-4 (dated Apr. 18, 2017).

Supplementary European Search Report for corresponding Application No. EP15786456.2, pp. 1-4, dated Aug. 25, 2017.

M. Higuchi, "Electrochromic Organic-Metallic Hybrid Polymers: Fundamentals and Device Applications", Polymer Journal, vol. 41, No. 7, pp. 511-520 (2009).

Sato et al., "An Alternatively Introduced Heterometallo-Supramolecular Polymer: Synthesis and Solid-State Emission Switching by Electrochemical Redox", Chem. Commun., 49, 5256-5258 (2013).

International Search Report for corresponding PCT Application No. PCT/JP2015/063084, pp. 1-4, (dated Jun. 30, 2015).

* cited by examiner

ORGANIC/HETEROMETALLIC HYBRID POLYMER, PROCESS FOR PRODUCING SAME, FILM OF ORGANIC/HETEROMETALLIC HYBRID POLYMER, ORGANIC/MULTIMETALLIC HYBRID POLYMER, PROCESS FOR PRODUCING SAME, AND FILM OF ORGANIC/MULTIMETALLIC HYBRID POLYMER

CROSS-REFERENCE TO RELATED APPLICATIONS

This application is a U.S. National Phase Application of International Application No. PCT/JP2015/063084 filed on May 1, 2015 and asserts priority to Japanese Patent Application No. 2014-095275 filed on May 2, 2014 and Japanese Patent Application No. 2015-012448 filed on Jan. 26, 2015, all of which are hereby incorporated by reference in their entirety.

TECHNICAL FIELD

The present invention relates to an organic/heterometallic hybrid polymer, a method for producing the same, an organic/heterometallic hybrid polymer film, an organic/multimetallic hybrid polymer, a method for producing the same and an organic/multimetallic hybrid polymer film.

Priority is claimed on Japanese Patent Application No. 2014-095275, filed May 2, 2014, and Japanese Patent Application No. 2015-012448, filed Jan. 26, 2015, the contents of which are incorporated herein by reference.

BACKGROUND ART

Organic/metallic hybrid polymers are supramolecular polymers in which metals are arranged precisely in a polymer main chain structure, and are known to exhibit electrical and optical functions by the electronic interaction between the organic ligand and the metal, or by the electronic interaction between adjacent metals.

For example, organic/metallic hybrid polymers containing a transition metal such as iron (Fe) or ruthenium (Ru) exhibit electrochromic properties in the visible region, and have been studied as display device materials (Non-Patent Document 1). It should be noted that the electrochromic property refers to a property to change its color by applying a charge to the material.

Further, organic/heterometallic hybrid polymers into which europium (Eu) and Fe are precisely introduced alternately using asymmetric organic ligands have been reported to function as display devices of the luminescence switching of Eu corresponding to the electrochromic properties by the oxidation-reduction of Fe (Non-Patent Document 2).

In addition, several organic/metallic hybrid polymers having electrochromic properties have been synthesized (Patent Documents 1 and 2).

Although the research and development of electrochromic materials in the visible light region have advanced as described above, the research and development of electrochromic materials in the ultraviolet region or infrared region have not advanced much. In particular, if the electrochromic materials in the infrared region can be developed, they can be applied to a near infrared light-shielding electrochromic window which can freely shield near infrared light of sunlight entering inside the room, thereby enhancing the cooling effect of the room and saving energy. Further, with respect to near infrared light used in optical communications, development of products in the form of an optical device for a near infrared optical shutter may also be possible.

Accordingly, the inventors of the present invention have newly synthesized an organic/heterometallic hybrid polymer in which hetero metals are closely arranged within the polymer via a π-conjugated organic portion, aimed at electrochromism in the near infrared region using the electronic interaction between the metals. The organic/heterometallic hybrid polymer exhibited an intervalence charge transfer (IVCT) absorption between hetero metals (zinc (Zn)—Ru) in the near infrared region by the application of a voltage. Since the absorbance of the absorption changes in a reversible manner by the ON/OFF of the voltage application, the potential as an optical device material was shown.

However, since the energy of IVCT occurring between hetero metals is relatively large, the absorption wavelength is limited to the near infrared region from 900 nm to 1,500 nm. Therefore, it is difficult to realize electrochromism in the infrared region with a wavelength longer than 1,500 nm.

Further, because the electrochromism itself is a simple ON/OFF of the absorption, switching of a plurality of absorption wavelengths required in the optical device of the near infrared optical shutter is difficult.

Furthermore, with respect to the above linear organic/heterometallic hybrid polymers, when the ON/OFF of the voltage application is repeated, the polymer film is gradually dissolved. In other words, durability of the polymer film to the repetitive electrochromic changes is not sufficient.

CITATION LIST

Patent Documents

[Patent Document 1] Japanese Unexamined Patent Application, First Publication No. 2012-188517
[Patent Document 2] Japanese Unexamined Patent Application, First Publication No. 2009-265437

Non-Patent Documents

[Non-Patent Document 1] Higuchi M. Polym. J. 2009, 41, 511-520.
[Non-Patent Document 2] Sato T; Higuchi M. Chem. Commun. 2013, 49, 5256-5258.

SUMMARY OF INVENTION

Technical Problem

An object of the present invention is to provide a linear and stable organic/heterometallic hybrid polymer having electrochromic properties (in particular, electrochromic properties in the near infrared region), a method for producing the same, and an organic/heterometallic hybrid polymer film.

Further, the present invention also has an object of providing an organic/multimetallic hybrid polymer exhibiting electrochromism in the infrared region with a wavelength equal to or longer than 1,500 nm, which has a light blocking function by switching ON/OFF at least two wavelengths within a range from the near infrared region to the infrared region, and forms a film exhibiting high durability against repetitive electrochromic changes, a method for producing the same and an organic/multimetallic hybrid polymer film.

Solution to Problem

In one aspect of the present invention, the inventors of the present invention have synthesized a novel organic/heterometallic hybrid polymer and a film thereof by trial and error in view of the above circumstances. In particular, materials in which hetero metals are closely arranged within a conductive polymer can be converted to a structure that exhibits an intervalence charge transfer (IVCT) between hetero metals by the application of a voltage, and can freely convert the optical absorption spectrum from the visible light region to the near infrared light region. In addition, the present inventors have completed the present invention by discovering that the above organic/heterometallic hybrid polymer can be used as a near infrared light-blocking electrochromic window or a near infrared optical shutter.

In view of the above circumstances, by trial and error, the inventors of the present invention have synthesized an organometal ligand having two transition metals, and by causing it to form a complex with another metal, synthesized a linear organic/multimetallic hybrid polymer. The organic/multimetallic hybrid polymer refers to a supramolecular polymer in which an organic compound and two or more different kinds of metals or a metal having two or more different coordination states are linked. In addition, one aspect of the organic/multimetallic hybrid polymer is a supramolecular polymer in which a plurality of organic compounds containing at least two ligands and at least one metal in a molecule are linked by forming a complex with a transition metal outside the aforementioned organic compound. Further, in another aspect of the organic/multimetallic hybrid polymer, at least two metals in the aforementioned organic compound are included. The organic/heterometallic hybrid polymer refers to a supramolecular polymer in which the aforementioned metal and the transition metal outside the organic compound are different.

Furthermore, in yet another aspect of the present invention, the present inventors have formed a film of the organic/multimetallic hybrid polymer on a glass substrate and an ITO substrate. The film of the organic/multimetallic hybrid polymer containing Zn and two Ru in the unit structure exhibited not only an IVCT absorption between hetero metals (Zn—Ru) but also an IVCT absorption between the same metal (Ru—Ru) within the near infrared to infrared regions by changing the applied voltage. That is, from an initial state having no absorption within the near infrared to infrared regions, by applying an oxidation potential, an IVCT absorption between the same metal (Ru—Ru) was exhibited. Furthermore, when an even higher oxidation potential was applied, the IVCT absorption between the same metal (Ru—Ru) disappeared, and the IVCT absorption between hetero metals (Zn—Ru) appeared. As a result, it was found that by changing the applied voltage, a state having no absorption within the near infrared to infrared regions can be electrochemically switched in a reversible manner to a state in which absorptions at two different wavelengths are exhibited.

Furthermore, in yet another aspect of the present invention, a branched organic/multimetallic hybrid polymer having a three-dimensional network structure was synthesized by introducing a branched portion into the polymer using a branched-type organic ligand that can be linked in three directions, when causing the organometal ligand having two organometals to form a complex with another metal. In addition, these were deposited on a glass substrate and an ITO substrate.

Films of these organic/multimetallic hybrid polymers stably exhibited reversible electrochromic changes for at least 50 repetitions of ON/OFF of the voltage application. Further, when the mixing ratio of the branched-type organic ligand that can be linked in three directions was increased, compared to the IVCT absorption by the film of the linear organic/multimetallic hybrid polymer having no branched portion, the absorption intensity increased, and it was possible to increase the absorbance difference (contrast) in the electrochromism.

As described above, the inventors of the present invention have synthesized a novel organometal ligand and used it to synthesize a novel organic/multimetallic hybrid polymer. The present inventors have completed the present invention by discovering that the film of the organic/multimetallic hybrid polymer exhibits electrochromic properties in the infrared region, has a light blocking function by switching ON/OFF at two wavelengths within the near infrared to infrared region, and stably exhibits reversible electrochromic changes even when ON/OFF of the voltage application is repeated if the branched portion is introduced to the polymer by using a branched organic ligand.

For example, the present invention includes the following configurations.

[1] An organic/heterometallic hybrid polymer including a plurality of organometal complexes and a plurality of transition metals, wherein the aforementioned plurality of organometal complexes are linked in a linear manner by sandwiching each of the aforementioned plurality of transition metals therebetween, the aforementioned organometal complexes include two ligands each having a terpyridyl group and one connector having $Ru(dppe)_2$ and two ethynylene groups, and the two ligands are linked by the connector, so that a nitrogen atom at position 1' of the aforementioned terpyridyl group is directed toward the terminal side of the molecule of the aforementioned organometal complex, and the terpyridyl groups of at least two different organometal complexes of the aforementioned plurality of organometal complexes are bound to one of the aforementioned transition metals through a coordinate bond, thereby linking the aforementioned plurality of organometal complexes while sandwiching the aforementioned plurality of transition metals alternately therebetween.

[2] The organic/heterometallic hybrid polymer according to [1], wherein the aforementioned transition metal is any one of Ru, Fe or Zn.

[3] The organic/heterometallic hybrid polymer according to [1] or [2], wherein a molecular weight $M_W$ is at least $10.5 \times 10^4$ and not more than $29.2 \times 10^4$.

[4] A method of producing an organic/heterometallic hybrid polymer, the method including a step of synthesizing an organometal complex having $Ru(dppe)_2$ and a terminal terpyridyl group by reacting a terpyridine compound having an ethynyl group and a terpyridyl group with a compound containing $Ru(dppe)_2$ in an organic solvent, and a step of synthesizing the organic/heterometallic hybrid polymer by reacting the aforementioned organometal complex and a transition metal compound in an organic solvent.

[5] The method of producing an organic/heterometallic hybrid polymer according to [4], wherein 1.0 molar equivalent or more of the transition metal compound is reacted with respect to the aforementioned organometal complex.

[6] The method of producing an organic/heterometallic hybrid polymer according to [4] or [5], wherein the aforementioned transition metal compound is any one of $RuCl_2$, $Fe(BF_4)_2$, or $Zn(NTf_2)_2$.

[7] The method of producing an organic/heterometallic hybrid polymer according to any one of [4] to [6], wherein a reaction time of the aforementioned organometal complex and the aforementioned transition metal compound is equal to or more than 12 hours.

[8] An organic/heterometallic hybrid polymer film including the organic/heterometallic hybrid polymer according to any one of [1] to [3].

[9] The organic/heterometallic hybrid polymer film according to [8], wherein a film thickness is at least 100 nm and not more than 1 mm.

[10] The organic/heterometallic hybrid polymer film according to [8] or [9], wherein a transition metal contained in the aforementioned organic/heterometallic hybrid polymer is a transition metal of any one of Fe or Zn.

[11] An organic/multimetallic hybrid polymer including a plurality of organometal ligands and a plurality of transition metals, wherein
a linear portion in which the aforementioned plurality of organometal ligands are linked in a linear manner by sandwiching each of the aforementioned plurality of transition metals therebetween is included,
the aforementioned organometal ligand is formed by linking two ligands to one connector,
the aforementioned connector is formed with a benzene ring at the center by linking two $Ru(dppe)_2$ via two ethynylene groups bonded to the benzene ring, while connecting two phenyl groups to the aforementioned two $Ru(dppe)_2$ via other two ethynylene groups,
the aforementioned ligands are terpyridyl groups and are formed by being connected respectively to the aforementioned two phenyl groups of the aforementioned connector, and
the aforementioned terpyridyl groups of at least two different organometal ligands of the aforementioned plurality of organometal ligands are bound to one of the aforementioned transition metals through a coordinate bond, thereby linking the aforementioned plurality of organometal ligands while alternately sandwiching the aforementioned plurality of transition metals therebetween.

[12] The organic/multimetallic hybrid polymer according to [11], wherein the aforementioned transition metal is Fe, Zn, Co or Ru.

[13] The organic/multimetallic hybrid polymer according to [11] or [12] which is linear

[14] The organic/multimetallic hybrid polymer according to [11] or [12] which is branched.

[15] The organic/multimetallic hybrid polymer according to [14], including a branched portion composed of 1,3,5-Tris[4-(2,2':6',2"-terpyridin-4'-yl)phenyl]benzene.

[16] The organic/multimetallic hybrid polymer according to [14] or [15], wherein a content of the aforementioned branched portion is at least 10 molar parts and not more than 30 molar parts, relative to the total number of moles of linear portions and branched portions constituting the organic/multimetallic hybrid polymer.

[17] A method of synthesizing an organic/multimetallic hybrid polymer, the method including
a step of synthesizing a binuclear organometallic site containing two $Ru(dppe)_2$ by reacting 1 molar equivalent of diethynylbenzene and 2 molar equivalents of $Ru(dppe)_2Cl$ (OTf) in an organic solvent,
a step of synthesizing an organometal ligand having a terpyridyl group at the terminal and two $Ru(dppe)_2$ by reacting 2 molar equivalents of a terpyridine compound having an ethynyl group and a terpyridyl group with one molar equivalent of a binuclear organometallic site in an organic solvent, and
a step of synthesizing a linear organic/multimetallic hybrid polymer by reacting the aforementioned organometal ligand and a transition metal compound in an organic solvent.

[18] The method of synthesizing an organic/multimetallic hybrid polymer according to [17], wherein a branched organic/multimetallic hybrid polymer is synthesized by reacting the aforementioned linear organic/multimetallic hybrid polymer, a branched compound branched into three or more directions with a branch element at the center and having a ligand at a branched molecule end, and a transition metal compound.

[19] The method of synthesizing an organic/multimetallic hybrid polymer according to [18], wherein the aforementioned branched compound is 1,3,5-Tris[4-(2,2':6',2"-terpyridin-4'-yl)phenyl]benzene.

[20] The method of synthesizing an organic/multimetallic hybrid polymer according to [18] or [19], wherein a mixing amount of the aforementioned branched compound is at least 10 molar parts and not more than 30 molar parts, relative to the combined total of 100 molar parts of linear portions constituting the linear organic/multimetallic hybrid polymer.

[21] The method of synthesizing an organic/multimetallic hybrid polymer according to [17], wherein 1.0 molar equivalent or more of the transition metal compound is reacted with respect to the aforementioned organometal ligand.

[22] The method of synthesizing an organic/multimetallic hybrid polymer according to any one of [17] to [21], wherein the aforementioned transition metal compound is $Fe(BF_4)_2$ or $Zn(NTf_2)_2$.

[23] The method of synthesizing an organic/multimetallic hybrid polymer according to any one of [17] to [22], wherein a reaction time of the aforementioned organometal ligand and the aforementioned transition metal compound is equal to or more than 6 hours.

[24] An organic/multimetallic hybrid polymer film, including the organic/multimetallic hybrid polymer according to any one of [11] to [16].

[25] The organic/multimetallic hybrid polymer film according to [24], wherein a film thickness is at least 100 nm and not more than 1 mm.

In addition, the present invention includes the following aspects.

(1) An organic/heterometallic hybrid polymer which is a polymer obtained by linking a plurality of organometal complexes in a linear manner while sandwiching a transition metal therebetween, wherein the aforementioned organometal complex is formed in such a manner that two ligands having a terpyridine group are linked by a connector having Ru—$[PPh_2]_4$ and acetylene so as to direct the aforementioned terpyridine group toward the outside, and terpyridine groups of different organometal complexes are connected by being bound to one transition metal through a coordinate bond.

(2) The organic/heterometallic hybrid polymer according to (1), wherein the aforementioned transition metal is any one of Ru, Fe or Zn.

(3) The organic/heterometallic hybrid polymer according to (1) or (2), wherein a molecular weight $M_W$ is at least $10.5 \times 10^4$ and not more than $29.2 \times 10^4$.

(4) A method of producing an organic/heterometallic hybrid polymer, the method including:

a step of synthesizing an organometal complex having a terminal terpyridine group by mixing and stirring a terpyridine having an ethynyl group with a Ru complex in an organic solvent, and a step of synthesizing the organic/heterometallic hybrid polymer by mixing and stirring the aforementioned organometal complex and a transition metal compound in an organic solvent.

(5) The method of producing an organic/heterometallic hybrid polymer according to (4), wherein 1.0 equivalent or more of the transition metal compound is used with respect to the aforementioned organometal complex.

(6) The method of producing an organic/heterometallic hybrid polymer according to (4) or (5), wherein the aforementioned transition metal compound is any one of $RuCl_2$, $Fe(BF_4)_2$, or $Zn(NTf_2)_2$.

(7) The method of producing an organic/heterometallic hybrid polymer according to any one of (4) to (6), wherein a mixing and stirring time of the organometal complex and the transition metal compound is equal to or more than 12 hours.

(8) An organic/heterometallic hybrid polymer film, including the organic/heterometallic hybrid polymer according to any one of (1) to (3).

(9) The organic/heterometallic hybrid polymer film according to (8), wherein a film thickness is at least 100 nm and not more than 1 mm.

(10) The organic/heterometallic hybrid polymer film according to (8) or (9), wherein a transition metal contained in the aforementioned organic/heterometallic hybrid polymer is Fe or Zn.

(11) An organic/multimetallic hybrid polymer, wherein a linear portion in which organometal ligands are linked in a linear manner by sandwiching transition metals therebetween is included, the aforementioned organometal ligands are formed by linking ligands to a connector, the aforementioned connector is formed with a benzene ring at the center and linking two $Ru[1,2$-bis (diphenylphosphino)ethane$]_2$ (hereinafter, abbreviated as $Ru(dppe)_2$) via acetylene, while connecting phenyl groups to each of $Ru(dppe)_2$ via acetylene, respectively, the aforementioned ligands are terpyridine groups and are formed by being connected to the phenyl groups of the aforementioned connector, and the aforementioned terpyridine groups are linked to a transition metal through a coordinate bond.

(12) The organic/multimetallic hybrid polymer according to (11), wherein the aforementioned transition metal is Fe, Zn, Co or Ru.

(13) The organic/multimetallic hybrid polymer according to (11) or (12), having a linear structure.

(14) The organic/multimetallic hybrid polymer according to (11) or (12), having a branched structure.

(15) The organic/multimetallic hybrid polymer according to (14), including a branched portion composed of 1,3,5-Tris[4-(2,2':6',2''-terpyridin-4'-yl)phenyl]benzene.

(16) The organic/multimetallic hybrid polymer according to (14) or (15), wherein a content of the aforementioned branched portion is at least 10 molar parts and not more than 30 molar parts.

(17) A method of synthesizing an organic/multimetallic hybrid polymer, the method including a step of synthesizing a binuclear organometallic site containing two $Ru(dppe)_2$ by mixing and stirring 1 equivalent of diethynylbenzene and 2 equivalents of $Ru(dppe)_2Cl$ (OTf) in an organic solvent, a step of synthesizing an organometal ligand having a terpyridine group at the terminal and two $Ru(dppe)_2$ by mixing and stirring 2 equivalents of terpyridine having an ethynyl group and one equivalent of a binuclear organometallic site in an organic solvent, and a step of synthesizing a linear organic/multimetallic hybrid polymer by mixing and stirring the aforementioned organometal ligand and a transition metal compound in an organic solvent.

(18) The method of synthesizing an organic/multimetallic hybrid polymer according to (17), including synthesizing a branched organic/multimetallic hybrid polymer by mixing and stirring of the aforementioned linear organic/multimetallic hybrid polymer together with a branched compound branched into three or more directions and having a ligand at the branched end, and a transition metal compound.

(19) The method of synthesizing an organic/multimetallic hybrid polymer according to (18), wherein the aforementioned branched compound is 1,3,5-Tris[4-(2,2':6',2''-terpyridin-4'-yl)phenyl]benzene.

(20) The method of synthesizing an organic/multimetallic hybrid polymer according to (18) or (19), wherein a mixing amount of the aforementioned branched compound is at least 10 molar parts and not more than 30 molar parts, relative to the linear organic/multimetallic hybrid polymer.

(21) The method of synthesizing an organic/multimetallic hybrid polymer according to (17), wherein 1.0 equivalent or more transition metal compound is used with respect to the aforementioned organometal ligand.

(22) The method of synthesizing an organic/multimetallic hybrid polymer according to any one of (17) to (21), wherein the aforementioned transition metal compound is $Fe(BF_4)_2$ or $Zn(NTf_2)_2$.

(23) The method of synthesizing an organic/multimetallic hybrid polymer according to any one of (17) to (22), wherein a mixing and stirring time of the organometal ligand and the transition metal compound is equal to or more than 6 hours.

(24) An organic/multimetallic hybrid polymer film, including the organic/multimetallic hybrid polymer according to any one of (11) to (16).

(25) The organic/multimetallic hybrid polymer film according to (24), wherein a film thickness is at least 100 nm and not more than 1 mm.

Advantageous Effects of Invention

The organic/heterometallic hybrid polymer of the present invention is composed of a plurality of organometal complexes and a plurality of transition metals. In the organic/heterometallic hybrid polymer of the present invention, the plurality of organic metal complexes are linked linearly by sandwiching each transition metal of the plurality of transition metals therebetween. The aforementioned organometal complexes include two ligands each having a terpyridyl group and one connector having $Ru(dppe)_2$ and two ethynylene groups, and are formed by linking the two ligands by the connector, so that a nitrogen atom at position 1' of the aforementioned terpyridyl group is directed toward the terminal side of the molecule of the organometal complex. The terpyridyl groups of at least two different organometal complexes of the plurality of organometal complexes are bound to one transition metal through a coordinate bond, thereby linking the plurality of organometal complexes while alternately and respectively sandwiching the plurality of transition metals therebetween. Therefore, it is possible to prepare a linear supramolecular polymer that links the organometal complexes and the transition metals alternately and is capable of causing an electrochromic reaction.

The method of producing an organic/heterometallic hybrid polymer according to the present invention is configured to include a step of synthesizing an organometal complex having a terpyridyl group at the terminal by reacting a terpyridine compound having an ethynyl group and a terpyridyl group with a compound containing Ru(dppe)$_2$ in an organic solvent, and a step of synthesizing the organic/heterometallic hybrid polymer by reacting the aforementioned organometal complex and a transition metal compound in an organic solvent. Therefore, it is possible to synthesize a linear supramolecular polymer with high yield that links the organometal complexes and the transition metals alternately and is capable of causing an electrochromic reaction.

The organic/heterometallic hybrid polymer film according to the present invention is configured to include the organic/heterometallic hybrid polymer described earlier. Therefore, it can be made into a film capable of causing an electrochromic reaction and can be applied to an optical device. In particular, if it is configured so that a transition metal contained in the aforementioned organic/heterometallic hybrid polymer is Fe or Zn, it can be made into a film capable of causing an electrochromic reaction in the near infrared light region and can be applied to an optical device.

The organic/multimetallic hybrid polymer of the present invention includes a plurality of organometal ligands and a plurality of transition metals. The organic/multimetallic hybrid polymer of the present invention has a linear portion in which the plurality of organometal ligands are linked in a linear manner by sandwiching each transition metal of the plurality of transition metals therebetween, and the aforementioned organometal ligands are formed by linking two ligands to one connector. The aforementioned connector is formed with a benzene ring at the center by linking two Ru[1,2-bis(diphenylphosphino)ethane]$_2$ (sometimes abbreviated as Ru(dppe)$_2$ in the present description) via two ethynylene groups bonded to the benzene ring, while connecting two phenyl groups to the aforementioned two Ru(dppe)$_2$ via other ethynylene groups. The aforementioned ligands are terpyridyl groups and are connected respectively to the phenyl groups of the aforementioned connector. It is configured so that the aforementioned terpyridyl groups of at least two different organometal ligands of the plurality of organometal ligands are bound to one of the aforementioned transition metals through a coordinate bond, thereby linking the plurality of organometal ligands by alternately sandwiching the plurality of transition metals therebetween. For this reason, it is possible to provide electrochromic properties in the infrared light region and increase the repetition stability.

The method of synthesizing an organic/multimetallic hybrid polymer according to the present invention is configured to include a step of synthesizing a binuclear organometallic site containing two Ru(dppe)$_2$ by reacting 1 equivalent of diethynylbenzene and 2 equivalents of Ru(dppe)$_2$Cl(OTf) in an organic solvent, a step of synthesizing an organometal ligand having a terpyridyl group at the terminal and two Ru(dppe)$_2$ by reacting 2 equivalents of a terpyridine compound having an ethynyl group and a terpyridyl group with 1 equivalent of a binuclear organometallic site in an organic solvent, and a step of synthesizing a linear organic/multimetallic hybrid polymer by reacting the aforementioned organometal ligand and a transition metal compound in an organic solvent. For this reason, it is possible to synthesize an organic/multimetallic hybrid polymer exhibiting electrochromic properties in the infrared light region and high repetition stability with high yield.

Since the organic/multimetallic hybrid polymer film of the present invention is configured to include the organic/multimetallic hybrid polymer described earlier, it is possible to form a film exhibiting electrochromic properties in the infrared light region and high repetition stability. As a result, it can be applied to an optical device capable of light blocking by switching ON/OFF at two wavelengths within the near infrared to infrared region.

DESCRIPTION OF EMBODIMENTS (Organic/Heterometallic Hybrid Polymer)

First, an organic/heterometallic hybrid polymer according to a first embodiment of the present invention will be described.

Figure 1:
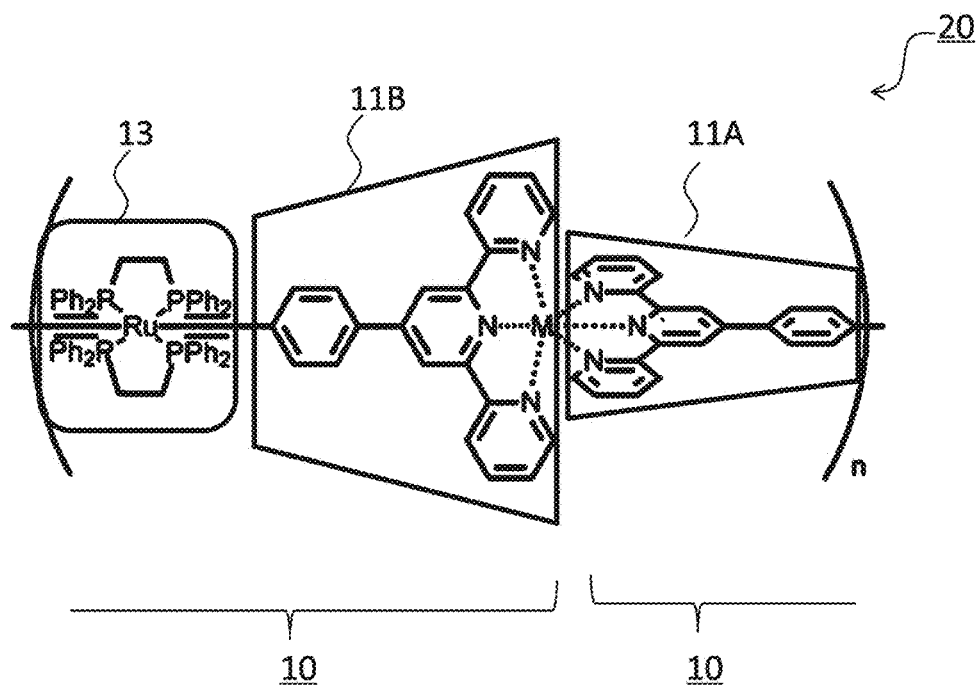
FIG. 1 is a diagram showing an example of an organic/heterometallic hybrid polymer according to an embodiment of the present invention.

FIG. 1 is a diagram showing an example of a structural formula of the organic/heterometallic hybrid polymer according to the first embodiment of the present invention. In FIG. 1, n is an integer of 2 or more.

As shown in FIG. 1, an organic/heterometallic hybrid polymer 20 according to the first embodiment of the present invention is a supramolecular polymer having a plurality of organometal complexes 10 are linked in a linear manner while sandwiching a transition metal M therebetween. The terpyridyl groups of at least two different organometal complexes of the plurality of organometal complexes 10 are bound to one transition metal M through a coordinate bond, thereby linking the plurality of organic metal complexes via the transition metal M. As shown in FIG. 1, the organic/ heterometallic hybrid polymer 20 has a unit structure containing the organic metal complex 10 and the transition metal M (a structure enclosed in parentheses).

The transition metal M is any one of Ru, Fe or Zn. As a result, it is possible to efficiently link the organometal complexes 10 and to form the organic/heterometallic hybrid polymer 20 which is linear.

A molecular weight $M_W$ of the organic/heterometallic hybrid polymer 20 is preferably at least $10.5 \times 10^4$ and not more than $29.2 \times 10^4$. As a result, it is possible to form a stable film. Here, the molecular weight of the supramolecular polymer refers to the average molecular weight per one polymer chain. The molecular weight can be measured by a SEC-RALLS-Viscometry method.

Figure 2:
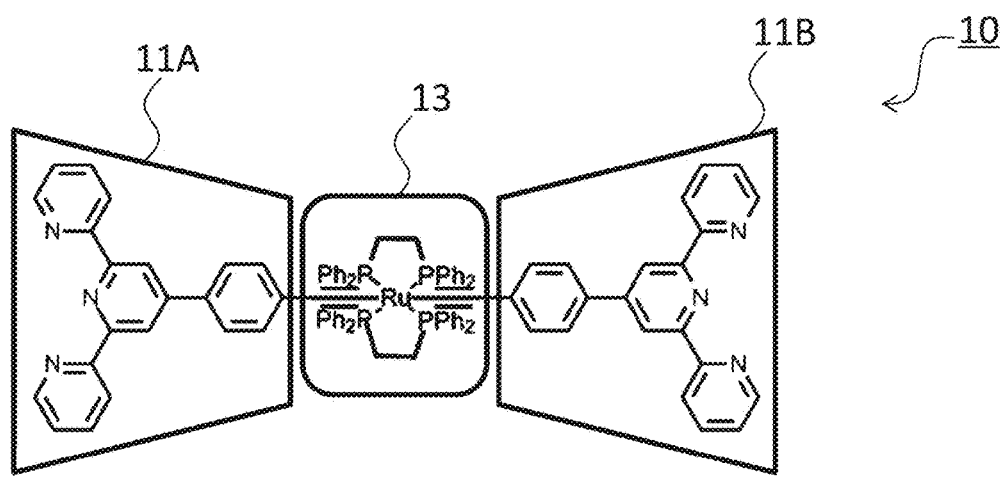
FIG. 2 is a diagram showing an example of an organometal complex.

FIG. 2 is a diagram showing an example of an organometal complex.

As shown in FIG. 2, in the organometal complex 10, two ligands 11A and 11B having a terpyridyl group are linked by a single connector 13 having $Ru(dppe)_2$ and an ethynylene group, so that a nitrogen atom at position 1' of the aforementioned terpyridyl group is directed toward the terminal side of the molecule of the organometal complex. In FIG. 2, the ligand is a 4-(2,2':6',2"-terpyridin-4'-yl) phenyl group. Here, the phenyl groups in the ligands 11A and 11B and the ethynylene groups in the connector 13 are connected.

Figure 3:
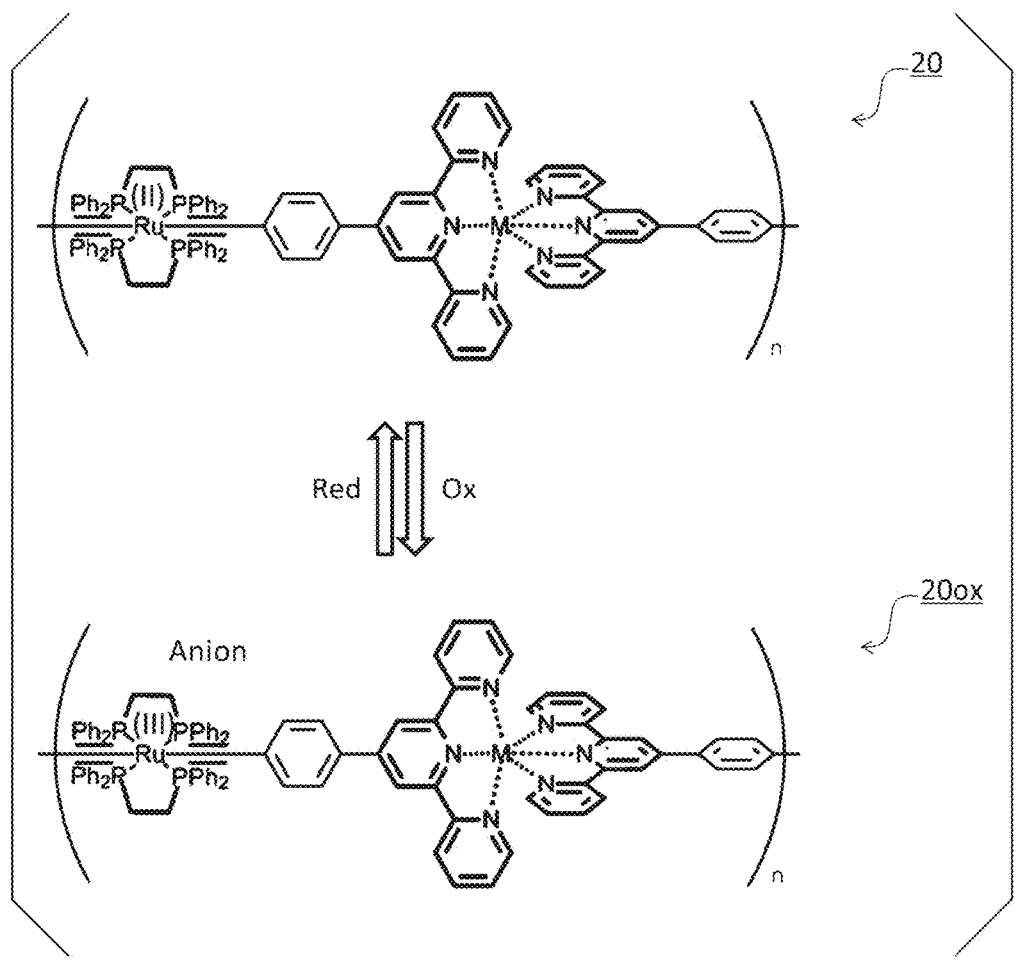
FIG. 3 is a diagram showing an example of a redox reaction of the organic/heterometallic hybrid polymer according to an embodiment of the present invention.

FIG. 3 is a diagram showing an example of a redox reaction of the organic/heterometallic hybrid polymer according to an embodiment of the present invention.

By oxidizing the organic/heterometallic hybrid polymer 20 according to an embodiment of the present invention, Ru(II) is oxidized to Ru(III) to form an oxidized organic/heterometallic hybrid polymer 20OX in which anions in the electrolyte are in close proximity.

By selecting Fe or Zn as the transition metal M which is a dissimilar transition metal to Ru, it is possible to absorb near infrared light by the intervalence charge transfer (IVCT) between Ru(III) and Fe(II) or Ru(III) and Zn(II).

(Production Method of Organic/Heterometallic Hybrid Polymer)

Next, an example of a method for producing an organic/heterometallic hybrid polymer according to an embodiment of the present invention will be described.

The method for producing an organic/heterometallic hybrid polymer according to the embodiment of the present invention includes an organometal complex synthesis step S1 and an organic/heterometallic hybrid polymer synthesis step S2.

(Organometal Complex Synthesis Step S1)

In this step, a terpyridine compound having an ethynyl group and a terpyridyl group is reacted with a compound containing $Ru(dppe)_2$ in an organic solvent, thereby synthesizing an organometal complex having $Ru(dppe)_2$ and a terpyridyl group at the terminal. As a reaction method, stirring and mixing can be employed.

Examples of the compound containing $Ru(dppe)_2$ include $Ru(dppe)_2Cl(OTf)$.

Examples of the organic solvent include methylene chloride.

Examples of the additive include sodium hexafluorophosphate and triethylamine.

The reaction temperature is preferably from 10 to 40° C.

The reaction time is preferably from 2 to 36 hours.

As a post-treatment process after completion of the reaction, it is preferable to perform column chromatography.

Here, examples of the terpyridine compound include 4'-(4-ethynylphenyl)-2,2':6',2"-terpyridine.

(Organic/Heterometallic Hybrid Polymer Synthesis Step S2)

In this step, the organometal complex and a transition metal compound are reacted in an organic solvent, thereby synthesizing the organic/heterometallic hybrid polymer.

Examples of the organic solvent include ethylene glycol, ethanol, methanol, chloroform, NMP, dimethylformamide and dimethyl sulfoxide.

The reaction temperature is preferably from 60 to 140° C.

As a post-treatment process after completion of the reaction, it is preferable to perform filtration and washing.

Figure 4:
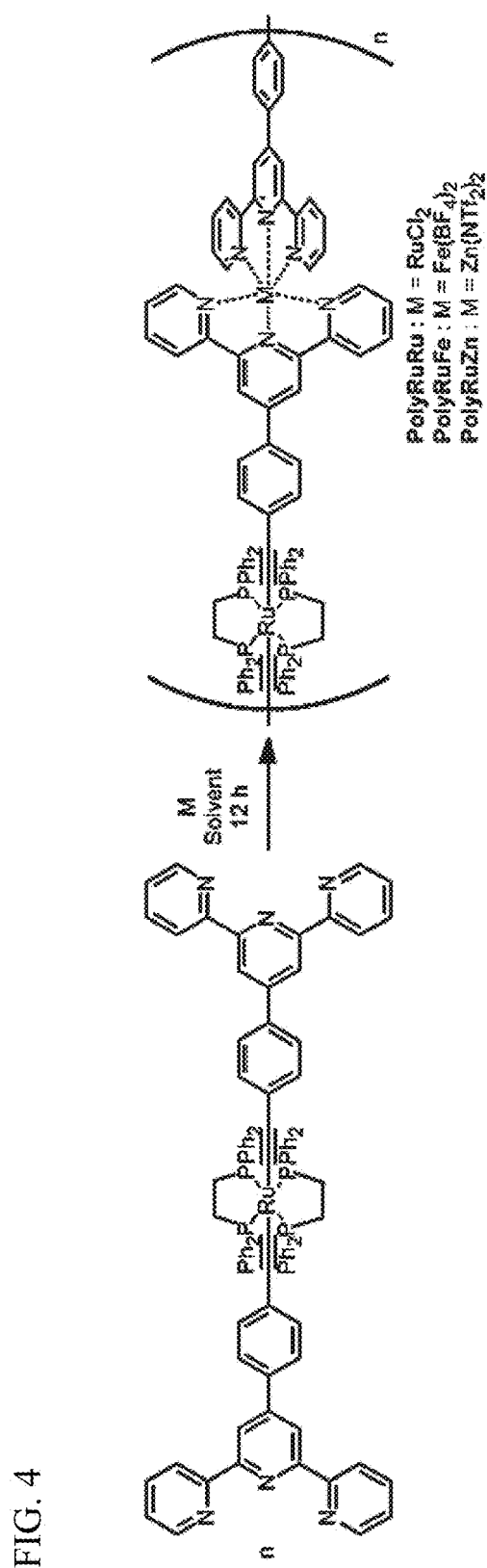
FIG. 4 is a chemical reaction formula in a step of synthesizing the organic/heterometallic hybrid polymer.

FIG. 4 is a chemical reaction formula in the organic/heterometallic hybrid polymer synthesis step. The terpyridyl groups in the ligand form a complex with the transition metal M, thereby linking a plurality of organometal complexes via the transition metal M in a linear manner.

It is preferable to react the transition metal compound in an amount from 1.0 molar equivalent or more to 1.1 molar equivalent or less, with respect to the aforementioned organometal complex. As a result, the organic/heterometallic hybrid polymer can be synthesized with high yield.

The aforementioned transition metal compound is preferably any one of $RuCl_2$, $Fe(BF_4)_2$, or $Zn(NTf_2)_2$. As a result, it is possible to synthesize a polymer having a corresponding transition metal.

$Zn(NTf_2)_2$ is zinc di[bis(trifluoromethanesulfonyl)imide] (zinc di[(trifluoromethylsulfonyl)imide)]).

The reaction time of the organometal complex and the transition metal compound is preferably at least 12 hours and not more than 36 hours. As a result, the organic/heterometallic hybrid polymer can be synthesized with an increased yield of 90% or higher.

(Organic/Heterometallic Hybrid Polymer Film)

Next, an organic/heterometallic hybrid polymer film according to an embodiment of the present invention will be described.

The organic/heterometallic hybrid polymer film according to an embodiment of the present invention is made of the organic/heterometallic hybrid polymer according to an embodiment of the present invention. As a result, it can be made into a film capable of causing an electrochromic reaction and can be applied to an optical device.

The film thickness is preferably at least 100 nm and not more than 1 mm, and more preferably at least 100 nm and not more than 400 nm. By ensuring that the film thickness is equal to or more than 100 nm, it is possible to stably retain the film. In addition, by ensuring that the film thickness is equal to or less than 1 mm, when used by being connected to the electrode, it is possible to increase the response speed of the electrochromic reaction with respect to the voltage control. It should be noted that the film thickness can be measured by observing the cross section with a scanning electron microscope.

It is preferred that the transition metal contained in the organic/heterometallic hybrid polymer is Fe or Zn. As a result, it is possible to cause an electrochromic reaction in the near infrared light region.

In the organic/heterometallic hybrid polymer film, a counter anion may be included as an optional component. Examples of the counter anion include a chloride ion, a tetrafluoroborate anion, a hexafluorophosphate anion, a bis (trifluoromethanesulfonyl)imide anion, a perchlorate ion, and an acetate ion.

The organic/heterometallic hybrid polymer film can be produced by dissolving an organic/heterometallic hybrid polymer in an organic solvent, and applying, and drying, the resultant onto a transparent electrode substrate.

Examples of the organic solvent include methanol, acetonitrile, dimethyl sulfoxide and dimethylformamide.

The organic/heterometallic hybrid polymer according to an embodiment of the present invention is a polymer in which a plurality of organometal complexes are linked in a linear manner by sandwiching the transition metal therebetween. The aforementioned organometal complex is formed by linking two ligands having a terpyridyl group by one connector having Ru(dppe)$_2$ and two ethynylene groups, so that a nitrogen atom at position 1' of the aforementioned terpyridyl group is directed toward the terminal side of the molecule of the organometal complex. In addition, the terpyridyl groups of at least two different organometal complexes of the plurality of organometal complexes are bound to one transition metal through a coordinate bond, thereby linking the plurality of organometal complexes by alternately sandwiching a plurality of transition metals therebetween. Therefore, it is possible to prepare a linear supramolecular polymer that links the organometal complexes and the transition metals alternately and is capable of causing an electrochromic reaction.

The organic/heterometallic hybrid polymer according to an embodiment of the present invention may be configured so that the aforementioned transition metal is any one of Ru, Fe or Zn. As a result, it is possible to prepare a linear supramolecular polymer that links the organometal complexes and the transition metals alternately and is capable of causing an electrochromic reaction.

The organic/heterometallic hybrid polymer according to an embodiment of the present invention may be configured so as to have a molecular weight $M_W$ of at least $10.5 \times 10^4$ and not more than $29.2 \times 10^4$. As a result, it is possible to form a stable film capable of causing an electrochromic reaction.

The method of producing an organic/heterometallic hybrid polymer according to an embodiment of the present invention is configured to include a step of synthesizing an organometal complex having a terpyridyl group at the terminal by reacting a terpyridine compound having an ethynyl group and a terpyridyl group with a compound containing Ru(dppe)$_2$ in an organic solvent, and a step of synthesizing the organic/heterometallic hybrid polymer by reacting the aforementioned organometal complex and a transition metal compound in an organic solvent. Therefore, it is possible to synthesize a linear supramolecular polymer with high yield that links the organometal complexes and the transition metals alternately and is capable of causing an electrochromic reaction.

The method of producing an organic/heterometallic hybrid polymer according to an embodiment of the present invention may be configured so as to react 1.0 equivalent or more transition metal compound with respect to the aforementioned organometal complex. As a result, it is possible to synthesize a linear supramolecular polymer with high yield that links the organometal complexes and the transition metals alternately and is capable of causing an electrochromic reaction.

The method of producing an organic/heterometallic hybrid polymer according to an embodiment of the present invention may be configured so that the aforementioned transition metal compound is any one of RuCl$_2$, Fe(BF$_4$)$_2$, or Zn(NTf$_2$)$_2$. As a result, it is possible to synthesize a linear supramolecular polymer with high yield that links the organometal complexes and the transition metals alternately and is capable of causing an electrochromic reaction.

The method of producing an organic/heterometallic hybrid polymer according to an embodiment of the present invention may be configured so that a reaction time of the organometal complex and the transition metal compound is equal to or more than 12 hours. As a result, it is possible to synthesize a linear supramolecular polymer with high yield that links the organometal complexes and the transition metals alternately and is capable of causing an electrochromic reaction.

The organic/heterometallic hybrid polymer film according to an embodiment of the present invention is configured to include the organic/heterometallic hybrid polymer described earlier. Therefore, it can be made into a film capable of causing an electrochromic reaction and can be applied to an optical device.

The organic/heterometallic hybrid polymer film according to an embodiment of the present invention may be configured so that the film thickness is at least 100 nm and not more than 1 mm. As a result, it is possible to stably retain the film and increase the response speed of the electrochromic reaction.

The organic/heterometallic hybrid polymer film according to an embodiment of the present invention may be configured so that a transition metal contained in the aforementioned organic/heterometallic hybrid polymer is a transition metal of Fe or Zn. As a result, it can be made into a film capable of causing an electrochromic reaction in the near infrared light region and can be applied to an optical device.

(Film of Linear Organic/Multimetallic Hybrid Polymer)

First, a film of a linear organic/multimetallic hybrid polymer according to a second embodiment of the present invention will be described.

Figure 18A:
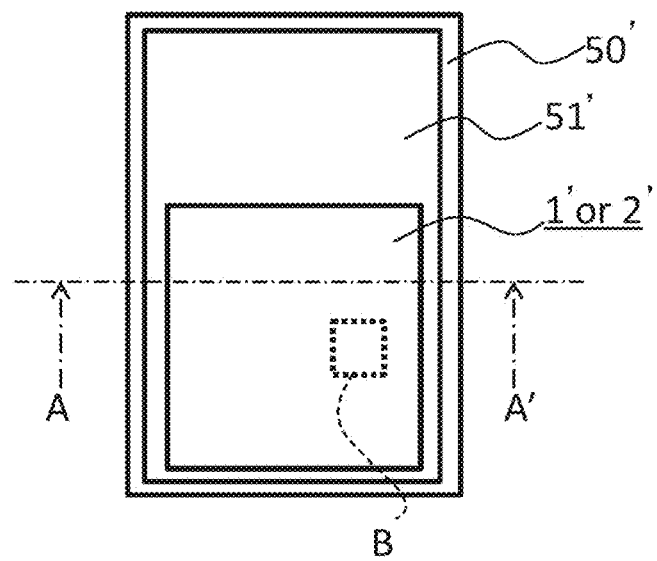
FIG. 18A is a diagram showing an example of an organic/multimetallic hybrid polymer film according to an embodiment of the present invention.
Figure 18B:
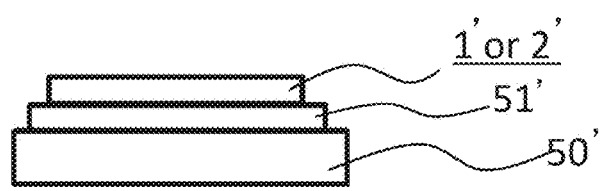
FIG. 18B is a diagram showing an example of an organic/multimetallic hybrid polymer film according to the present invention.

FIGS. 18A and 18B are diagrams showing an example of a linear organic/multimetallic hybrid polymer film according to a second embodiment of the present invention.

A linear organic/multimetallic hybrid polymer film 1' according to the second embodiment of the present invention is formed in a substantially rectangular shape in plan view on a transparent conductive film 51' of a glass substrate 50'. The plan view shape is not limited thereto. Also, it is not limited to the above embodiment to be formed on the transparent conductive film 51'. As the transparent conductive film 51', an ITO film or the like can be used.

The thickness of the linear organic/multimetallic hybrid polymer film is preferably at least 100 nm and not more than 1 mm, and more preferably at least 100 nm and not more than 400 nm. By ensuring that the film thickness is equal to or more than 100 nm, it is possible to stably retain the film. In addition, by ensuring that the film thickness is equal to or less than 1 mm, when used by being connected to the electrode, it is possible to increase the response speed of the electrochromic reaction with respect to the voltage control.

Figure 19:
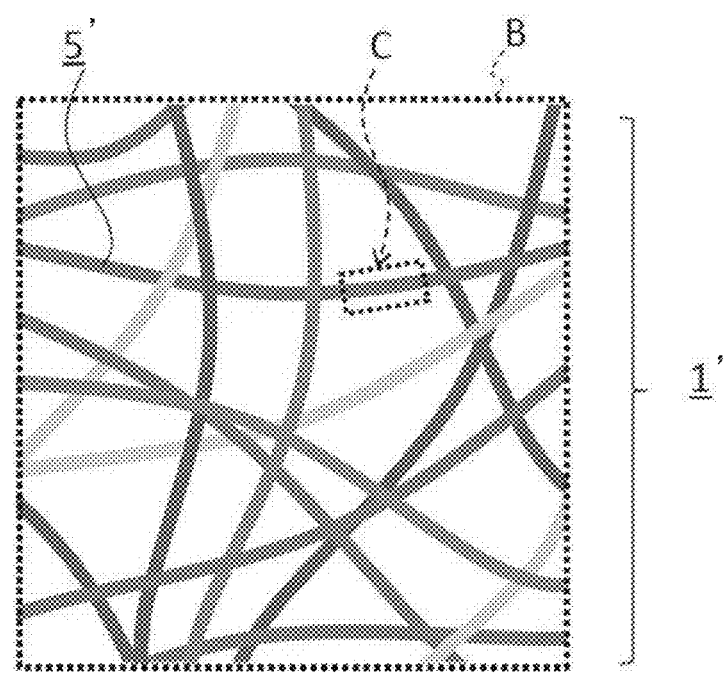
FIG. 19 is a diagram showing an example of an enlarged view of a portion B in FIG. 18A.

FIG. 19 is a diagram showing an example of an enlarged view of a portion B in FIG. 18A.

As shown in FIG. 19, a film 1' of a linear organic/multimetallic hybrid polymer according to an embodiment of the present invention is formed by mixing the linear organic/multimetallic hybrid polymer 5' according to an embodiment of the present invention in a mesh shape.

The film of the linear organic/multimetallic hybrid polymer film can be produced by dissolving a linear organic/multimetallic hybrid polymer in an organic solvent, and applying, and drying, the resultant onto a transparent electrode substrate. Examples of the organic solvent include methanol, acetonitrile, dimethyl sulfoxide and dimethylformamide.

(Linear Organic/Multimetallic Hybrid Polymer)

Next, a linear organic/multimetallic hybrid polymer according to a second embodiment of the present invention will be described.

Figure 20:
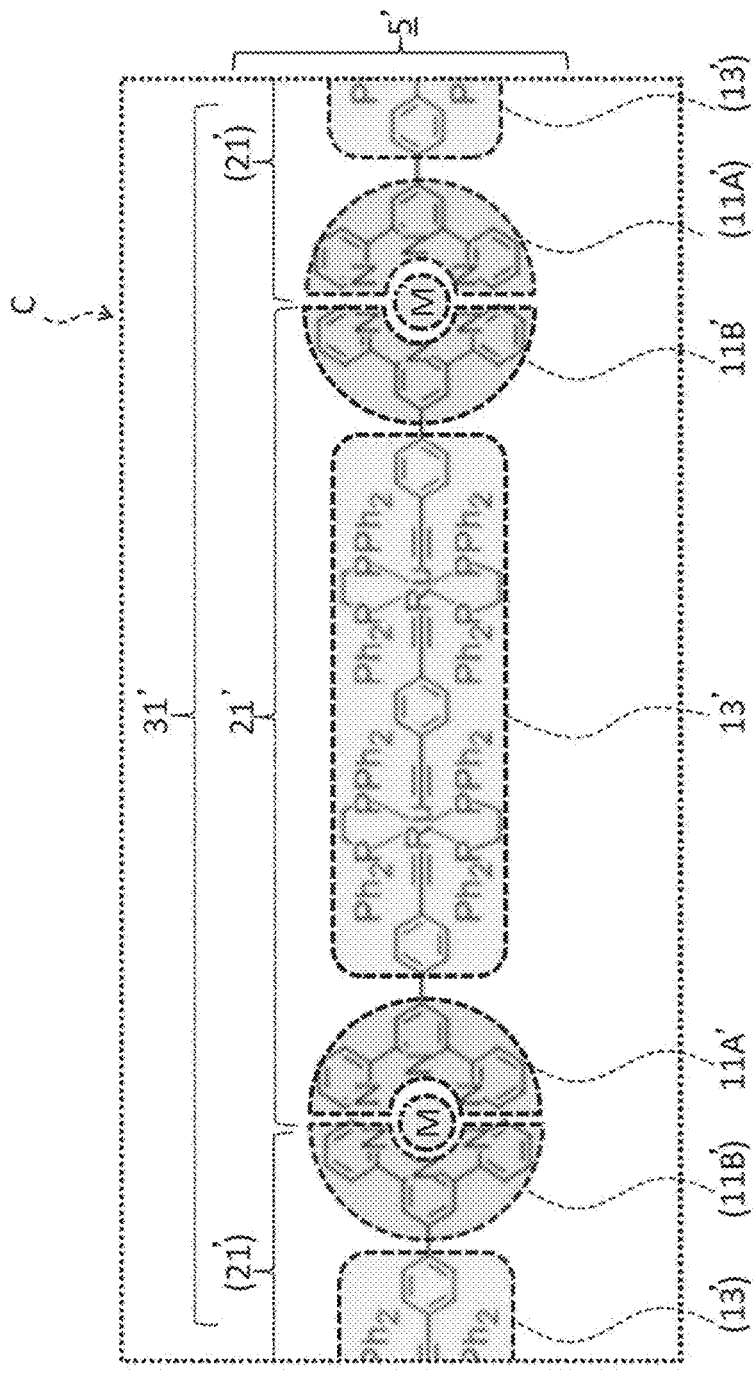
FIG. 20 is a diagram showing an example of a structural formula of a linear organic/multimetallic hybrid polymer constituting a portion C in FIG. 19.

FIG. 20 is a diagram showing an example of a structural formula of a linear organic/multimetallic hybrid polymer constituting a portion C in FIG. 19.

As shown in FIG. 20, the linear organic/multimetallic hybrid polymer 5' according to an embodiment of the present invention is a linear supramolecular polymer. More specifically, the linear organic/multimetallic hybrid polymer 5' according to an embodiment of the present invention is schematically configured to include only a linear portion 31' in which organometal ligands 21' are linearly linked while sandwiching the transition metals M' therebetween.

The organometal ligand 21' is formed by linking a connector 13' with ligands 11'A and 11'B.

The connector 13' is formed with a benzene ring at the center by linking two Ru(dppe)$_2$ via two ethynylene groups bonded to the benzene ring, while respectively connecting other ethynylene groups to each Ru(dppe)$_2$ and connecting phenyl groups to the ethynylene groups.

The ligands 11'A and 11'B are terpyridyl groups and are formed by connecting 4' position of the terpyridyl group to the para position of the phenyl group at both ends of the terminal of the connector 13'.

The aforementioned terpyridyl group forms a coordinate bond with the transition metal M' to connect a plurality of organometal ligands 21'.

Figure 21:
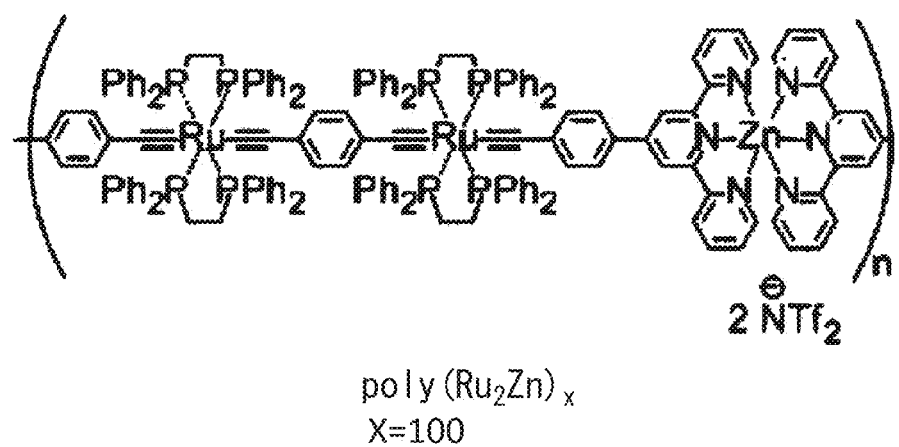
FIG. 21 is a chemical formula showing an example of a linear organic/multimetallic hybrid polymer 5' according to an embodiment of the present invention.

FIG. 21 is a chemical formula showing an example of a linear organic/multimetallic hybrid polymer 5' according to an embodiment of the present invention.

As shown in FIG. 21, the linear organic/multimetallic hybrid polymer 5' according to an embodiment of the present invention is denoted as a plurality of organic metals poly(Ru$_2$Zn)X. X represents the proportion of linear portions (mol %) when the sum of the linear portions and branched portions constituting the organic/multimetallic hybrid polymer is defined as 100 mol %. In FIG. 21, since the organic/multimetallic hybrid polymer is linear, X=100. In other words, it represents poly(Ru$_2$Zn)$_{100}$. In FIG. 21, n is a natural number of 2 or more. As shown in FIG. 21, the linear organic/multimetallic hybrid polymer 5' includes a unit structure derived from the linear portion, i.e., a unit structure containing the organometal ligand 21' and the transition metal M' (a structure enclosed in parentheses).

By oxidizing the linear organic/multimetallic hybrid polymer 5' according to an embodiment of the present invention, Ru(II) is oxidized to Ru(III) to form an oxidized organic/multimetallic hybrid polymer in which anions in the electrolyte are in close proximity.

Examples of the transition metal M' include Fe, Zn, Co, or Ru. As a result, it is possible to absorb near infrared light and to cause an electrochromic reaction in the near infrared light region by the intervalence charge transfer (IVCT) between Ru(III) and Fe(II) or Ru(III) and Zn(II).

Since the linear organic/multimetallic hybrid polymer 5' according to an embodiment of the present invention is configured so that not only hetero transition metals Zn and Ru are closely arranged, but also the same transition metals Ru and Ru are closely arranged, for example, not only the absorption of IVCT between hetero metals Zn—Ru, but also the absorption of IVCT between the same metals Ru—Ru are observed. As a result, it can be made into a film capable of causing an electrochromic reaction at two wavelengths within the near infrared to infrared region. In addition, it is possible to reduce the absorbance at one absorption peak wavelength while increasing the absorbance at the other absorption peak wavelength, and vice versa, by the ON/OFF of the voltage application, and to block the light by switching ON/OFF at two wavelengths within the near infrared to infrared region.

(Synthesis Method of Linear Organic/Multimetallic Hybrid Polymer)

Next, a method for synthesizing a linear organic/multimetallic hybrid polymer according to an embodiment of the present invention will be described.

The method for producing a linear organic/multimetallic hybrid polymer according to an embodiment of the present invention includes a binuclear organometallic site synthesis step S1, an organometal ligand synthesis step S2 and a linear organic/multimetallic hybrid polymer synthesis step S3.

(Binuclear Organometallic Site Synthesis Step S1)

Figure 22:
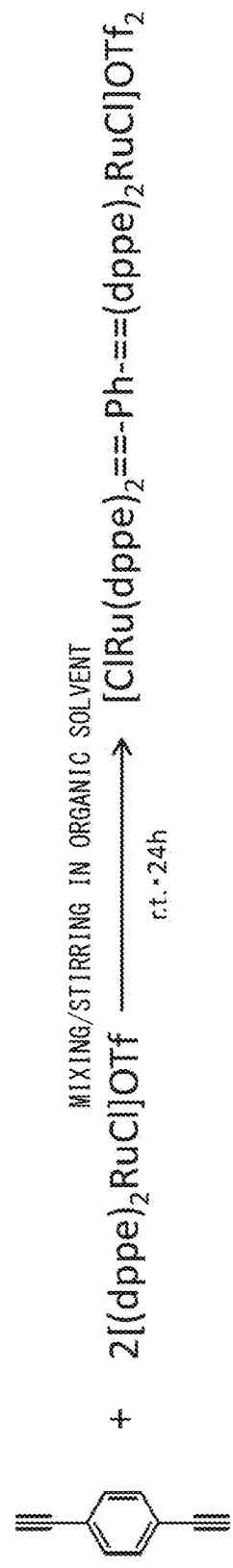
FIG. 22 is an example of a chemical reaction formula for the synthesis of a binuclear organometallic site.

FIG. 22 represents a chemical reaction formula for the synthesis of a binuclear organometallic site.

First, a diethynylbenzene and Ru(dppe)$_2$Cl(OTf) are reacted in an organic solvent.

Examples of the organic solvent include methylene chloride, chloroform, carbon tetrachloride and chlorobenzene. Among them, methylene chloride and chloroform are preferred.

The reaction temperature is preferably from room temperature to 80° C., and more preferably from room temperature to 40° C.

The reaction time is preferably from 24 to 72 hours, and more preferably from 24 to 48 hours.

Then, the resulting precipitate is collected by filtration and washed with an organic solvent (for example, cold methylene chloride), followed by drying to obtain [ClRu(II)(dppe)$_2$=C=CH-Ph-CH=C=(dppe)$_2$Ru(II)Cl](OTf)$_2$ which is a salt of Ru(II)(dppe)$_2$=C=CH—C$_6$H$_4$—HC=C=Ru(II)(dppe)$_2$Cl$_2$. This is the binuclear organometallic site.

(Organometal Ligand Synthesis Step S2)

Figure 23:
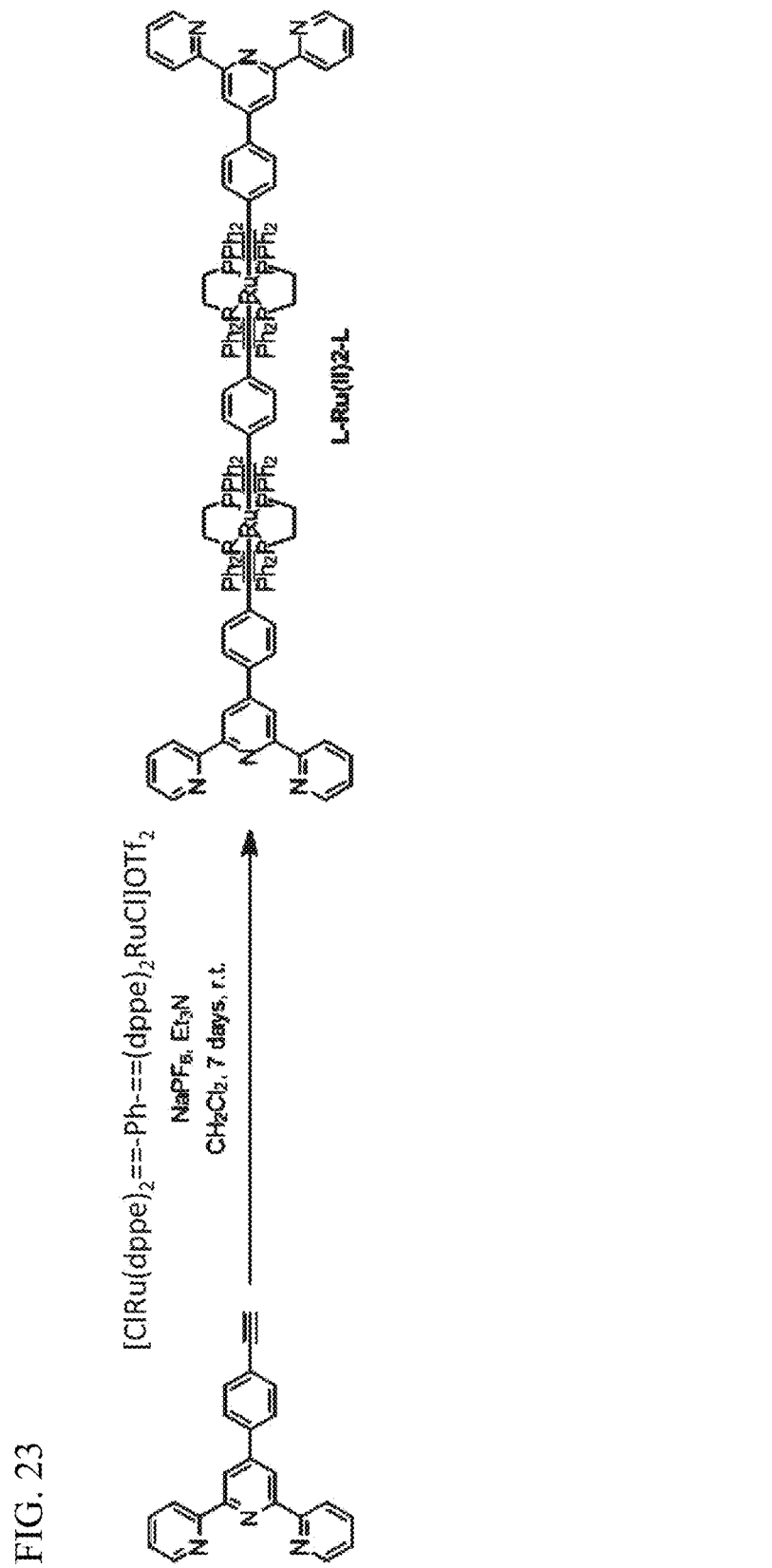
FIG. 23 is an example of a chemical reaction formula for the synthesis of an organometal ligand.

FIG. 23 represents a chemical reaction formula for the synthesis of an organic metal ligand.

In an organic solvent, a terpyridine compound having an ethynyl group and a terpyridyl group is reacted with [ClRu(II)(dppe)$_2$=C=CH-Ph-CH=C=(dppe)$_2$Ru(II)Cl](OTf)$_2$ in a nitrogen atmosphere under the presence of a base and an inorganic salt.

Here, examples of the terpyridine compound include 4'-(4-ethynylphenyl)-2,2':6',2''-terpyridine.

Examples of the organic solvent include methylene chloride, chloroform, carbon tetrachloride and chlorobenzene. Among them, methylene chloride and chloroform are preferred.

Examples of the base include triethylamine, tripropylamine, tributylamine, trihexylamine and dimethylaniline. Among them, triethylamine is preferred.

Examples of the inorganic salt include sodium hexafluorophosphate, lithium hexafluorophosphate, ammonium hexafluorophosphate, sodium tetrafluoroborate, sodium perchlorate, and ammonium perchlorate. Among them, sodium hexafluorophosphate is preferred.

The reaction time is preferably from 1 to 14 days, and more preferably from 5 to 9 days.

The reaction temperature is preferably from 10 to 60° C., and more preferably from room temperature to 40° C.

Then, a poor solvent is added to the reaction solution for precipitation, followed by filtration to wash the resulting solid with the poor solvent, thereby synthesizing an organometal ligand (L-Ru(II)$_2$-L) having a terpyridyl group at the terminal and including two Ru(dppe)$_2$.

Examples of the poor solvent include diethyl ether and acetone. Among them, diethyl ether is preferred.

(Linear Organic/Multimetallic Hybrid Polymer Synthesis Step S3)

Figure 24:
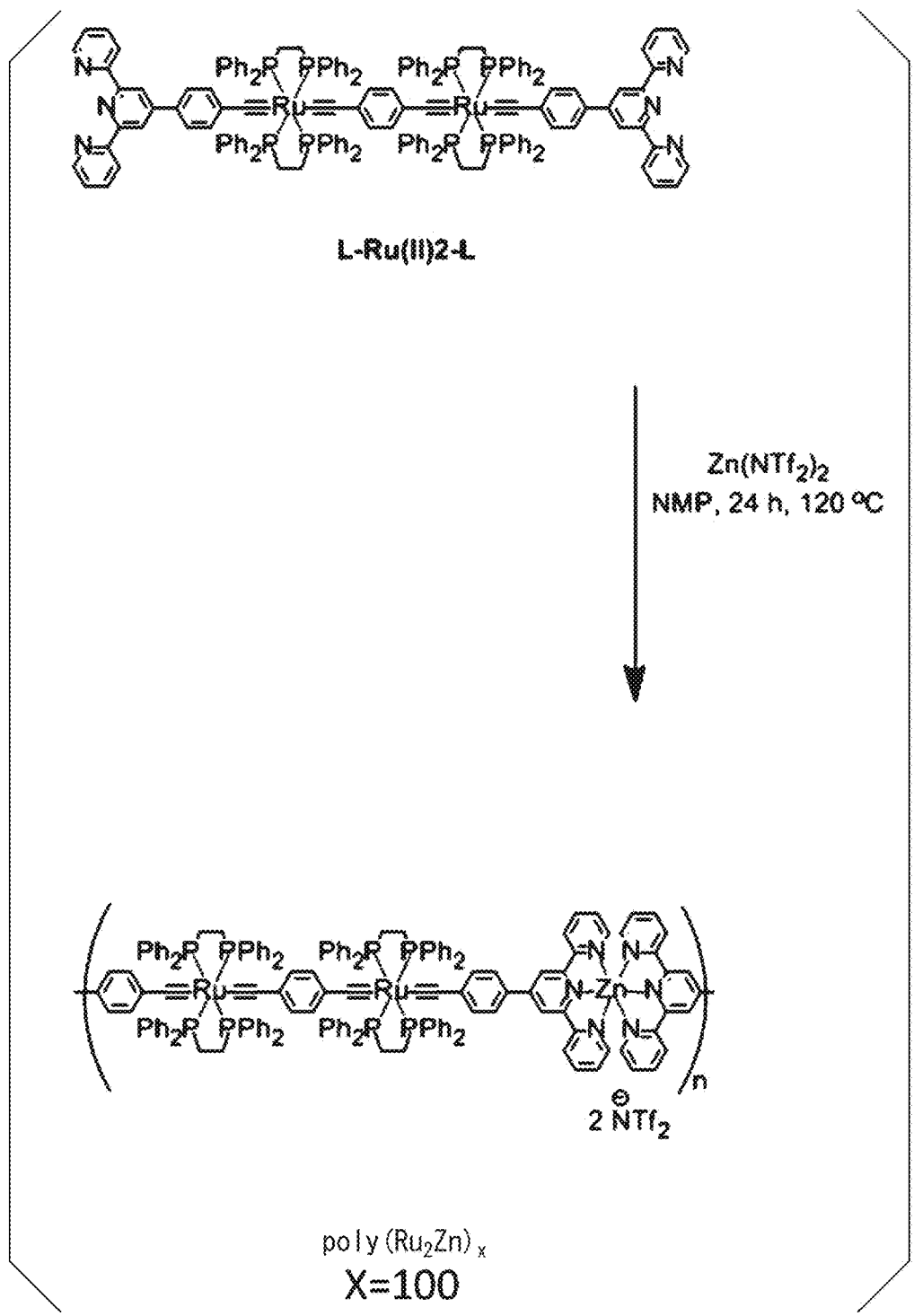
FIG. 24 is an example of a chemical reaction formula for the synthesis of a linear organic/multimetallic hybrid polymer.

FIG. 24 represents a chemical reaction formula for the synthesis of a linear organic/multimetallic hybrid polymer.

In this step, the organometal ligand (L-Ru(II)$_2$-L) and a transition metal compound (for example, Zn(NTf$_2$)$_2$) are reacted in an organic solvent to synthesize a linear organic/multimetallic hybrid polymer (poly(Ru$_2$Zn)X, X=100) composed only of linear portions.

It is preferable to react 1.0 molar equivalent to 2.0 molar equivalents of the transition metal compound, with respect to the aforementioned organometal ligand. As a result, the linear organic/multimetallic hybrid polymer can be synthesized with high yield.

In FIG. 24, the degree of polymerization (the number of n) can be adjusted by changing the number of molar equivalents of the transition metal compound to be added, with respect to the organometal ligand. That is, when 1.0 molar equivalent of the transition metal compound is reacted with respect to the aforementioned organometal ligand, the degree of polymerization (n) is increased, and the degree of polymerization (n) becomes smaller as the number of molar equivalents of the transition metal compound to be reacted is increased.

As the aforementioned transition metal compound, in addition to Zn(NTf$_2$)$_2$, Zn(BF$_4$)$_2$, Zn(OAc)$_2$, ZnCl$_2$, and the like can be employed. Among them, Zn(NTf$_2$)$_2$ is preferred.

Zn(NTf$_2$)$_2$ is zinc di[bis(trifluoromethanesulfonyl)imide] (zinc di[(trifluoromethylsulfonyl)imide)]).

In addition, as the aforementioned transition metal compound, Fe(BF$_4$)$_2$, Fe(OAc)$_2$, and FeCl$_2$ can also be used. As a result, it is possible to synthesize a polymer containing Fe.

The reaction time of the organometal ligand and the transition metal compound is preferably from 3 to 24 hours, and more preferably from 6 to 12 hours. As a result, the linear organic/multimetallic hybrid polymer can be synthesized with an increased yield of 80% or higher.

As the organic solvent, NMP, dimethylformamide, dimethyl sulfoxide, chlorobenzene and propylene carbonate are preferred, and among these, NMP and dimethylformamide are more preferred.

The reaction temperature is preferably from 80 to 160° C., and more preferably from 100 to 120° C.

As a post-treatment process after completion of the reaction, it is preferable to perform precipitation in a poor solvent and filtration, followed by washing with a poor solvent.

Examples of the poor solvent include diethyl ether, acetone, methylene chloride, chloroform and water. Among them, diethyl ether, chloroform and water are preferred.

(Film of Branched Organic/Multimetallic Hybrid Polymer)

Next, a film of a branched organic/multimetallic hybrid polymer according to an embodiment of the present invention will be described.

Figure 25:
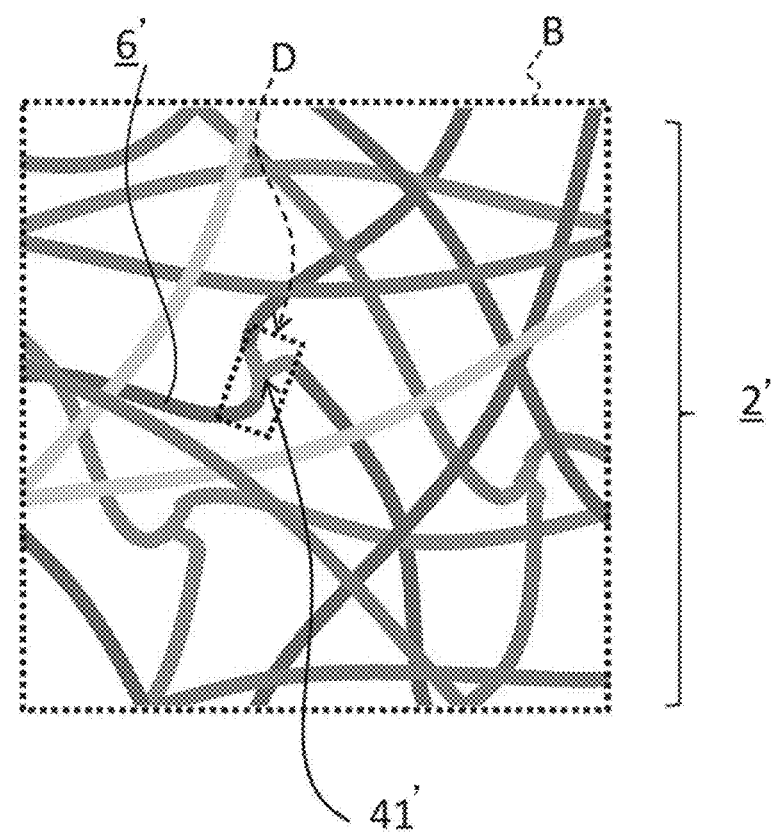
FIG. 25 is a diagram showing another example of an enlarged view of a portion B in FIG. 18A.

FIG. 25 is a diagram showing another example of an enlarged view of a portion B in FIG. 18A.

As shown in FIG. 25, a film 2' of a branched organic/multimetallic hybrid polymer according to an embodiment of the present invention may be configured so as to be formed by mixing the branched organic/multimetallic hybrid polymer 6' according to an embodiment of the present invention in a mesh shape.

The branched organic/multimetallic hybrid polymer 6' has a branched portion 41' linking the linear portion with 2 or more different linear portions and branching into three or more directions, and can form a mesh structure more firmly. As a result, the heat resistance improves, and the stability of the film is increased.

The film of the branched organic/multimetallic hybrid polymer can be produced by dissolving a branched organic/multimetallic hybrid polymer in an organic solvent, and applying, and drying, the resultant onto a transparent electrode substrate.

Examples of the organic solvent include heated dimethyl sulfoxide, heated dimethylformamide, and heated chlorobenzene.

(Branched Organic/Multimetallic Hybrid Polymer)

Next, a branched organic/multimetallic hybrid polymer according to an embodiment of the present invention will be described.

Figure 26:
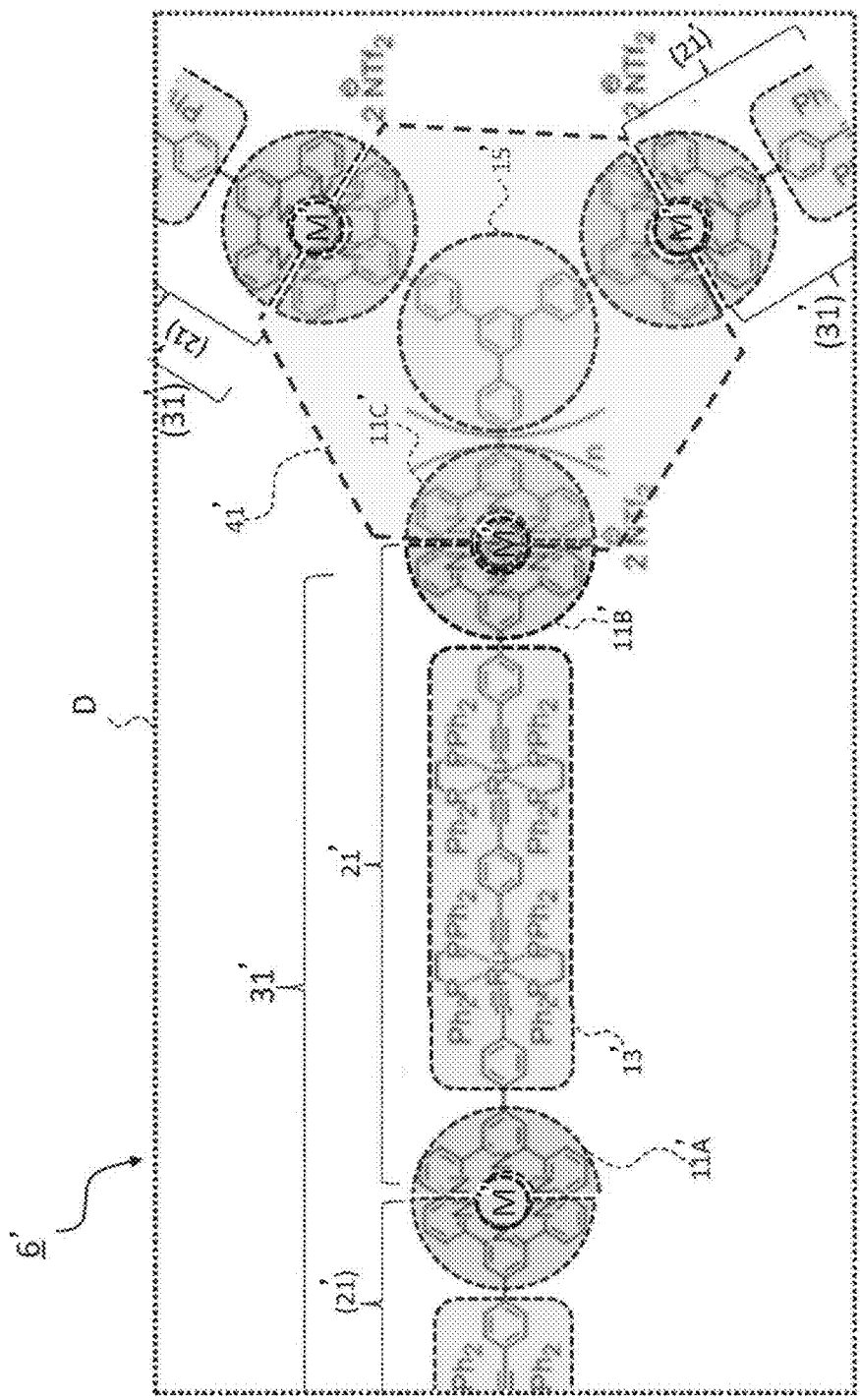
FIG. 26 is a diagram showing an example of a structural formula of a branched organic/multimetallic hybrid polymer constituting a portion D in FIG. 25.

FIG. 26 is a diagram showing an example of a structural formula of a branched organic/multimetallic hybrid polymer constituting a portion D in FIG. 25.

As shown in FIG. 26, the branched organic/multimetallic hybrid polymer 6' according to an embodiment of the present invention is a branched supramolecular polymer. More specifically, the branched organic/multimetallic hybrid polymer 6' according to an embodiment of the present invention is schematically configured to include not only a linear portion 31' in which organometal ligands 21' are linearly linked while sandwiching the transition metals M' therebetween, but also a branched portion 41' which connects the linear portion 31' with two different linear portions (31'), (31').

The branched portion 41' is formed by linking a ligand 11'C to a branch element (triphenylbenzene) 15', has a structure branched into three or more directions with the branch element at the center, and has ligands at the branched ends. As a result, it is possible to prepare an organic/multimetallic hybrid polymer branched in three or more directions and in which the linear portion is linked to two or more different linear portions.

The organometal ligand 21' is configured to have the same configuration as shown in the description of the linear organic/multimetallic hybrid polymer according to an embodiment of the present invention. That is, the organometal ligand is formed by linking one connector 13' with two ligands 11'A and 11'B. The connector 13' is formed with a benzene ring at the center by linking two Ru(dppe)$_2$ via two ethynylene groups bonded to the benzene ring, while respectively coupling other ethynylene groups to each Ru(dppe)$_2$ and respectively connecting phenyl groups to the ethynylene groups. The ligands 11'A and 11'B are terpyridyl groups and 4' position of the terpyridyl group is connected to the para position of the phenyl group at both ends of the terminal of the connector 13'. The aforementioned terpyridyl groups of at least two different organic metal ligands 21' of the plurality of organometal ligands 21' are bound to one transition metal M' through a coordinate bond, thereby linearly linking the plurality of organic metal ligands 21' by alternately sandwiching the plurality of transition metals M' therebetween.

Figure 27:
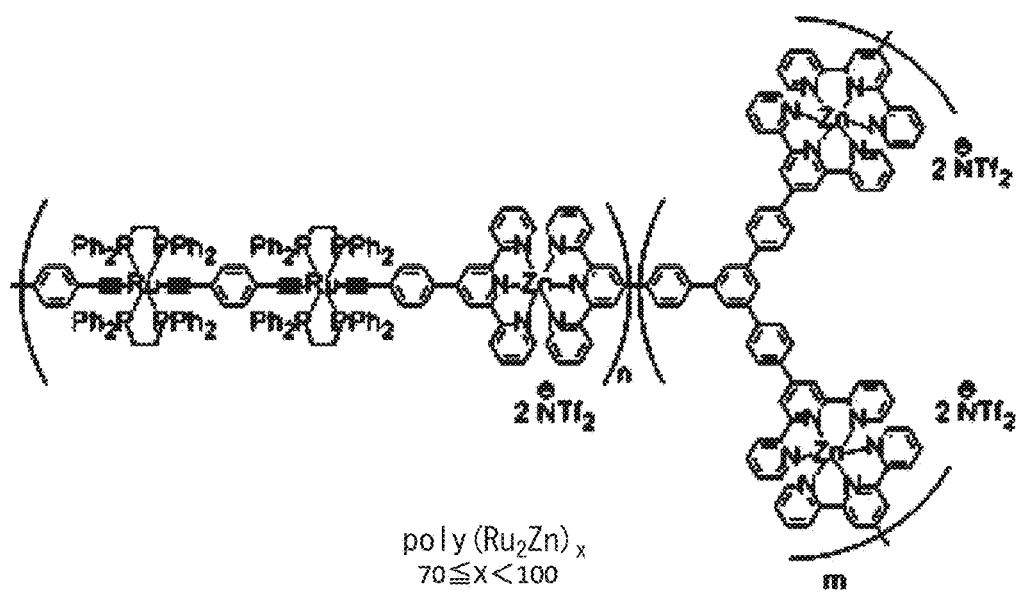
FIG. 27 is a chemical formula showing an example of a branched organic/multimetallic hybrid polymer 6' according to an embodiment of the present invention.

FIG. 27 is a chemical formula showing an example of a branched organic/multimetallic hybrid polymer 6' according to an embodiment of the present invention.

As shown in FIG. 27, the branched organic/multimetallic hybrid polymer 6' according to an embodiment of the present invention is denoted as poly(Ru$_2$Zn)X, where X is 70≤X<100. In FIG. 27, n and m are natural numbers of 2 or more. n corresponds to a linear moiety, whereas m corresponds to a branched moiety. Therefore, X, n, and m are associated by the formula: X=100n/(n+m).

Examples thereof include poly($Ru_2Zn$)$_{90}$, poly($Ru_2Zn$)$_{80}$, poly($Ru_2Zn$)$_{70}$, and the like. As shown in FIG. 27, the branched organic/multimetallic hybrid polymer 6' includes a unit structure derived from the linear portion, (i.e., a unit structure containing the organometal ligand 21' and the transition metal M'), and a unit structure derived from the branched portion.

By oxidizing the branched organic/multimetallic hybrid polymer 6' according to an embodiment of the present invention, Ru(II) is oxidized to Ru(III) to form an oxidized organic/multimetallic hybrid polymer in which anions in the electrolyte are in close proximity.

Examples of the transition metal M include Fe or Zn. As a result, it is possible to absorb near infrared light and to cause an electrochromic reaction in the near infrared light region by the intervalence charge transfer (IVCT) between Ru(III) and Fe(II) or Ru(III) and Zn(II).

Since the branched organic/multimetallic hybrid polymer 6' according to an embodiment of the present invention is configured so that not only hetero transition metals Zn and Ru are closely arranged, but also the same transition metals Ru and Ru are closely arranged, for example, not only the absorption of IVCT between hetero metals Zn—Ru, but also the absorption of IVCT between the same metals Ru—Ru are observed. As a result, it can be made into a film capable of causing an electrochromic reaction at two wavelengths within the near infrared to infrared region. In addition, it is possible to reduce the absorbance at one absorption peak wavelength while increasing the absorbance at the other absorption peak wavelength, and vice versa, by the ON/OFF of the voltage application, and to block the light by switching ON/OFF at two wavelengths within the near infrared to infrared region.

(Synthesis Method of Branched Organic/Multimetallic Hybrid Polymer)

Next, a method for synthesizing a branched organic/multimetallic hybrid polymer according to an embodiment of the present invention will be described.

The method for producing a branched organic/multimetallic hybrid polymer according to an embodiment of the present invention includes a binuclear organometallic site synthesis step S1, an organometal ligand synthesis step S2, a linear organic/multimetallic hybrid polymer synthesis step S3, and a branched organic/multimetallic hybrid polymer synthesis step S4.

(Binuclear Organometallic Site Synthesis Step S1)

A binuclear organometallic site is synthesized in the same manner as in the binuclear organometallic site synthesis step S1 described in the method for producing a linear organic/multimetallic hybrid polymer according to an embodiment of the present invention.

(Organometal Ligand Synthesis Step S2)

An organometal ligand is synthesized in the same manner as in the organic metal ligand synthesis step S2 described in the method for producing a linear organic/multimetallic hybrid polymer according to an embodiment of the present invention.

(Linear Organic/Multimetallic Hybrid Polymer Synthesis Step S3)

A linear organic/multimetallic hybrid polymer is synthesized in the same manner as in the linear organic/multimetallic hybrid polymer synthesis step S3 of the method for producing a linear organic/multimetallic hybrid polymer according to an embodiment of the present invention.

(Branched Organic/Multimetallic Hybrid Polymer Synthesis Step S4)

Figure 28:
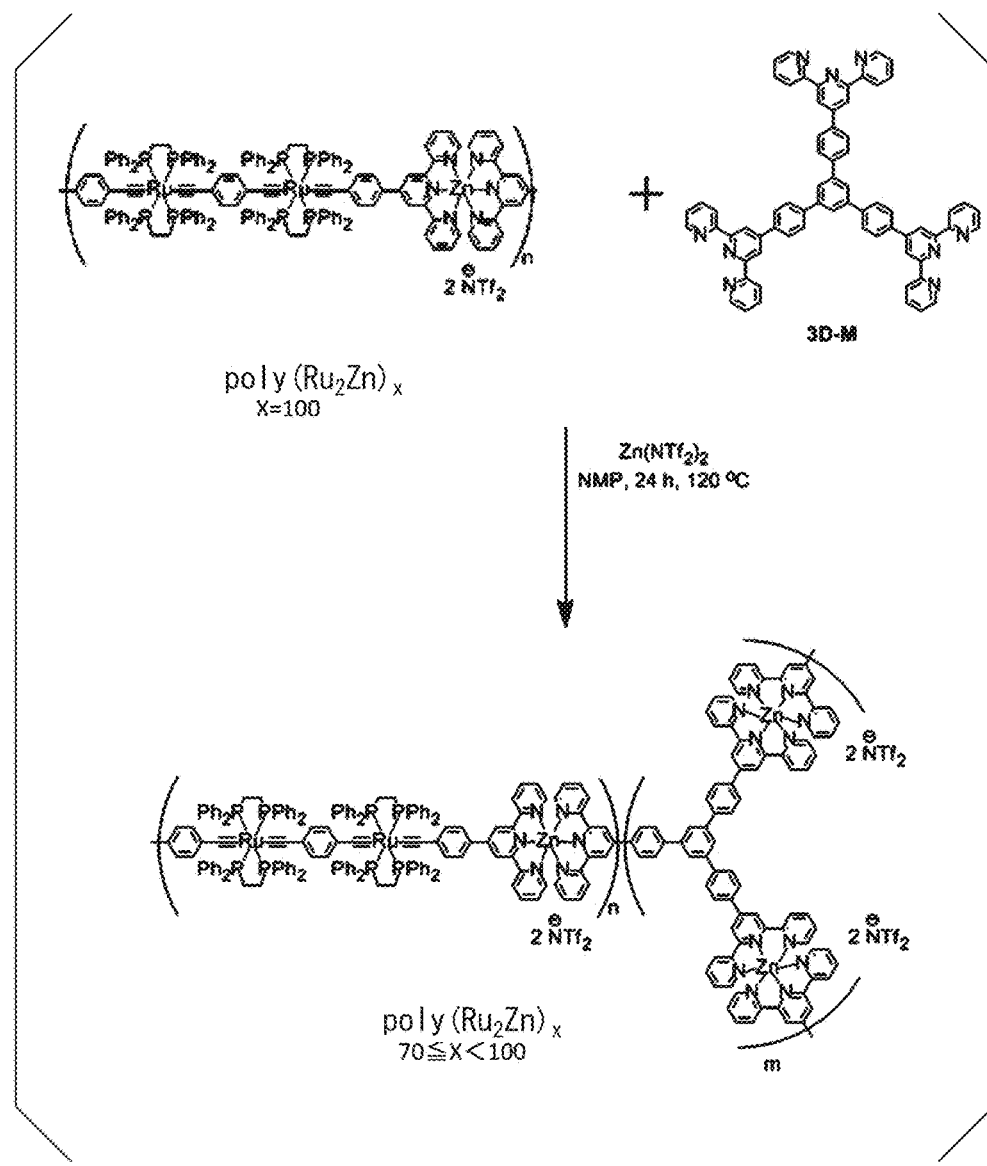
FIG. 28 is a chemical reaction formula in a step of synthesizing the branched organic/multimetallic hybrid polymer.

FIG. 28 is a chemical reaction formula in a step of synthesizing the branched organic/multimetallic hybrid polymer.

In this step, the branched organic/multimetallic hybrid polymer is synthesized by reacting the linear organic/multimetallic hybrid polymer 5', a transition metal compound (for example, Zn($NTf_2$)$_2$) and a branched compound connectable in three directions (for example, 1,3,5-Tris[4-(2,2':6',2"-terpyridin-4'-yl)phenyl]benzene) in an organic solvent (for example, NMP).

The mixing amount of the transition metal compound (for example, Zn($NTf_2$)$_2$) may be at least 10 molar parts and not more than 60 molar parts, with respect to the combined total of 100 molar parts of the same type of the transition metal constituting the linear organic/multimetallic hybrid polymer (for example, refers to Zn in the case of mixing Zn($NTf_2$)$_2$) and the transition metal to be mixed (for example, refers to Zn in the case of mixing Zn($NTf_2$)$_2$). Of the various possibilities, the mixing amount is preferably at least 10 molar parts and not more than 30 molar parts.

As the aforementioned transition metal compound, in addition to Zn($NTf_2$)$_2$, Zn($BF_4$)$_2$, Zn($OAc$)$_2$, $ZnCl_2$, and the like can be employed. Among them, Zn($NTf_2$)$_2$ is preferred.

In addition, as the aforementioned transition metal compound, Fe($BF_4$)$_2$, Fe($OAc$)$_2$, and $FeCl_2$ can also be used. As a result, it is possible to synthesize a polymer containing Fe in the branched portion.

The reaction time of the organometal ligand and the transition metal compound is preferably from 6 to 48 hours, and more preferably from 12 to 24 hours. As a result, the branched organic/multimetallic hybrid polymer can be synthesized with an increased yield of 80% or higher.

Examples of the organic solvent include NMP: N-Methylpyrrolidone, dimethylformamide, dimethyl sulfoxide, chlorobenzene and propylene carbonate. Among them, NMP and dimethylformamide are preferred.

The reaction temperature is preferably from 80 to 150° C., and more preferably from 100 to 120° C.

The branched compound is branched into three or more directions with the branch element at the center, and has ligands at the ends of the branched molecule. Examples of the branched compound include 1,3,5-Tris[4-(2,2':6',2"-terpyridin-4'-yl)phenyl]benzene (hereinafter, sometimes referred to as "3D-M"), and the like.

As the branch element, triphenylmethane can be used other than triphenyl benzene. In addition, tetraphenylmethane which is a branched compound branched in four or more directions may also be used.

The mixing amount of the branched compound is preferably at least 10 molar parts and not more than 30 molar parts, relative to the combined total of 100 molar parts of the linear portion and the branched compound constituting the linear organic/multimetallic hybrid polymer.

The linear organic/multimetallic hybrid polymer 5' or branched organic/multimetallic hybrid polymer 6' according to an embodiment of the present invention includes a linear portion 31' in which organometal ligands 21' are linearly linked while sandwiching the transition metals M' therebetween. The organometal ligand 21' is formed by linking a connector 13' with ligands 11'A and 11'B. In the connector 13', with a benzene ring at the center, two Ru(dppe)$_2$ are linked via two ethynylene groups bonded to the benzene ring, other ethynylene groups are respectively bonded to each Ru(dppe)$_2$, and phenyl groups are respectively connected to the ethynylene groups. The ligands 11'A and 11'B are terpyridyl groups and connected to the phenyl groups of the connector 13'. It is configured so that the aforementioned terpyridyl groups of at least two different organometal ligands 21' of the plurality of organometal ligands 21' are bound to one transition metal M' through a coordinate bond, thereby linking the plurality of organometal ligands 21' by alternately sandwiching the plurality of transition metals M' therebetween. For this reason, it is possible to prepare a linear or branched polymer, enhance the film stability, provide electrochromic properties in the infrared light region and increase the repetition stability.

The linear organic/multimetallic hybrid polymer 5' or branched organic/multimetallic hybrid polymer 6' according to an embodiment of the present invention may be configured so that the transition metal M is Fe, Zn, Co or Ru. As a result, it is possible to enhance the film stability by making the linear portion into a long chain, provide electrochromic properties in the infrared light region and increase the repetition stability.

The linear organic/multimetallic hybrid polymer 5' according to an embodiment of the present invention may be configured so as to be linear. As a result, it is possible to provide electrochromic properties in the infrared light region and increase the repetition stability.

The branched organic/multimetallic hybrid polymer 6' according to an embodiment of the present invention may be configured so as to be branched. As a result, it is possible to increase the film stability and increase the repetition stability.

The branched organic/multimetallic hybrid polymer 6' according to an embodiment of the present invention may be configured to have a branched portion 41' composed of 1,3,5-Tris[4-(2,2':6',2"-terpyridin-4'-yl)phenyl]benzene. As a result, it is possible to link the linear portion with two or more different linear portions so as to branch into three or more directions, increase the film stability and increase the repetition stability.

The branched organic/multimetallic hybrid polymer 6' according to an embodiment of the present invention may be configured so that the content of the branched portion 41' is at least 10 molar parts and not more than 30 molar parts, relative to the total number of moles of the linear portions and branched portions constituting the organic/multimetallic hybrid polymer. As a result, it is possible to increase the film stability and increase the repetition stability.

The method of synthesizing the linear organic/multimetallic hybrid polymer 5' or branched organic/multimetallic hybrid polymer 6' according to an embodiment of the present invention is configured to include a step S1 of synthesizing a binuclear organometallic site containing two Ru(dppe)$_2$ by reacting 1 equivalent of diethynylbenzene and 2 equivalents of Ru(dppe)$_2$Cl(OTf) in an organic solvent, a step S2 of synthesizing an organometal ligand having a terpyridyl group at the terminal and two Ru(dppe)$_2$ by reacting 2 equivalents of a terpyridine compound having an ethynyl group and a terpyridyl group with 1 equivalent of a binuclear organometallic site in an organic solvent, and a step S3 of synthesizing a linear organic/multimetallic hybrid polymer by reacting the aforementioned organometal ligand and a transition metal compound in an organic solvent. For this reason, it is possible to synthesize an organic/multimetallic hybrid polymer exhibiting electrochromic properties in the infrared light region and high repetition stability with high yield.

The method of synthesizing the branched organic/multimetallic hybrid polymer 6' according to an embodiment of the present invention is configured to synthesize a branched organic/multimetallic hybrid polymer by reacting the aforementioned linear organic/multimetallic hybrid polymer, a branched compound branched into three or more directions with a branch element at the center and having a ligand at the end of the branched molecule, and a transition metal compound. For this reason, it is possible to synthesize a branched organic/multimetallic hybrid polymer exhibiting electrochromic properties in the infrared light region and high repetition stability with high yield.

The method of synthesizing the branched organic/multimetallic hybrid polymer 6' according to an embodiment of the present invention may be configured so that the aforementioned branched compound is 1,3,5-Tris[4-(2,2':6',2"-terpyridin-4'-yl)phenyl]benzene. As a result, it is possible to synthesize a branched organic/multimetallic hybrid polymer exhibiting electrochromic properties in the infrared light region and high repetition stability with high yield.

The method of synthesizing the branched organic/multimetallic hybrid polymer 6' according to an embodiment of the present invention may be configured so that a mixing amount of the aforementioned branched compound is at least 10 molar parts and not more than 30 molar parts, relative to the combined total of 100 molar parts of the linear portions constituting the linear organic/multimetallic hybrid polymer. As a result, it is possible to synthesize a branched organic/multimetallic hybrid polymer exhibiting electrochromic properties in the infrared light region and high repetition stability with high yield.

The method of synthesizing the linear organic/multimetallic hybrid polymer 5' or branched organic/multimetallic hybrid polymer 6' according to an embodiment of the present invention may be configured so as to react 1.0 equivalent or more transition metal compound with respect to the aforementioned organometal ligand. As a result, it is possible to synthesize an organic/multimetallic hybrid polymer exhibiting electrochromic properties in the infrared light region and high repetition stability with high yield.

The method of synthesizing the linear organic/multimetallic hybrid polymer 5' or branched organic/multimetallic hybrid polymer 6' according to an embodiment of the present invention may be configured so that the aforementioned transition metal compound is Fe(BF$_4$)$_2$ or Zn(NTf$_2$)$_2$. As a result, it is possible to synthesize an organic/multimetallic hybrid polymer exhibiting electrochromic properties in the infrared light region and high repetition stability with high yield.

The method of synthesizing the linear organic/multimetallic hybrid polymer 5' or branched organic/multimetallic hybrid polymer 6' according to an embodiment of the present invention may be configured so that a reaction time of the organometal ligand and the transition metal compound is equal to or more than 6 hours. As a result, it is possible to synthesize an organic/multimetallic hybrid polymer exhibiting electrochromic properties in the infrared light region and high repetition stability with high yield.

A film 1' of a linear organic/multimetallic hybrid polymer or film 2' of a branched organic/multimetallic hybrid polymer according to an embodiment of the present invention is configured to include the linear organic/multimetallic hybrid polymer 5' or branched organic/multimetallic hybrid polymer 6'. For this reason, it is possible to form a film exhibiting electrochromic properties in the infrared light region and high repetition stability. As a result, it can be applied to an optical device capable of light blocking by switching ON/OFF at two wavelengths within the near infrared to infrared region.

The film 1' of a linear organic/multimetallic hybrid polymer or film 2' of a branched organic/multimetallic hybrid polymer according to an embodiment of the present invention may be configured so that the film thickness is at least 100 nm and not more than 1 mm. As a result, it is possible to form a film exhibiting electrochromic properties in the infrared light region and high repetition stability. As a result, it can be applied to an optical device capable of light blocking by switching ON/OFF at two wavelengths within the near infrared to infrared region.

EXAMPLES

An organic/heterometallic hybrid polymer, a method for producing the same, and an organic/heterometallic hybrid polymer film according to embodiments of the present invention are not limited to the above embodiments, and can be implemented with various modifications within the technical scope of the present invention. Specific examples of the present invention are shown in the following Examples. However, the present invention is not limited to these Examples.

An organic/multimetallic hybrid polymer, a method for producing the same, and an organic/multimetallic hybrid polymer film according to embodiments of the present invention are not limited to the above embodiments, and can be implemented with various modifications within the technical scope of the present invention. Specific examples of the present invention are shown in the following Examples. However, the present invention is not limited to these Examples.

Example 1

First, a terpyridine compound having an ethynyl group and a terpyridyl group (4'-(4-ethynylphenyl)-2,2':6',2"-terpyridine) (100 mg) and Ru(dppe)$_2$Cl(OTf) (153.6 mg) were stirred for 24 hours at room temperature in methylene chloride (20 mL) in the presence of sodium hexafluorophosphate (126 mg) and triethylamine (110 μL). After completion of the reaction, the resultant was filtered, and the resulting filtrate was concentrated. Then, the resulting solid was washed with diethyl ether and then purified by column chromatography on alumina to synthesize an organometal complex 10 having a terpyridyl group at the terminal (283 mg, yield: 55.5%).

Then, $^1$H- and $^{13}$C-NMR, and MS spectra measurements were performed to confirm the structure of the organometal complex 10.

Then, a methanol solution obtained by dispersing 0.1 equivalents of Fe(BF$_4$)$_2$ was added to a 10 μM chloroform solution of the organometal complex 10 in a stepwise manner to carry out a titration test of the organometal complex 10 in the ultraviolet and visible absorption spectrum.

Figure 5:
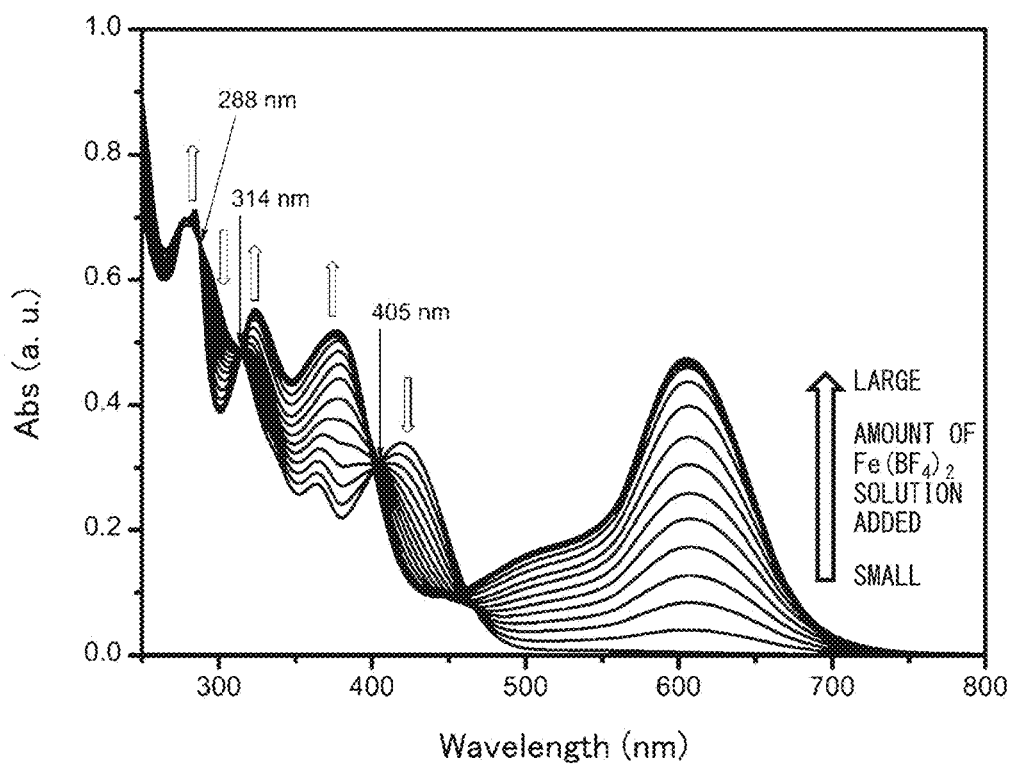
FIG. 5 is a graph showing the titration test result in the ultraviolet and visible absorption spectrum.

FIG. 5 is a graph showing the titration test result in the ultraviolet and visible absorption spectrum. Further, FIG. 6 is a graph showing the relationship between the absorbance change at 605 nm and the added amount in FIG. 5.

Figure 6:
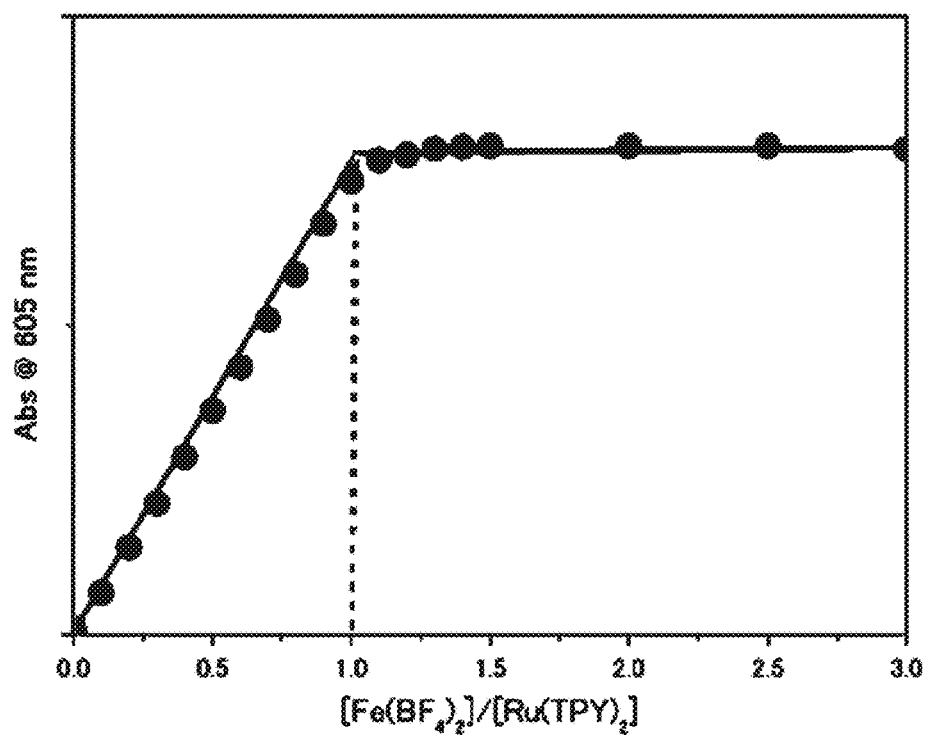
FIG. 6 is a graph showing the relationship between the optical absorption change at 605 nm and the added amount.

As shown in FIGS. 5 and 6, when Fe(BF$_4$)$_2$ was added to the organometal complex 10, characteristic metal-to-ligand charge transfer (MLCT) absorption appeared in the vicinity of 605 nm, and the absorbance increased as the amount added increased and the absorbance became constant when the amount reached 1.0 equivalent or more.

The titration test results in the ultraviolet and visible absorption spectrum indicated that the organometal complex 10 formed a complex with 1.0 equivalent of a transition metal, thereby forming an organic/heterometallic hybrid polymer (polyRuFe).

A methanol solution obtained by dispersing 1.0 molar equivalent of Fe(BF$_4$)$_2$ was added to the chloroform solution of the organometal complex 10 in a stepwise manner, and the resulting mixture was stirred for 12 hours under reflux at about 60° C., thereby obtaining an organic/heterometallic hybrid polymer (polyRuFe) with an yield of 94%.

The obtained polyRuFe dissolved in dimethyl sulfoxide, dimethylformamide, acetonitrile and methylene chloride.

Example 2

An organic/heterometallic hybrid polymer (polyRuRu) was obtained in the same manner as in Example 1 at a yield of 92%, with the exception that 1.0 molar equivalent of RuCl$_2$ was added to an ethylene glycol solution of the organometal complex 10, and the resulting mixture was stirred for 24 hours at 120° C.

The obtained polyRuRu dissolved in dimethyl sulfoxide, dimethylformamide, acetonitrile and methylene chloride.

Example 3

An organic/heterometallic hybrid polymer (polyRuZn) was obtained in the same manner as in Example 1 at a yield of 92%, with the exception that 1.0 molar equivalent of Zn(NTf$_2$)$_2$ was added to an NMP (N-Methyl-pyrrolidone) solution of the organometal complex 10, and the resulting mixture was stirred for 24 hours at 100° C. The obtained polyRuZn was dissolved in dimethyl sulfoxide and dimethylformamide, but was insoluble in acetonitrile and methylene chloride.

<NMR Measurement>

The structure of polyRuZn was confirmed by $^1$H-NMR spectrum.

Figure 7:
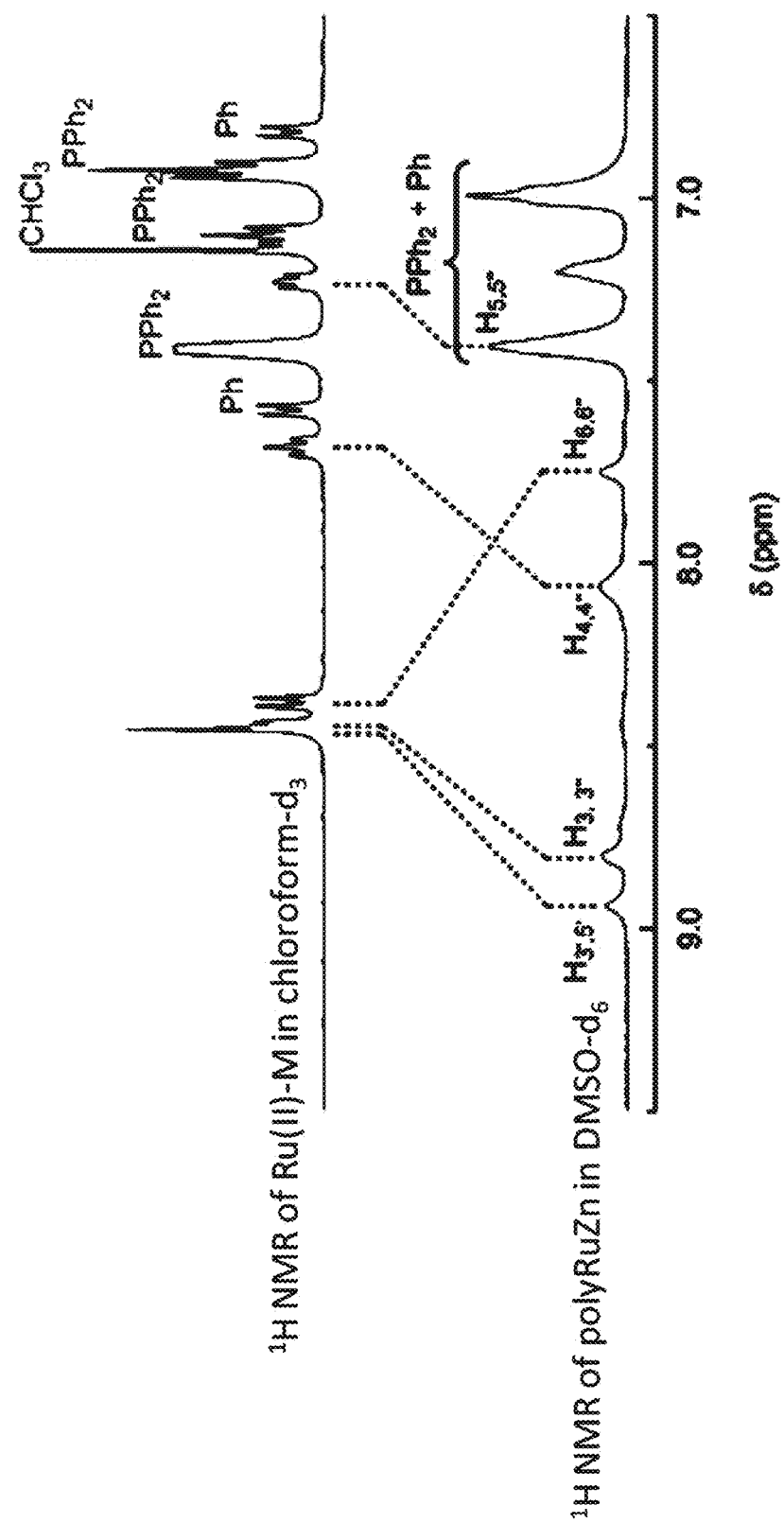
FIG. 7 is a diagram comparing the $^1$H-NMR measurement result of Ru(II)-M (organometal complex 10) in chloroform and the $^1$H-NMR measurement result of polyRuZn in dimethyl sulfoxide.

FIG. 7 is a diagram comparing the $^1$H-NMR spectrum of the organometal complex 10 (here, represented as Ru(II)-M) in chloroform and the $^1$H-NMR spectrum of polyRuZn in dimethyl sulfoxide.

It became apparent from the upfield shift of the proton at 6,6" position of the terpyridyl group and the downfield shift of other protons of the terpyridine that Zn and terpyridine formed a complex, and it became clear that an organic/heterometallic hybrid polymer had been synthesized.

<SEC-RALLS-Viscometry>

The molecular weight of each polymer was calculated by the SEC-RALLS-Viscometry method.

Figure 8:
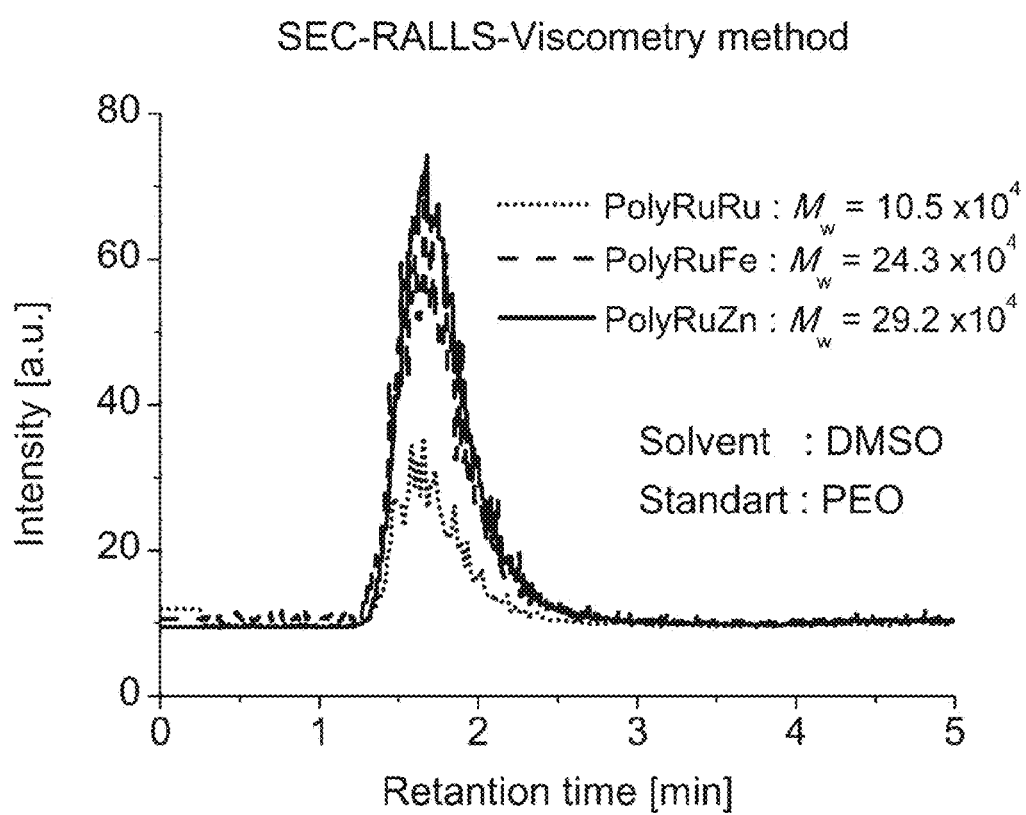
FIG. 8 is a graph showing a measurement result of SEC-RALLS-Viscometry.

FIG. 8 shows a measurement result of SEC-RALLS-Viscometry.

The molecular weight $M_W$ of the polymer was $10.5 \times 10^4$ for polyRuRu, $24.3 \times 10^4$ for polyRuFe, and $29.2 \times 10^4$ for polyRuZn, respectively.

<Electrochemical Properties of Solution>

Each organic/heterometallic hybrid polymer solution was prepared, and the cyclic voltammetry (CV) measurement and differential pulse voltammetry (DPV) measurement were conducted.

The measurement conditions were set as follows: working electrode: Pt mesh electrode; counter electrode: Pt wire electrode; reference electrode: Ag/Ag$^+$; in a 0.1 M dimethylformamide solution of tetrabutylammonium perchlorate (TBAP). The solution was saturated with nitrogen before measurement. The scan rate was 100 mVs$^{-1}$.

Figure 9A:
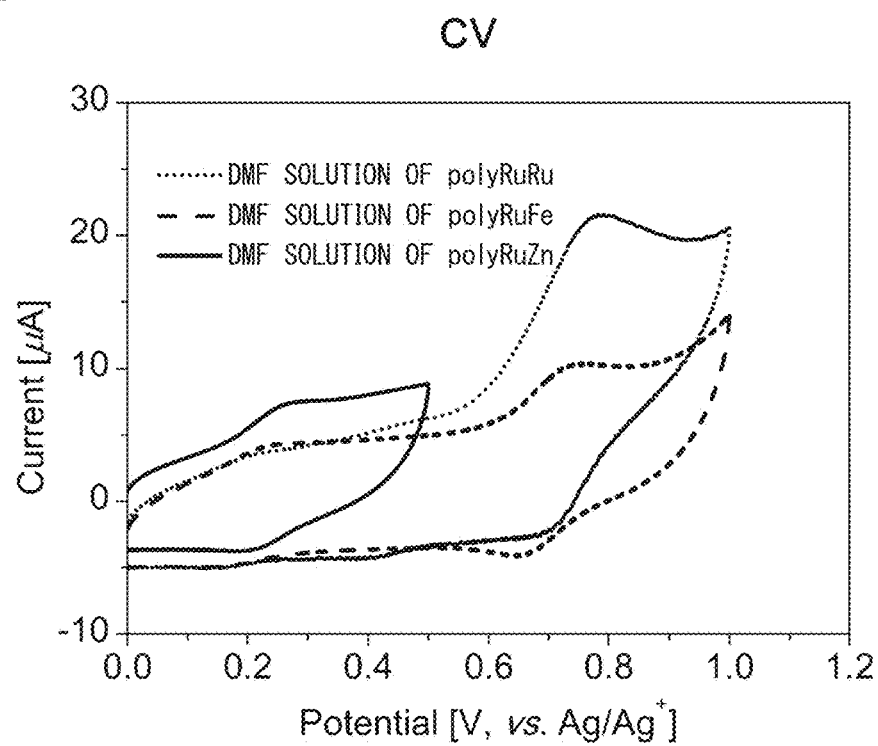
FIG. 9A is a graph showing an electrochemical measurement result in a solution state by the cyclic voltammetry (CV) measurement.
Figure 9B:
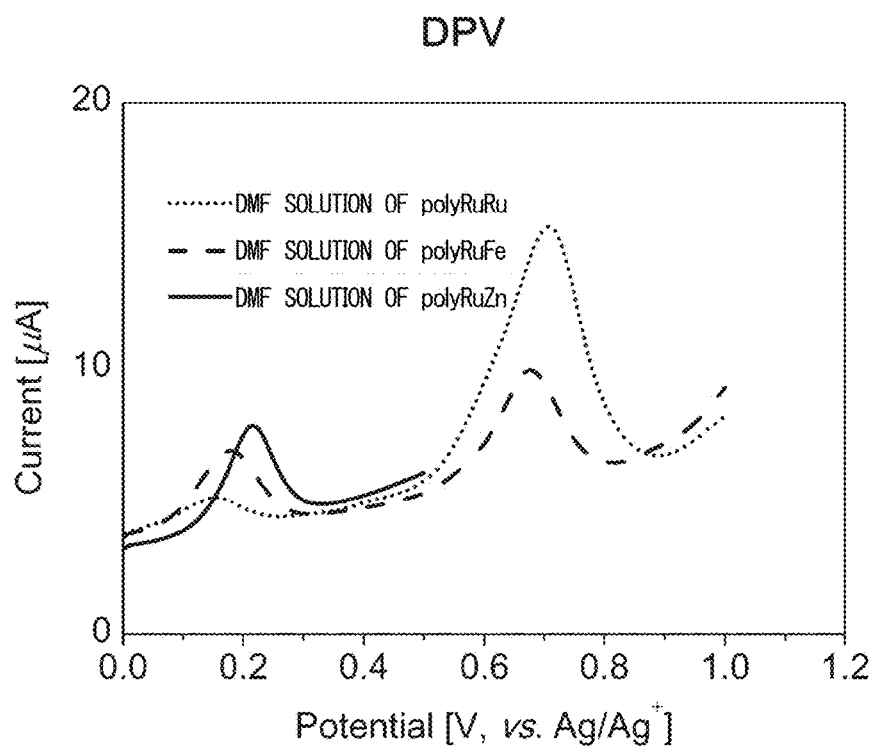
FIG. 9B is a graph showing an electrochemical measurement results in a solution state by the differential pulse voltammetry (DPV) measurement.

FIG. 9A is a graph showing an electrochemical measurement result in a solution state by the CV measurement. FIG. 9B is a graph showing an electrochemical measurement results in a solution state by the DPV measurement.

Each polymer exhibited a reversible oxidation-reduction wave of Ru in the organometal complex 10 around 0.25 V. Moreover, polyRuRu showed a reversible oxidation-reduction wave of Ru forming a complex with the terpyridine site at 0.72 V. Similarly, polyRuFe showed a reversible oxidation-reduction wave of Fe forming a complex with the terpyridine site at 0.70 V.

Next, the solution before and after the voltage application was placed in a quartz cell having a thickness of 1 mm, and UV/visible/near infrared absorption spectrum of the solution were measured while applying a voltage.

Figure 10A:
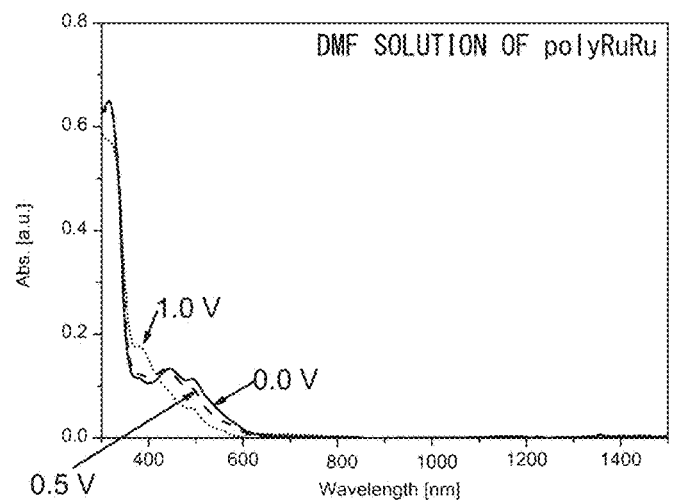
FIG. 10A is a graph showing the applied voltage dependence of the ultraviolet/visible/near infrared absorption spectrum of polyRuRu in a solution state.
Figure 10B:
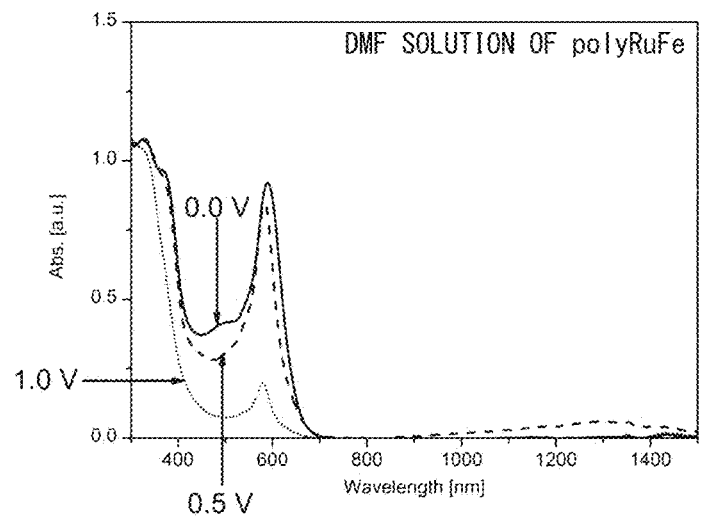
FIG. 10B is a graph showing the applied voltage dependence of the ultraviolet/visible/near infrared absorption spectrum of polyRuFe in a solution state.
Figure 10C:
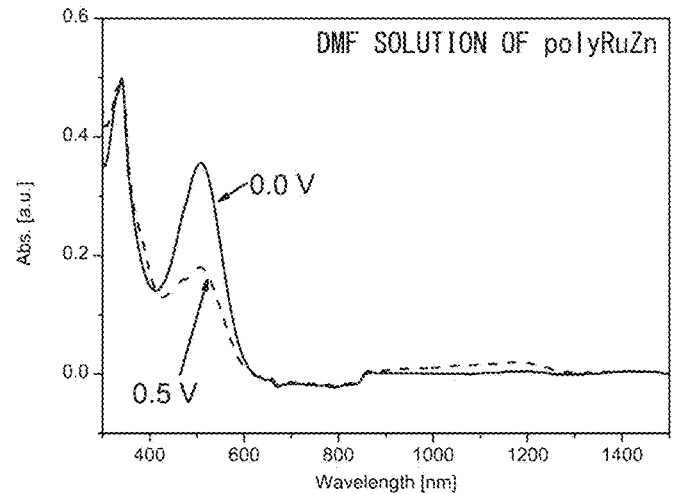
FIG. 10C is a graph showing the applied voltage dependence of the ultraviolet/visible/near infrared absorption spectrum of polyRuZn in a solution state.

FIG. 10A is a graph showing the applied voltage dependence of the ultraviolet/visible/near infrared absorption spectrum of polyRuRu in a solution state. FIG. 10B is a graph showing the applied voltage dependence of the ultraviolet/visible/near infrared absorption spectrum of polyRuFe in a solution state. FIG. 10C is a graph showing the applied voltage dependence of the ultraviolet/visible/near infrared absorption spectrum of polyRuZn in a solution state.

In polyRuFe and polyRuZn, the absorption was observed in the near infrared region when a voltage of 0.5 V was applied. In polyRuFe, the absorption in the near infrared region disappeared when the voltage value was further increased and a voltage of 1.0 V was applied. The electrochromism phenomenon in the near infrared region is presumed to be caused due to the absorption by the intervalence charge transfer (IVCT) between Ru(III)/Fe(II) and Ru(III)/Zn(II) by the oxidation reaction of Ru. In polyRuFe and polyRuZn, the electrochromism phenomenon in the near infrared region appeared more than 30 times in a reversible manner.

On the other hand, in polyRuRu, the electrochromism phenomenon in the near infrared region could not be observed.

<Electrochemical Properties of Thin Film>

Then, 2.5 mg of a dimethylformamide solution of an organic/heterometallic hybrid polymer (polyRuRu) was prepared, and by using this, a thin film of the organic/heterometallic hybrid polymer (polyRuRu) was formed on an ITO glass by the solvent casting method. The film thickness was 25 μm.

Next, a wire was connected to an ITO film (transparent electrode film) to produce a polyRuRu working electrode.

Figure 11:
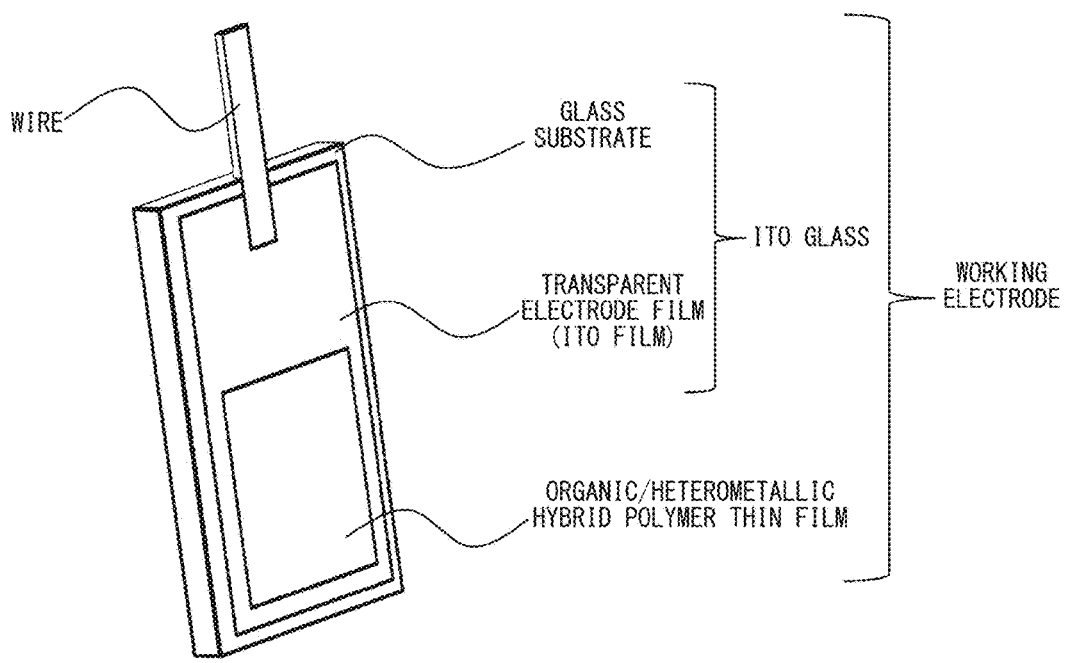
FIG. 11 is a perspective view showing an example of a working electrode.

FIG. 11 is a perspective view showing an example of the working electrode.

A polyRuFe working electrode and a polyRuZn working electrode were prepared in the same manner, with the exception that the type of the organic/heterometallic hybrid polymer was changed.

Next, cyclic voltammetry (CV) and spectroelectrochemical measurements were carried out in a film state.

The measurement conditions were set as follows: working electrode: ITO glass+organic/heterometallic hybrid polymer thin film; counter electrode: ITO glass; reference electrode: Ag/Ag$^+$; in a 0.1 M acetonitrile solution of tetrabutylammonium perchlorate (TBAP).

Figure 12A:
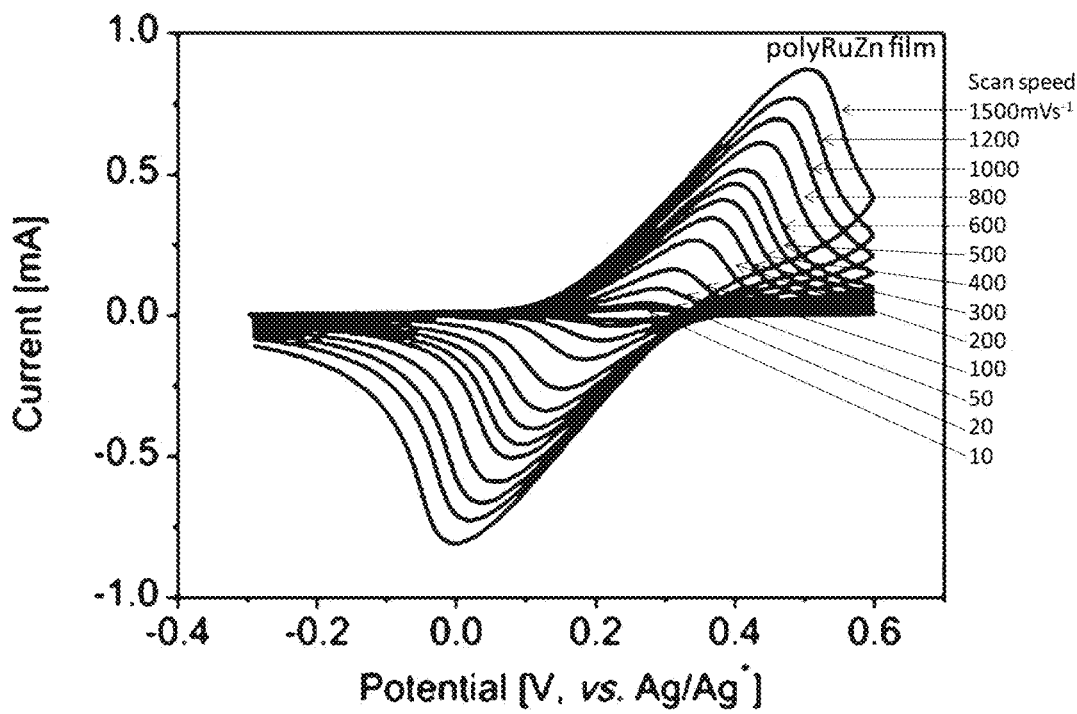
FIG. 12A is a graph showing the scan rate dependence of the CV measurement result of a polyRuZn film which is a graph showing measurement data.
Figure 12B:
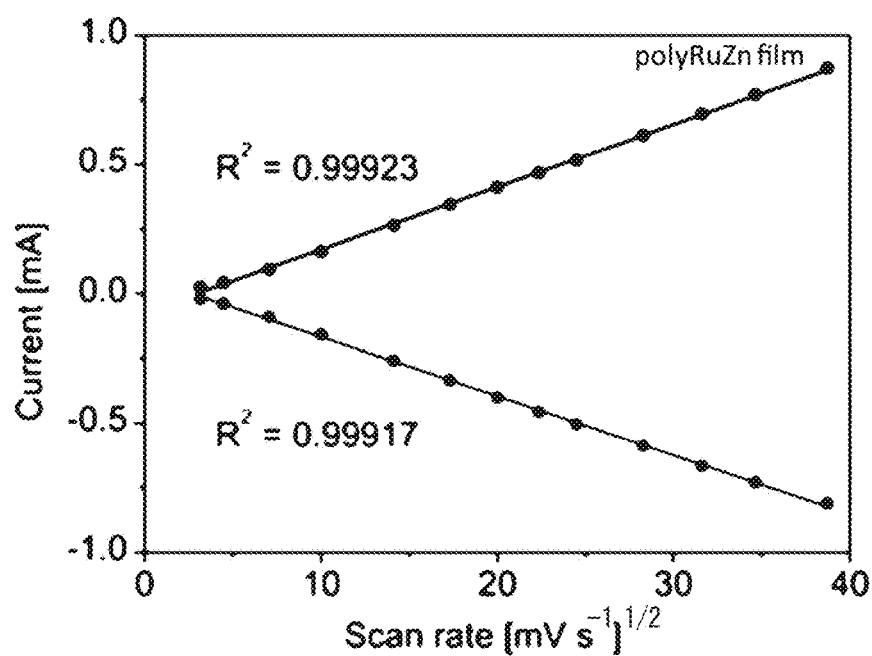
FIG. 12B is a graph showing the scan rate dependence of the CV measurement result of a polyRuZn film which is a graph showing the relationship between the scan rate and the current value.

FIG. 12A is a graph showing measurement data of the scan rate dependence of the CV measurement result of the polyRuZn film. FIG. 12B is a graph showing the relationship between the scan rate and the current value.

The scan rate was set to 10, 20, 50, 100, 200, 300, 400, 500, 600, 800, 1,000, 1,200 or 1,500 mVs$^{-1}$. As the rate increased, the value of the flowing current increased.

The current value showed a first order linear dependence on the one-half power of the scan rate. As a result, it became clear that the electron transfer in this system is not limited by the electron transfer between the polymer and the electrodes, but is controlled by the diffusion limitation due to the process in which negative ions in the solution come into contact with Ru(II) in the polymer.

Then, spectroelectrochemical measurements of polyRuZn in a film state were carried out.

Figure 13:
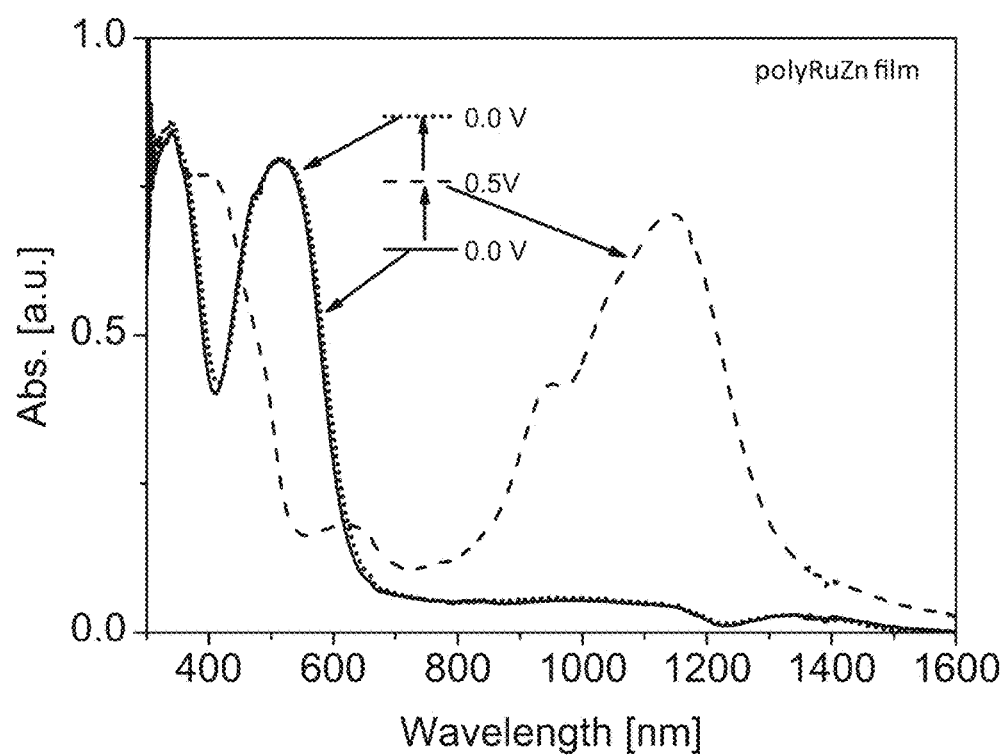
FIG. 13 is a graph showing an electric spectroscopy measurement result of polyRuZn in a film state, which shows the change in absorbance (Abs) before and after the voltage application.

FIG. 13 is a graph showing the electrical spectroscopy measurement result of polyRuZn in the film state, which shows the change in absorbance (Abs) before and after the application of a voltage. With the application of 0 V and 0.01 V, an absorption in the vicinity of 350 nm and an absorption in the vicinity of 510 nm were observed, although almost no absorption appeared in the vicinity of 1,147 nm. On the other hand, when a voltage of 0.5 V was applied, the absorption at 510 nm reduced, and the absorption at 1,147 nm increased. A change ΔT in transmittance in the near infrared region during application of 0 V and 0.5 V was equal to or greater than 60%.

Figure 14:
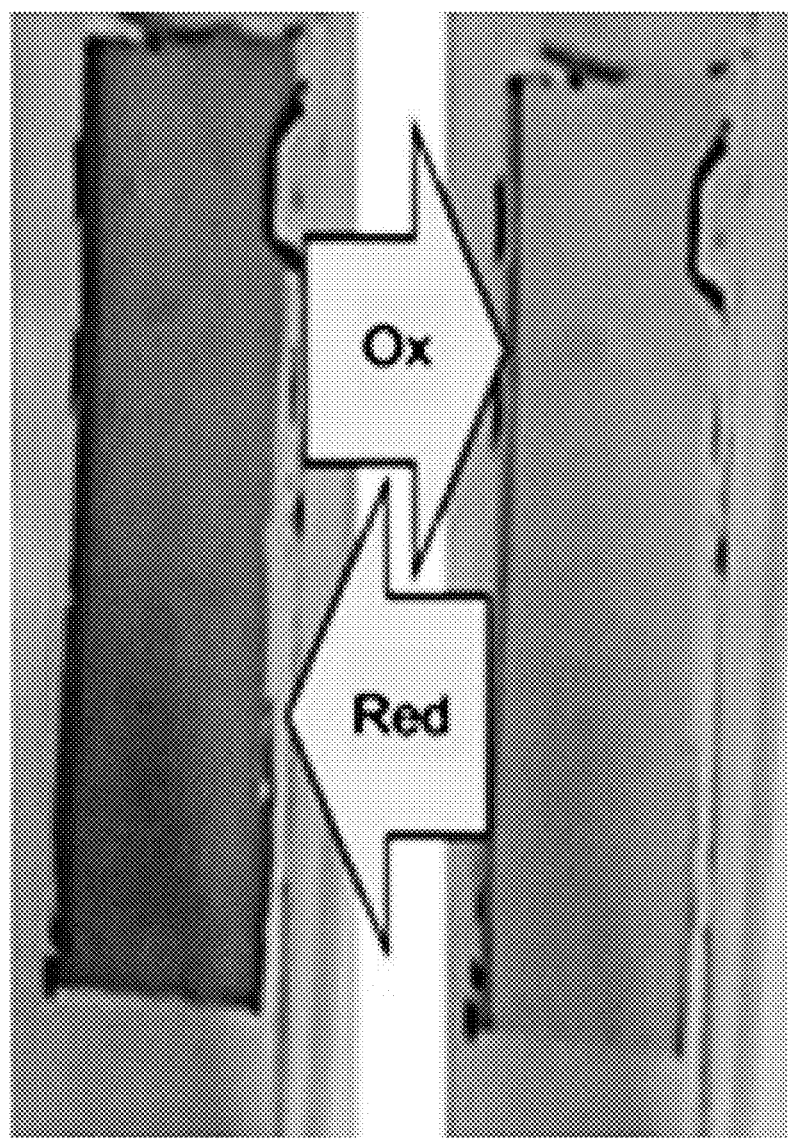
FIG. 14 is a photograph showing the outer appearance of polyRuZn in a film state at the time when no voltage was applied (0 V) and when a voltage of 0.5 V was applied.

FIG. 14 is a photograph showing the outer appearance of polyRuZn in the film state at the time when no voltage was applied (0 V) and when a voltage of 0.5 V was applied. The film had a transparent red purple color when no voltage was applied (0 V), whereas the film had a transparent thin yellow color when a voltage of 0.5 V was applied.

<Reproducibility Test>

Then, by repeatedly applying voltages of 0.5 V and 0.01 V alternately at 5 second intervals to the organic/heterometallic hybrid polymer (polyRuZn), a change in the light absorption at 1,147 nm was observed.

Figure 15A:
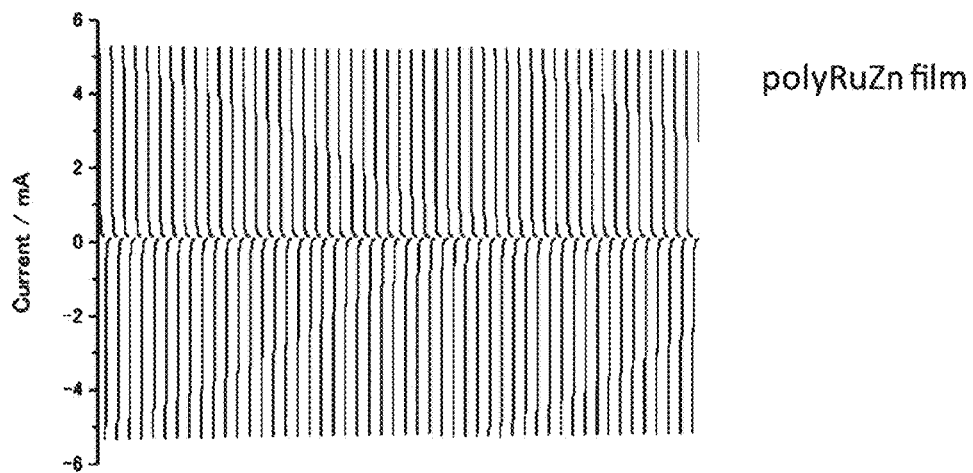
FIG. 15A is a graph showing a change in the physical property values of polyRuZn in a film state due to the on/off of a voltage, which is a change in the current value due to the on/off of a voltage.
Figure 15B:
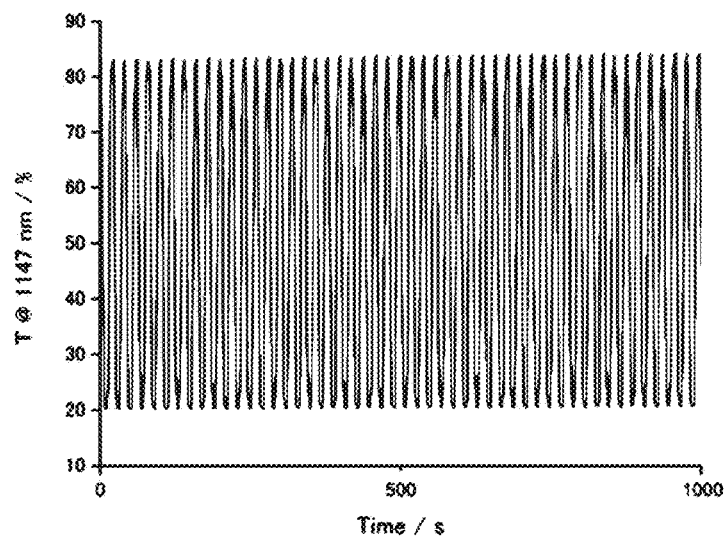
FIG. 15B is a graph showing a change in the physical property values of polyRuZn in a film state due to the on/off of a voltage, which is a change in the light transmittance at a wavelength of 1,147 nm.

FIG. 15A is a graph showing a change in the physical property values of polyRuZn in a film state due to the on/off of a voltage, which is a change in the current value due to the on/off of a voltage. FIG. 15B shows a change in the light transmittance at a wavelength of 1,147 nm. The transmittance changed in response to the current value. The change in the current value and the change in the light transmittance at a wavelength of 1,147 nm corresponded with high reproducibility.

Figure 16:
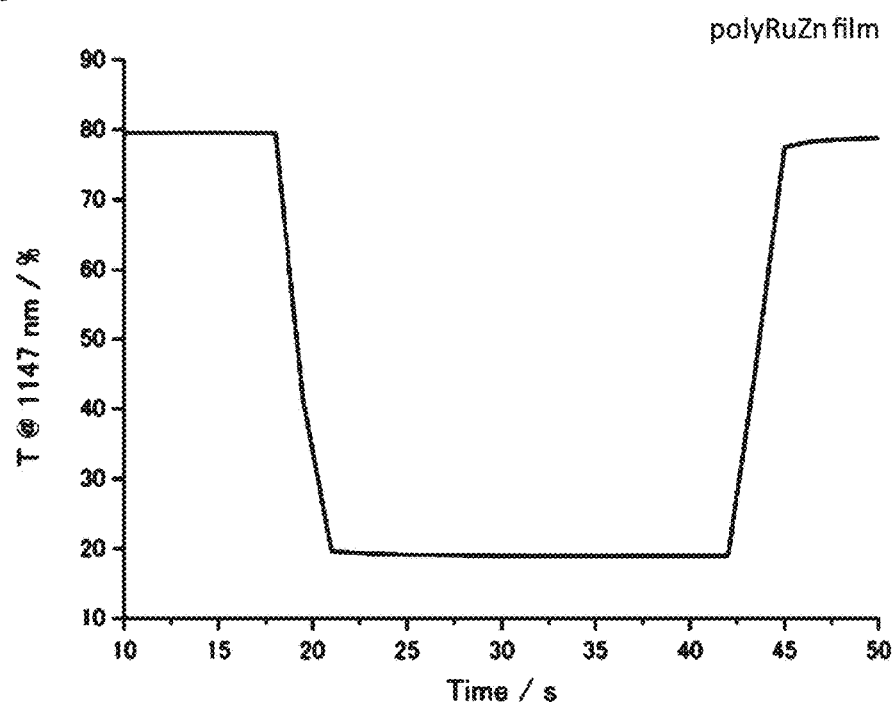
FIG. 16 is a graph showing a change in the light transmittance of polyRuZn in a film state at a wavelength of 1,147 nm due to the on/off of a voltage, when intervals for changing the voltage between 0 V and 0.5 V are set to 20 seconds.

FIG. 16 is a graph showing a change in the light transmittance of polyRuZn in a film state at a wavelength of 1,147 nm due to the on/off of a voltage, when intervals for changing the voltage between 0 V and 0.5 V are set to 20 seconds. The transmittance changed from 80% to 20% at a high speed of about 3 seconds, and the change from 20% to 89% also occurred at a comparably high speed.

Figure 17:
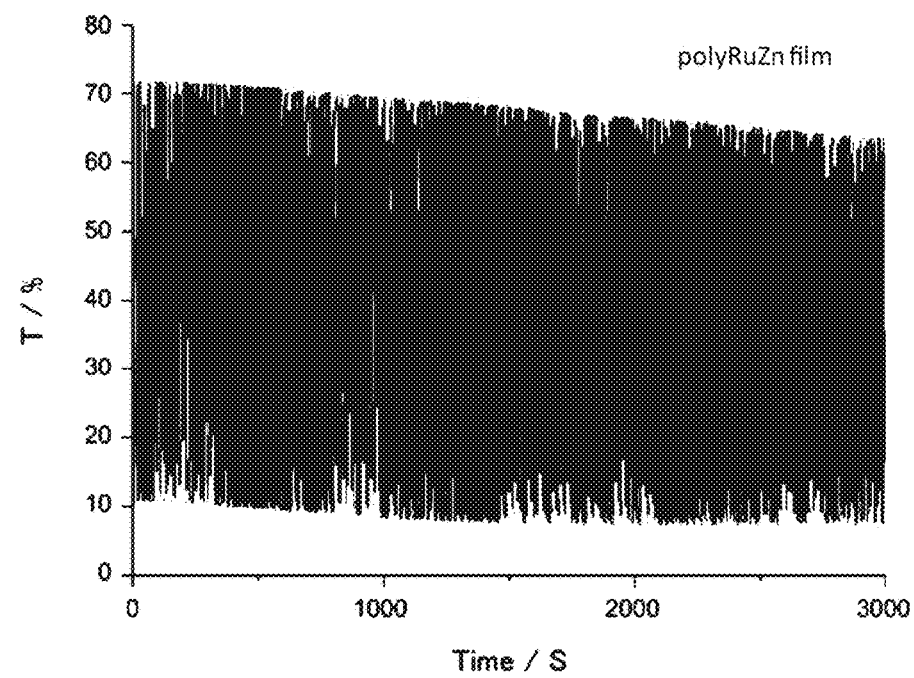
FIG. 17 is a graph showing a change in the transmittance when the voltage was changed 600 times between 0 V and 0.5 V during 3,000 s, for an organic/heterometallic hybrid polymer (polyRuZn) film.

FIG. 17 is a graph showing a change in the transmittance when the voltage was changed 600 times between 0 V and 0.5 V during 3,000 s, for a film of an organic/heterometallic hybrid polymer (polyRuZn). The change in the transmittance was reversible and stable, and the transmittance (absolute value) gradually attenuated. However, the change ΔT in the transmittance was substantially constant, and the change ΔT in the transmittance in the near infrared (NIR) region was equal to or more than 60% even after 3,000 seconds.

Example 4

[ClRu(dppe)$_2$=C=CH—C$_6$H$_4$—HC=C=(dppe)$_2$RuCl](OTf)$_2$ (binuclear organometallic site) which was a salt of Ru(II)(dppe)$_2$=C=CH—C$_6$H$_4$—HC=C=Ru(dppe)$_2$Cl$_2$ was synthesized according to the following previous report.

Benameur, A.; Brignou, P.; Di Piazza, E.; Hervault, Y.-M.; Norel, L.; Rigaut, S., New J. Chem. 2011, 35 (10), 2105-2113.

A terpyridine compound having an ethynyl group and a terpyridyl group (4'-(4-ethynylphenyl)-2,2':6',2''-terpyridine) (308.2 mg) and [ClRu(dppe)$_2$=C=CH—C$_6$H$_4$—

HC≡C–(dppe)$_2$RuCl](OTf)$_2$ (708.7 mg) were stirred at room temperature under a nitrogen atmosphere for 7 days in methylene chloride (80 mL) in the presence of triethylamine (1.85 mL) and sodium hexafluorophosphate (206.5 mg). Thereafter, diethyl ether was added thereto, and after filtering the precipitates, the resultant was washed with diethyl ether. The resultant was purified by column chromatography on alumina to isolate an organometal ligand having a terpyridyl group at the terminal (L-Ru(II)$_2$-L) as a yellow solid (744 mg, yield: 80.8%).

$^1$H- and $^{31}$P-NMR, and high-resolution mass spectrum (HRMS) measurement were performed to confirm the structure of the organometal ligand (L-Ru(II)$_2$-L).

Then, under an argon atmosphere, an NMP (N-Methylpyrrolidone) solution obtained by dispersing an equimolar amount of Zn(NTf$_2$)$_2$ was added to an NMP solution of the organometal ligand (L-Ru(II)$_2$-L) in a stepwise manner, and the resulting mixture was stirred for 6 hours under reflux at about 120° C., thereby obtaining a linear organic/multimetallic hybrid polymer (poly(Ru$_2$Zn)$_{100}$) in the form of a dark red solid with an yield of 82%.

The obtained poly(Ru$_2$Zn)$_{100}$ dissolved in dimethylformamide and dimethyl sulfoxide.

Next, the linear organic/multimetallic hybrid polymer was dissolved in dimethyl sulfoxide to produce a solution having a concentration of 0.5 mg/mL, and a film of the linear organic/multimetallic hybrid polymer (poly(Ru$_2$Zn)$_{100}$) was formed on a glass slide by the drop-coating method.

Then, 2.5 mg of the organic/multimetallic hybrid polymer was dissolved in dimethyl sulfoxide to produce a solution having a concentration of 0.5 mg/mL, and a film of the linear organic/multimetallic hybrid polymer (poly(Ru$_2$Zn)$_{100}$) was formed on an ITO glass (active area: 0.8×2.5 cm$^2$) by the drop-coating method, thereby producing a working electrode.

The film thickness was 25 μm.

Example 5

Then, an NMP solution of 3D-M which had been prepared in advance so as to be 10 molar parts with respect to the combined total of 100 molar parts of the linear portion constituting poly(Ru$_2$Zn)$_{100}$ was added to the linear organic/multimetallic hybrid polymer (poly(Ru$_2$Zn)$_{100}$) in the form of a dark red solid.

Next, Zn(NTf$_2$)$_2$ was mixed in an equimolar amount relative to 3D-M, and the resulting mixture was stirred for 18 hours under reflux at about 120° C., precipitated in diethyl ether, and washed with chloroform, water, and diethyl ether, followed by drying, thereby obtaining a branched organic/multimetallic hybrid polymer (poly(Ru$_2$Zn)$_{90}$) in the form of a dark red solid with an yield of 85%.

The obtained poly(Ru$_2$Zn)$_{90}$ dissolved in heated dimethyl sulfoxide. However, it was insoluble in dimethylformamide and dimethyl sulfoxide at room temperature. It was speculated that the heat resistance was improved by the 3D network structure.

Next, the branched organic/multimetallic hybrid polymer was dissolved in dimethyl sulfoxide to produce a solution having a concentration of 0.5 mg/mL, and a film of the branched organic/multimetallic hybrid polymer (poly(Ru$_2$Zn)$_{90}$) was formed on a glass slide by the drop-coating method.

Then, 2.5 mg of the branched organic/multimetallic hybrid polymer was dissolved in dimethyl sulfoxide to produce a solution having a concentration of 0.5 mg/mL, and a film of the branched organic/multimetallic hybrid polymer (poly(Ru$_2$Zn)$_{90}$) was formed on an ITO glass (active area: 0.8×2.5 cm$^2$) by the drop-coating method, thereby producing a working electrode.

The film thickness was 25 μm.

Example 6

Then, an NMP solution of 3D-M which had been prepared in advance so as to be 20 molar parts with respect to the combined total of 100 molar parts of the linear portion constituting poly(Ru$_2$Zn)$_{100}$ was added to the linear organic/multimetallic hybrid polymer (poly(Ru$_2$Zn)$_{100}$) in the form of a dark red solid.

Next, Zn(NTf$_2$)$_2$ was mixed in an equivalent amount relative to 3D-M, and the resulting mixture was stirred for 18 hours under reflux at about 120° C., precipitated in diethyl ether, and washed with chloroform, water, and diethyl ether, followed by drying, thereby obtaining a branched organic/multimetallic hybrid polymer (poly(Ru$_2$Zn)$_{80}$) in the form of a dark red solid with an yield of 80%.

The obtained poly(Ru$_2$Zn)$_{80}$ dissolved in heated dimethyl sulfoxide. However, it was insoluble in dimethylformamide and dimethyl sulfoxide at room temperature. It was speculated that the heat resistance was improved by the 3D network structure.

Next, the branched organic/multimetallic hybrid polymer was dissolved in dimethyl sulfoxide to produce a solution having a concentration of 0.5 mg/mL, and a film of the branched organic/multimetallic hybrid polymer (poly(Ru$_2$Zn)$_{80}$) was formed on a glass slide by the drop-coating method.

Then, 2.5 mg of the branched organic/multimetallic hybrid polymer was dissolved in dimethyl sulfoxide to produce a solution having a concentration of 0.5 mg/mL, and a film of the branched organic/multimetallic hybrid polymer (poly(Ru$_2$Zn)$_{80}$) was formed on an ITO glass (active area: 0.8×2.5 cm$^2$) by the drop-coating method, thereby producing a working electrode.

The film thickness was 25 μm.

Example 7

Then, an NMP solution of 3D-M which had been prepared in advance so as to be 30 molar parts with respect to the combined total of 100 molar parts of the linear portion constituting poly(Ru$_2$Zn)$_{100}$ was added to the linear organic/multimetallic hybrid polymer (poly(Ru$_2$Zn)$_{100}$) in the form of a dark red solid.

Next, Zn(NTf$_2$)$_2$ was mixed in an equivalent amount relative to 3D-M, and the resulting mixture was stirred for 18 hours under reflux at about 120° C., precipitated in diethyl ether, and washed with chloroform, water, and diethyl ether, followed by drying, thereby obtaining a branched organic/multimetallic hybrid polymer (poly(Ru$_2$Zn)$_{70}$) in the form of a dark red solid with a high yield of 81%.

The obtained poly(Ru$_2$Zn)$_{70}$ dissolved in heated dimethyl sulfoxide. However, it was insoluble in dimethylformamide and dimethyl sulfoxide at room temperature. It was speculated that the heat resistance was improved by the 3D network structure.

Next, the branched organic/multimetallic hybrid polymer was dissolved in dimethyl sulfoxide to produce a solution having a concentration of 0.5 mg/mL, and a film of the branched organic/multimetallic hybrid polymer (poly($Ru_2Zn$)$_{70}$) was formed on a glass slide by the drop-coating method.

Then, 2.5 mg of the branched organic/multimetallic hybrid polymer was dissolved in dimethyl sulfoxide to produce a solution having a concentration of 0.5 mg/mL, and a film of the branched organic/multimetallic hybrid polymer (poly($Ru_2Zn$)$_{70}$) was formed on an ITO glass (active area: 0.8×2.5 $cm^2$) by the drop-coating method, thereby producing a working electrode.

The film thickness was 25 μm.

<Thermogravimetric Analysis: TGA Measurement>

Then, TGA measurement was carried out.

Figure 29:
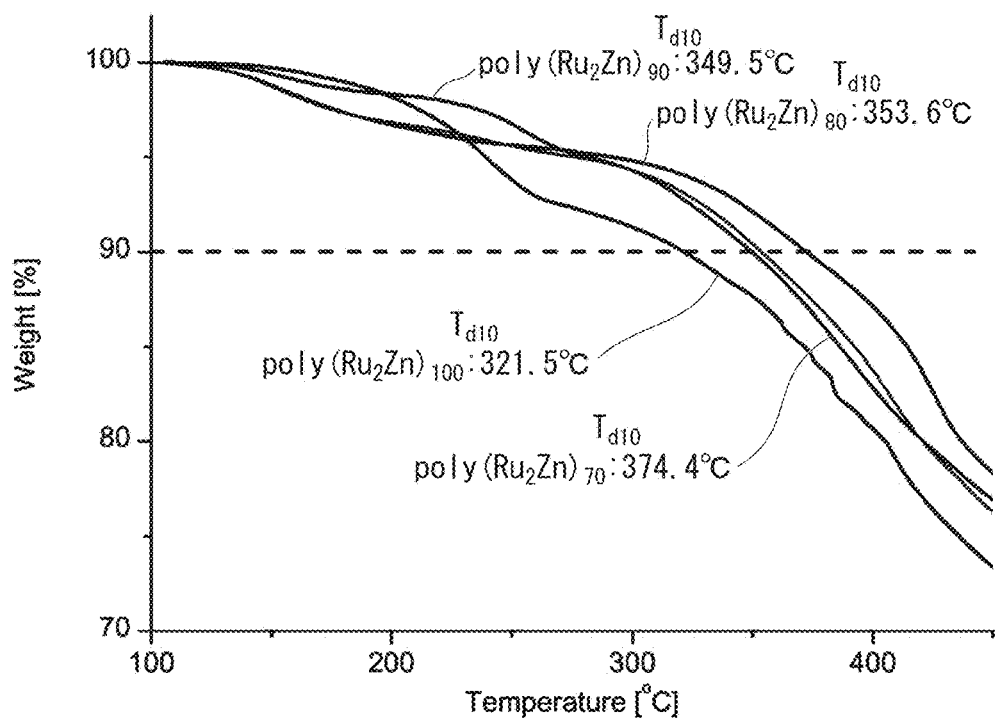
FIG. 29 is a graph showing a TGA measurement result of poly($Ru_2Zn$)$_{100}$, poly($Ru_2Zn$)$_{90}$, poly($Ru_2Zn$)$_{80}$ and poly($Ru_2Zn$)$_{70}$.

FIG. 29 is a graph showing a TGA measurement result of poly($Ru_2Zn$)$_{100}$, poly($Ru_2Zn$)$_{90}$, poly($Ru_2Zn$)$_{80}$ and poly($Ru_2Zn$)$_{70}$.

Mass was reduced in all samples when heated.

$T_{d10}$ is a heating temperature at which the mass is reduced by 10%.

$T_{d10}$ of poly($Ru_2Zn$)$_{100}$ was 321.5° C., which was the lowest.

The $T_{d10}$ values increased as the proportion of Zn increased, and $T_{d10}$ of poly($Ru_2Zn$)$_{70}$ was 372.4° C., which was the highest.

<Atomic Force Microscopy: AFM Observation>

Next, the surface of each organic/multimetallic hybrid polymer film formed on a glass slide was observed by atomic force microscopy (AFM).

Figure 30A:
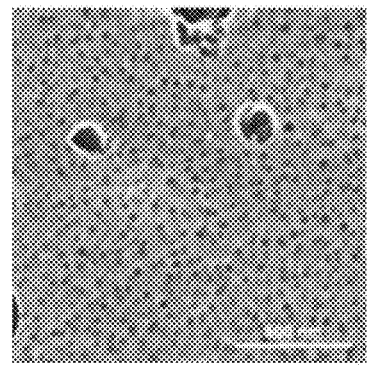
FIG. 30A is an AFM image of a poly($Ru_2Zn$)$_{100}$ film.
Figure 30B:
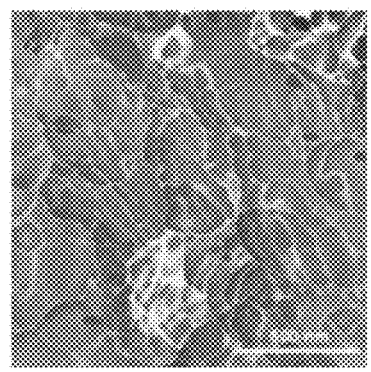
FIG. 30B is an AFM image of a poly($Ru_2Zn$)$_{90}$ film.
Figure 30C:
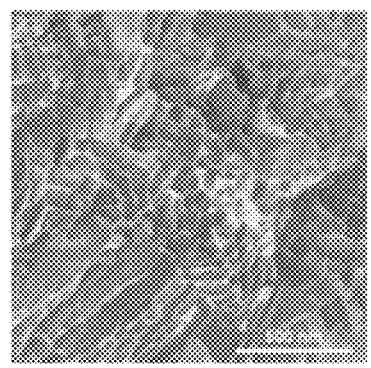
FIG. 30C is an AFM image of a poly($Ru_2Zn$)$_{80}$ film.
Figure 30D:
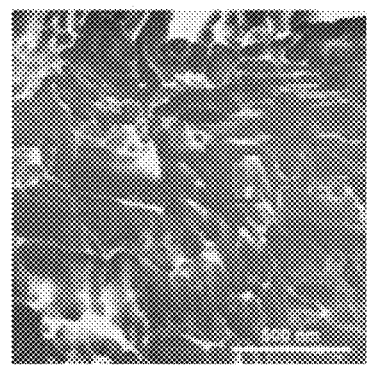
FIG. 30D is an AFM image of a poly($Ru_2Zn$)$_{70}$ film.

FIG. 30A is an AFM image of a poly($Ru_2Zn$)$_{100}$ film. FIG. 30B is an AFM image of a poly($Ru_2Zn$)$_{90}$ film. FIG. 30C is an AFM image of a poly($Ru_2Zn$)$_{80}$ film. FIG. 30D is an AFM image of a poly($Ru_2Zn$)$_{70}$ film.

The poly($Ru_2Zn$)$_{100}$ film was a porous film. The root-mean square roughness ($R_{rms}$) was as small as 1.1 nm.

Films from the poly($Ru_2Zn$)$_{90}$ film to the poly($Ru_2Zn$)$_{70}$ film were completely different from the poly($Ru_2Zn$)$_{100}$ film, and were rough films.

$R_{rms}$ of the poly($Ru_2Zn$)$_{90}$ film was 1.3 nm, $R_{rms}$ of the poly($Ru_2Zn$)$_{80}$ film was 1.4 nm, and $R_{rms}$ of the poly($Ru_2Zn$)$_{70}$ film was 4.3 nm. The poly($Ru_2Zn$)$_{70}$ film was the most porous film.

<Electrochemical Properties of Film>

Next, the cyclic voltammetry (CV) measurement of each of the organic/multimetallic hybrid polymer films formed on the ITO glass was carried out.

The measurement conditions were set as follows: working electrode: poly($Ru_2Zn$)$_{70}$/ITO electrode; counter electrode: ITO electrode; reference electrode: Ag/Ag$^+$; in a 0.1 M $CH_3CN$ solution of $LiClO_4$. The solution was saturated with nitrogen before measurement. The scan rate was 20 $mVs^{-1}$.

Figure 31:
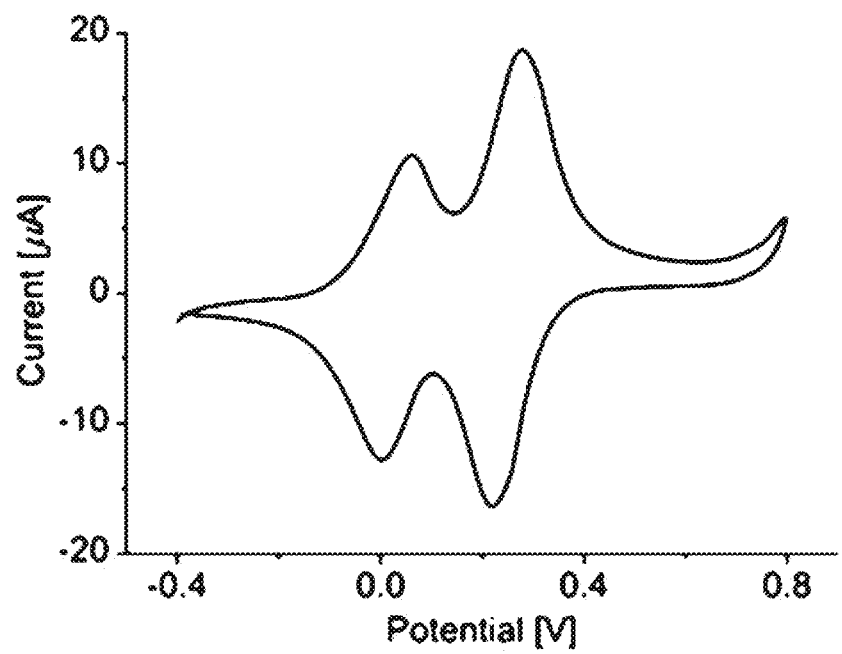
FIG. 31 is a CV spectrum showing an electrochemical measurement result of a poly($Ru_2Zn$)$_{70}$ film.

FIG. 31 is a CV spectrum showing an electrochemical measurement result of the poly($Ru_2Zn$)$_{70}$ film. Reversible peaks were observed at 21 mV and 255 mV. These are due to the oxidation-reduction between Ru(II)/(III) in the Ru-acetylide complex.

A potential ΔE between oxidation peaks was 234 mV, and Kc=exp(ΔEF/RT) was 1.1×10$^4$. This indicates that species in which one side is oxidized is stable. It was presumed to be because electrons were delocalized along the conjugated chain.

Figure 32:
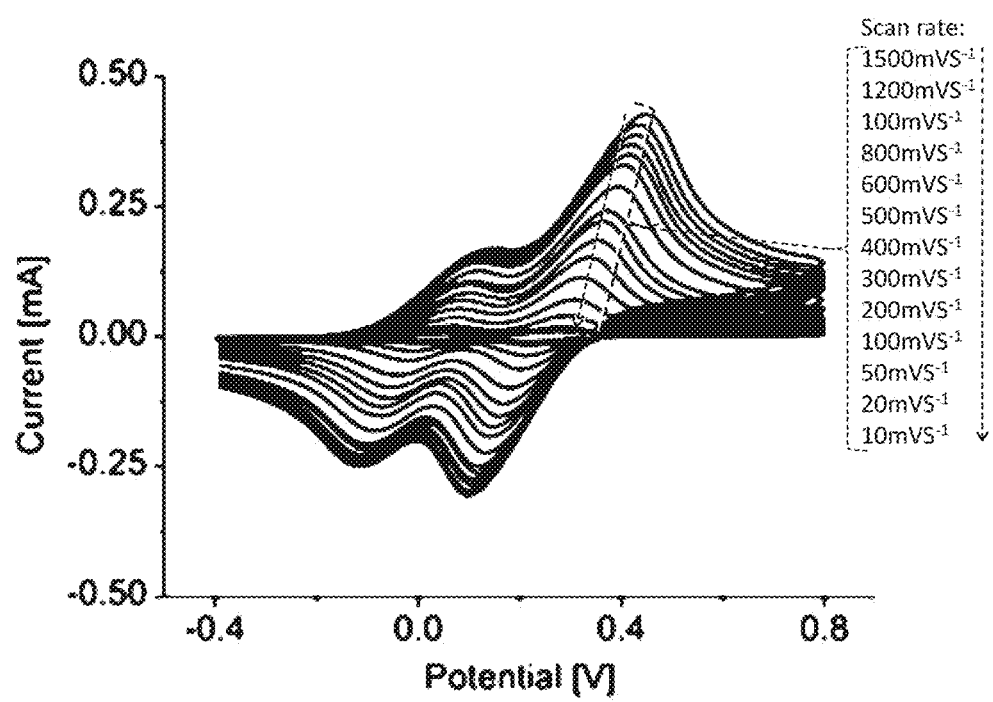
FIG. 32 is a CV spectrum showing the scan rate dependence of a poly($Ru_2Zn$)$_{70}$ film.

FIG. 32 is a CV spectrum showing the scan rate dependence of the poly($Ru_2Zn$)$_{70}$ film.

Cases in which the scan rate was set to 10, 20, 50, 100, 300, 400, 500, 600, 800, 1,000, 1,200 and 1,500 $mVs^{-1}$ are shown.

The peak current value increased as the scan rate increased.

Figure 33:
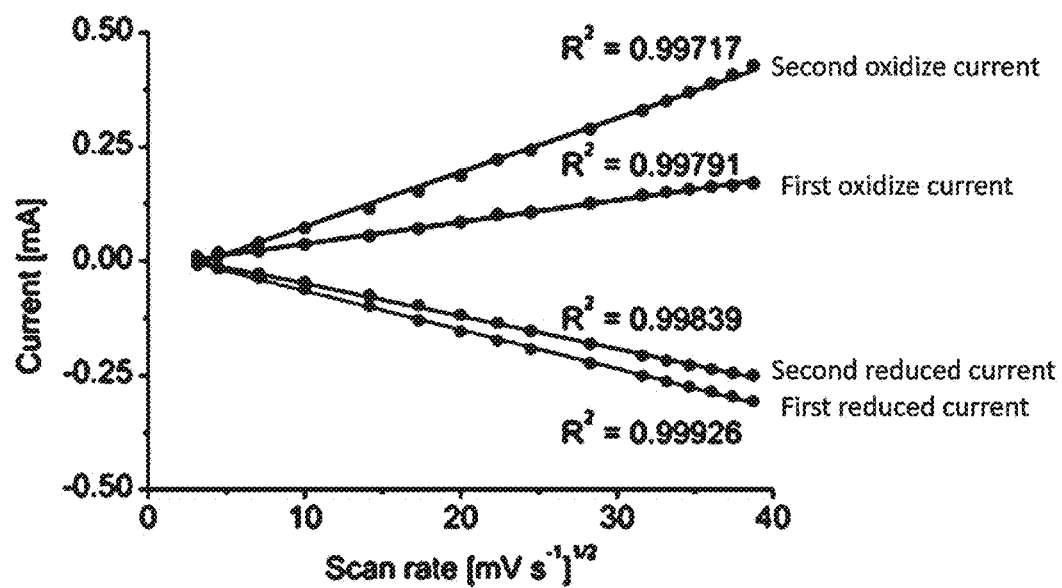
FIG. 33 is a graph showing the relationship between the scan rate and the current value.

FIG. 33 is a graph showing the relationship between the scan rate and the current value.

Each current value of the First oxidize current, Second oxidize current, First reduced current and Second reduced current was obtained from the first order linear relationship with the one-half power of the scan rate. The square root $R^2$ of the scan rate was 0.99791, 0.99717, 0.99926 and 0.99839.

From these results, it could be speculated that the oxidation-reduction reaction of Ru is not limited by the electron transfer between the polymer and the electrodes, but is controlled by the diffusion limitation due to the process in which negative ions in the solution come into contact with Ru(II) in the polymer.

On the other hand, the films of other polymers showed no electrochemical properties. This is because they were readily dissolved in an electrolytic solution containing an electrolyte such as $LiClO_4$.

<Spectroelectrochemical Measurements in the UV/Visible/Near Infrared Region>

Then, spectroelectrochemical measurements of the poly($Ru_2Zn$)$_{100}$ film were carried out.

Figure 34:
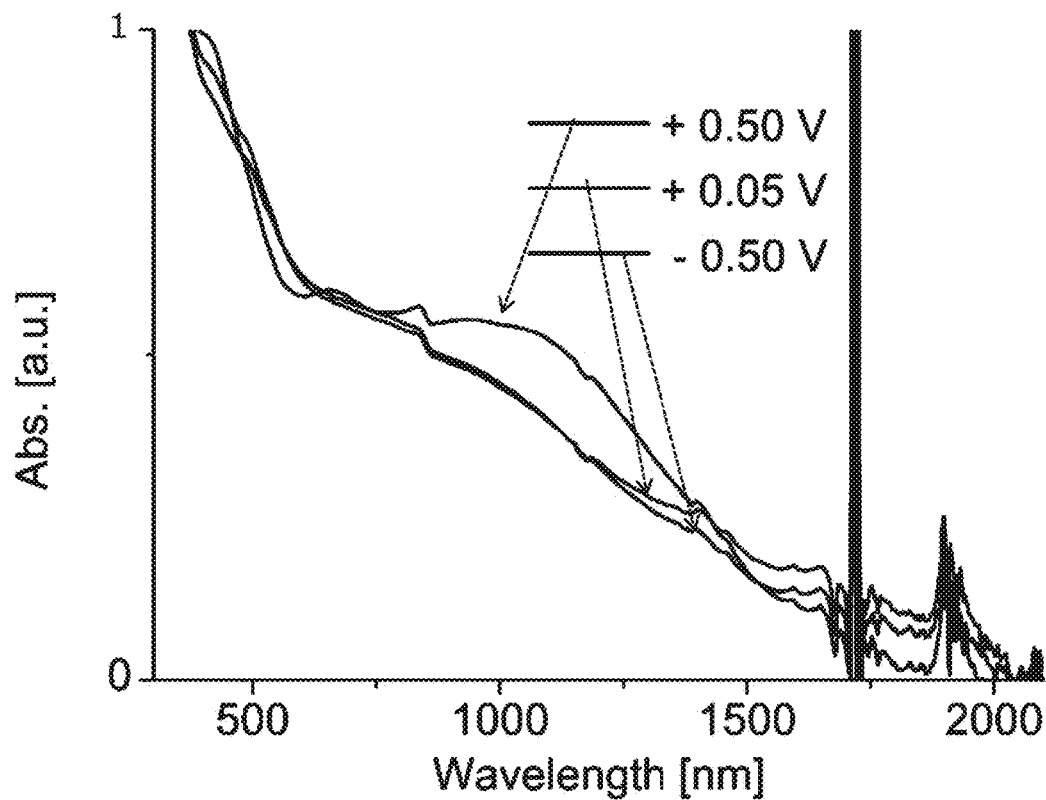
FIG. 34 is a graph showing spectroelectrochemical measurements of a poly($Ru_2Zn$)$_{100}$ film, which shows the change in the ultraviolet/visible/near infrared absorption spectrum before and after the voltage application.

FIG. 34 is a graph showing the spectroelectrochemical measurements of the poly($Ru_2Zn$)$_{100}$ film, which shows the change in the ultraviolet/visible/near infrared absorption spectrum before and after the voltage application. With the application of 0.50 V, an absorption in the vicinity of 1,174 nm was observed, although almost no absorption appeared in the vicinity of 1,844 nm. On the other hand, when voltages of 0.05 V and −0.50 V were applied, the absorption at 1,174 nm reduced, and the absorption at 1,844 nm slightly increased.

Then, spectroelectrochemical measurements of the poly($Ru_2Zn$)$_{90}$ film were carried out.

Figure 35:
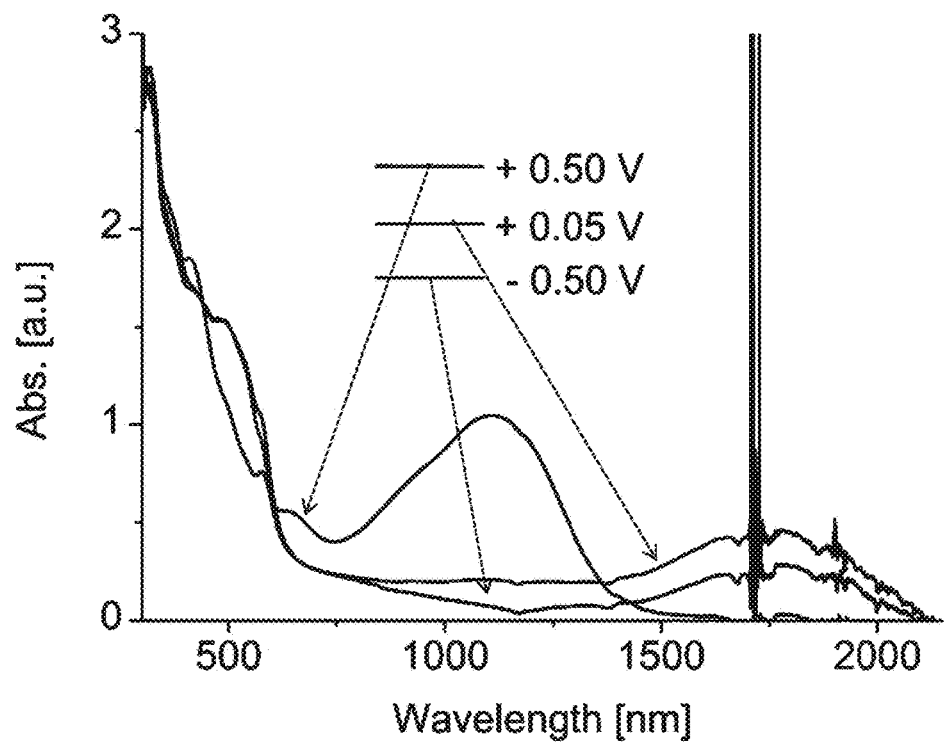
FIG. 35 is a graph showing spectroelectrochemical measurements of a poly($Ru_2Zn$)$_{90}$ film, which shows the change in the ultraviolet/visible/near infrared absorption spectrum before and after the voltage application.

FIG. 35 is a graph showing the spectroelectrochemical measurements of the poly($Ru_2Zn$)$_{90}$ film, which shows the change in the ultraviolet/visible/near infrared absorption spectrum before and after the voltage application. With the application of 0.50 V, an absorption in the vicinity of 1,174 nm was observed, although almost no absorption appeared in the vicinity of 1,844 nm. On the other hand, when a voltage of 0.05 V was applied, the absorption at 1,174 nm reduced, and the absorption at 1,844 nm rose slightly. When a voltage of −0.50 V was applied, the absorption at 1,174 nm greatly reduced, and the absorption at 1,844 nm increased greatly.

Then, spectroelectrochemical measurements of the poly($Ru_2Zn$)$_{70}$ film were carried out.

Figure 36:
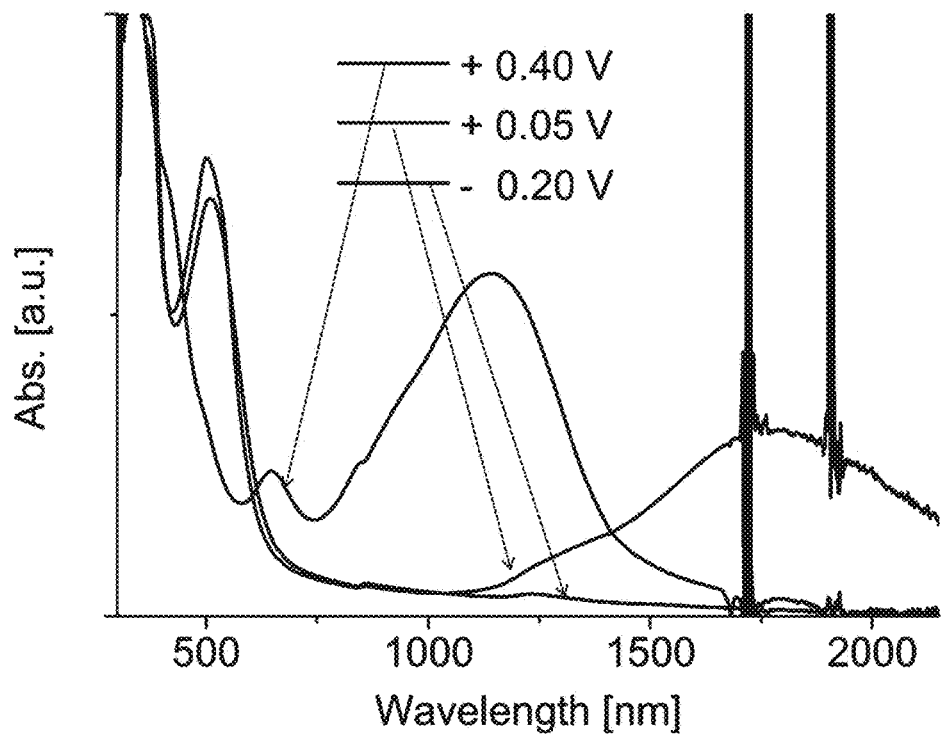
FIG. 36 is a graph showing spectroelectrochemical measurements of a poly($Ru_2Zn$)$_{70}$ film, which shows the change in the ultraviolet/visible/near infrared absorption spectrum before and after the voltage application.

FIG. 36 is a graph showing the spectroelectrochemical measurements of the poly($Ru_2Zn$)$_{70}$ film, which shows the change in the ultraviolet/visible/near infrared absorption spectrum before and after the voltage application. With the application of 0.40 V, an absorption in the vicinity of 1,174 nm was observed, although almost no absorption appeared in the vicinity of 1,844 nm. On the other hand, when a voltage of 0.05 V was applied, the absorption at 1,174 nm reduced, and the absorption at 1,844 nm increased slightly. When a voltage of −0.20 V was applied, the absorption at 1,174 nm greatly reduced, and the absorption at 1,844 nm increased greatly.

<Reproducibility Test>

Then, by repeatedly applying voltages of 0.05 V and 0.4 V alternately at 5 second intervals, 10 second intervals, 15 second intervals and 20 second intervals to the film of the branched organic/multimetallic hybrid polymer (poly($Ru_2Zn$)$_{70}$), a change in the light transmittance at 1,844 nm was observed.

Figure 37:
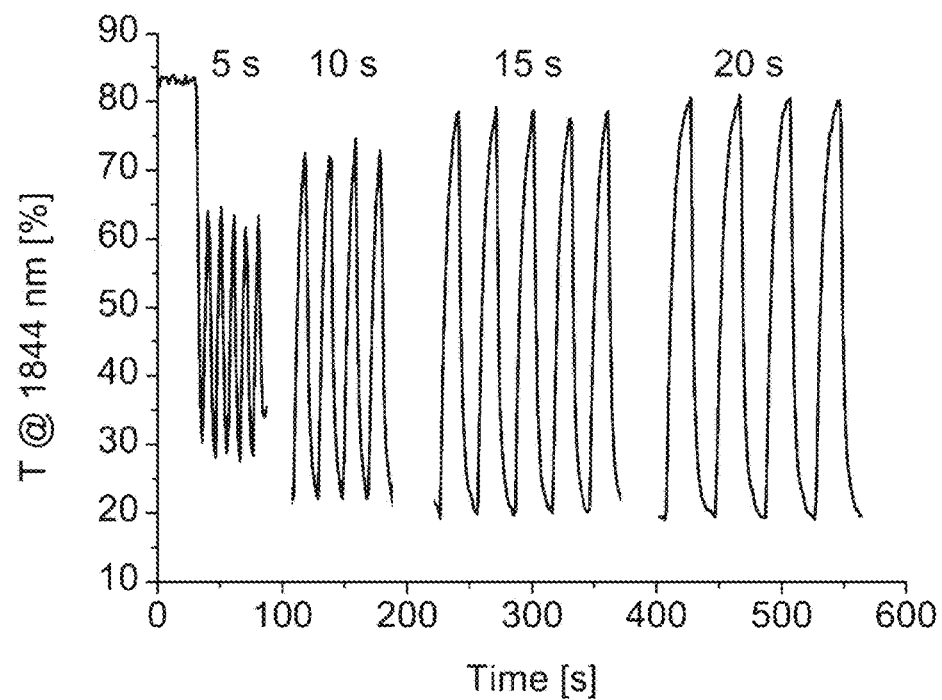
FIG. 37 is a graph showing the application interval dependence of the light transmittance change at 1,844 nm of a poly($Ru_2Zn$)$_{70}$ film due to the on/off of voltage.

FIG. 37 is a graph showing the applied voltage dependence of the light transmittance change at 1,844 nm of the poly(Ru$_2$Zn)$_{70}$ film due to the on/off of voltage.

Then, by repeatedly applying voltages of 0.05 V and −0.2 V alternately 50 times at 20 second intervals to the film of the branched organic/multimetallic hybrid polymer (poly(Ru$_2$Zn)$_{70}$), a change in the light transmittance at 1,844 nm was observed.

Figure 38:
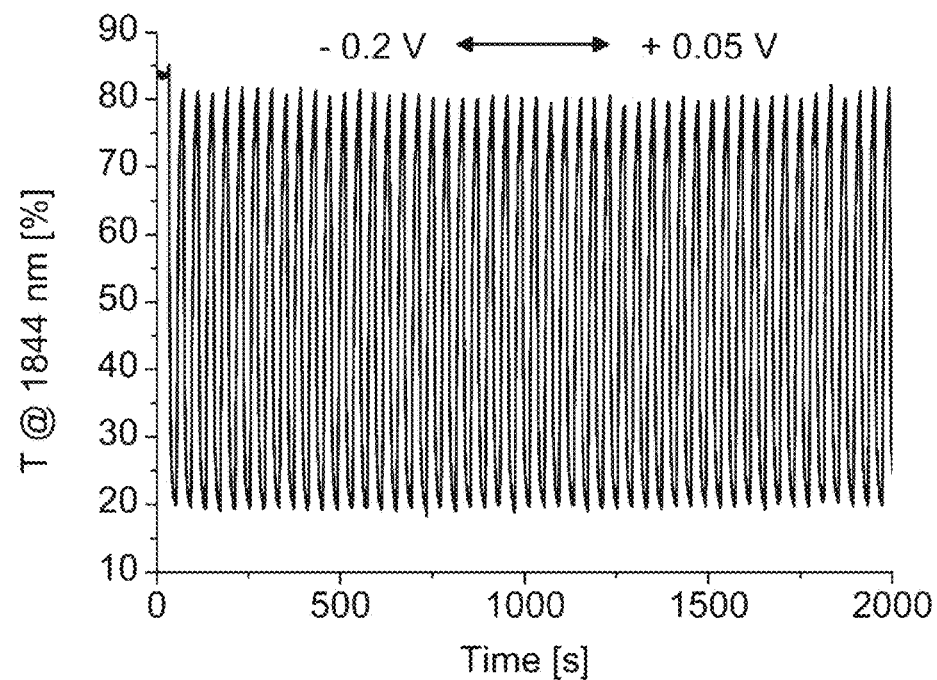
FIG. 38 is a graph showing the repetition characteristics of the light transmittance change at 1,844 nm of a poly($Ru_2Zn$)$_{70}$ film due to the on/off of voltage.

FIG. 38 is a graph showing the repetition characteristics of the light transmittance change at 1,844 nm of the poly(Ru$_2$Zn)$_{70}$ film due to the on/off of voltage.

The result showed that the coloration efficiency η=337 (cm$^2$/C), and ΔT>60%.

It should be noted that the coloration efficiency η is defined by the following equation (1). The coloration efficiency η is an index indicating the extent of area in which the absorbance can be varied. Here, ΔOD represents a change in optical density, Q$_d$ represents a change in the injected/ejected electrons, Tb is (81.5), and Tc is (19.5).

[Equation 1]

$$\eta = \frac{\Delta OD}{Q_d} = \log\frac{Tb}{Tc} \bigg/ Q_d \quad (1)$$

Figure 43A:
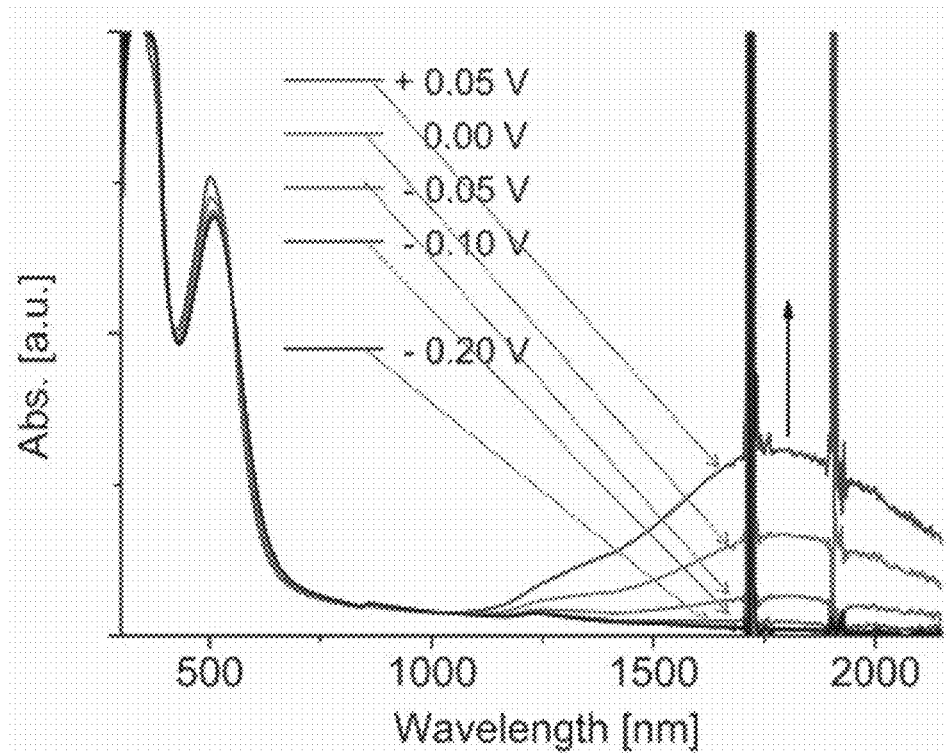
FIG. 43A is a graph showing the applied voltage dependence of the ultraviolet and visible absorption spectrum of an organic/multimetallic hybrid polymer (poly($Ru_2Zn$)$_{70}$) film, when the applied voltage was changed from −0.20 V to 0.05 V in a stepwise manner.

FIG. 43A is a graph showing the applied voltage dependence of the ultraviolet/visible/near infrared absorption spectrum of the film of the branched organic/multimetallic hybrid polymer (poly(Ru$_2$Zn)$_{70}$), when the applied voltage was changed from −0.20 V to 0.05 V in a stepwise manner.

Figure 43B:
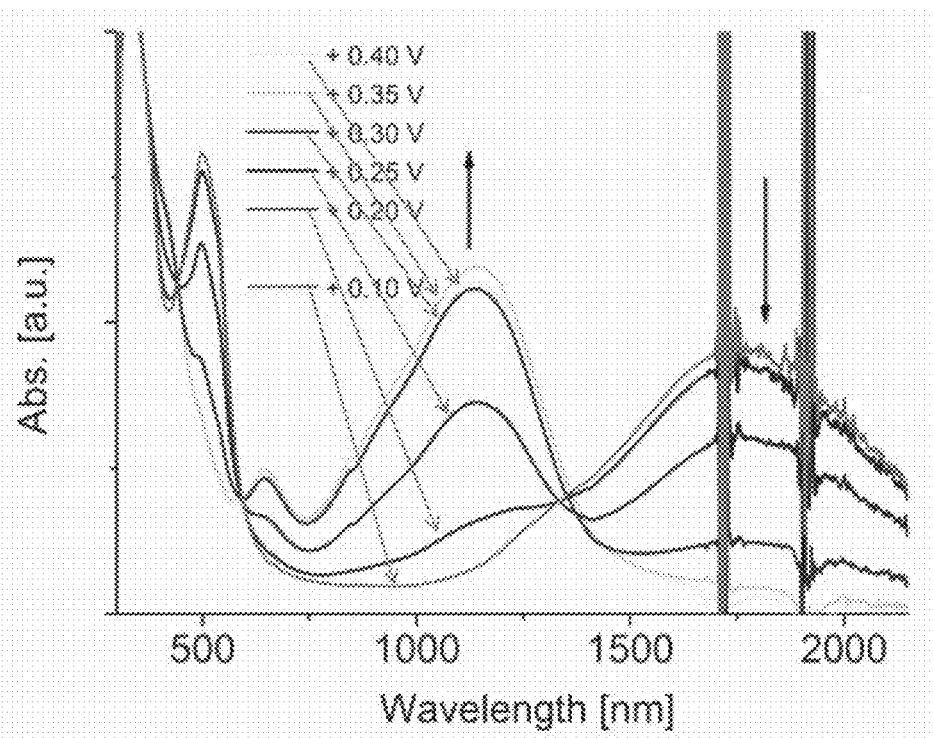
FIG. 43B is a graph showing the applied voltage dependence of the ultraviolet and visible absorption spectrum of an organic/multimetallic hybrid polymer (poly($Ru_2Zn$)$_{70}$) film, when the applied voltage was changed from 0.10 V to 0.40 V in a stepwise manner.

FIG. 43B is a graph showing the applied voltage dependence of the ultraviolet/visible/near infrared absorption spectrum of the film of the branched organic/multimetallic hybrid polymer (poly(Ru$_2$Zn)$_{70}$), when the applied voltage was changed from 0.10 V to 0.40 V in a stepwise manner.

Figure 44A:
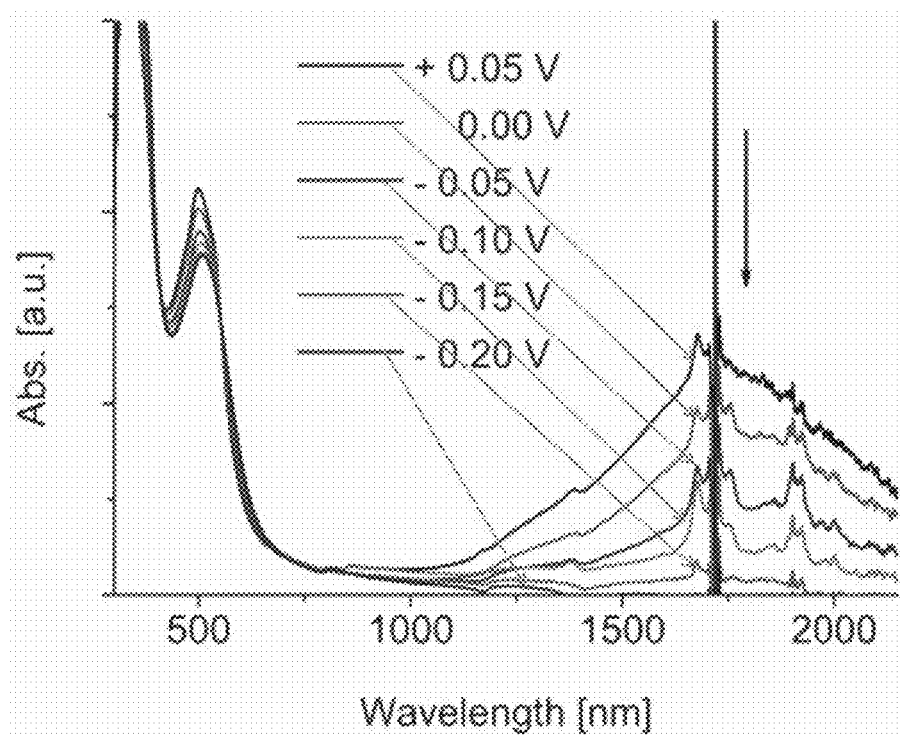
FIG. 44A is a graph showing the applied voltage dependence of the ultraviolet and visible absorption spectrum of an organic/multimetallic hybrid polymer (poly($Ru_2Zn$)$_{70}$) film, when the applied voltage was changed from 0.05 V to −0.20 V in a stepwise manner.

FIG. 44A is a graph showing the applied voltage dependence of the ultraviolet/visible/near infrared absorption spectrum of the film of the branched organic/multimetallic hybrid polymer (poly(Ru$_2$Zn)$_{70}$), when the applied voltage was changed from 0.05 V to −0.20 V in a stepwise manner.

Figure 44B:
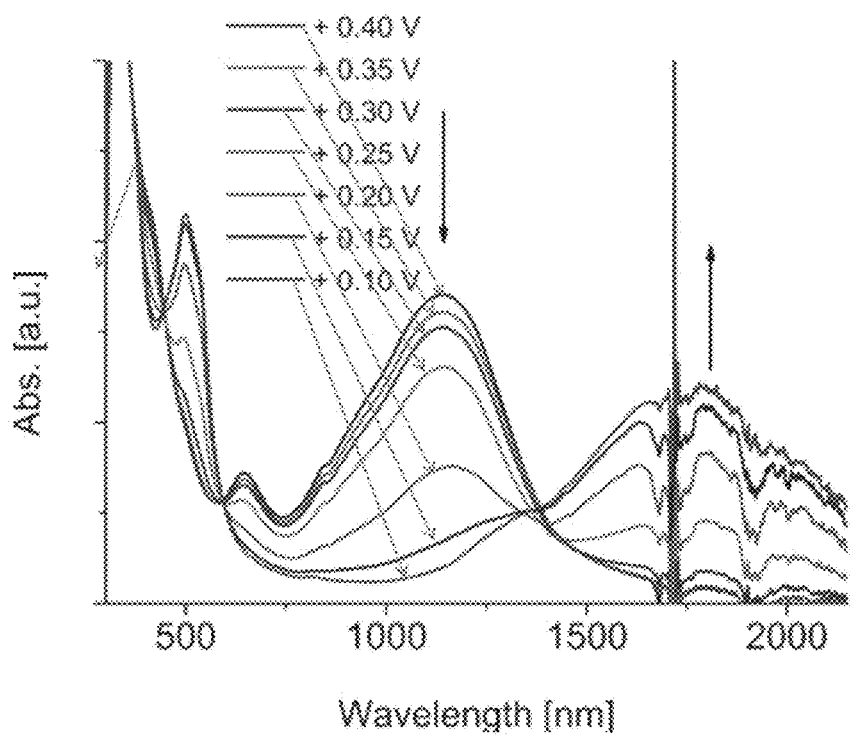
FIG. 44B is a graph showing the applied voltage dependence of the ultraviolet and visible absorption spectrum of an organic/multimetallic hybrid polymer (poly($Ru_2Zn$)$_{70}$) film, when the applied voltage was changed from 0.40 V to 0.10 V in a stepwise manner.

FIG. 44B is a graph showing the applied voltage dependence of the ultraviolet/visible/near infrared absorption spectrum of the film of the branched organic/multimetallic hybrid polymer (poly(Ru$_2$Zn)$_{70}$), when the applied voltage was changed from 0.40 V to 0.10 V in a stepwise manner.

Table 1 shows electrochemical properties of the organic/multimetallic hybrid polymer (poly(Ru$_2$Zn)$_{70}$) film in a 0.1 M acetonitrile solution of LiClO$_4$.

TABLE 1

| Sample | T$_{bleached}$ [%][a] | T$_{colored}$ [%][a] | ΔT [%][a] | t$_{coloring}$ [S][b] | t$_{bleaching}$ [S][b] | Charge/Discharge [mC][c] | η [cm$^2$/C][d] |
|---|---|---|---|---|---|---|---|
| poly(Ru$_2$Zn)$_{70}$ (at 1844 nm) | 81.5 | 19.5 | 62.0 | 20 | 20 | 3.7/1.8 | 272 |
| poly(Ru$_2$Zn)$_{70}$ (at 1174 nm) | 75.3 | 6.1 | 69.2 | 15 | 15 | 8.0/6.4 | 337 |

[a]The transmittances (T$_{bleached}$ and T$_{colored}$) of the NIR absorption at 1844 and 1174 nm in the bleached and colored states of the polymer film coated on an ITO glass were measured by in-situ UV/vis/NIR spectroscopy between −0.02 and +0.05, and +0.05 and +0.40 V vs. Ag/Ag$^+$ with a interval time of 20 s and 15 s, respectively (electrolyte: 0.1M LiClO$_4$/CH$_3$CN the ITO working area: 0.8 × 2.5 cm$^2$). The difference (ΔT) was calculated from T$_{bleached}$ and T$_{colored}$.
[b]The times for coloring and bleaching (t$_{coloring}$ and t$_{bleaching}$) were defined as the time taken 95% of ΔT to change.
[c]The charge/discharge values were the integration of the coulomb number in the current response during the redox.
[d]The coloration efficiency(η) was defined as the relationship between electron charge used and the change of ΔT.

Then, by repeatedly applying voltages of 0.05 V and 0.4 V alternately at 5 second intervals, 10 second intervals and 15 second intervals to the film of the branched organic/multimetallic hybrid polymer (poly(Ru$_2$Zn)$_{70}$), a change in the light transmittance at 1,174 nm was observed.

Figure 39:
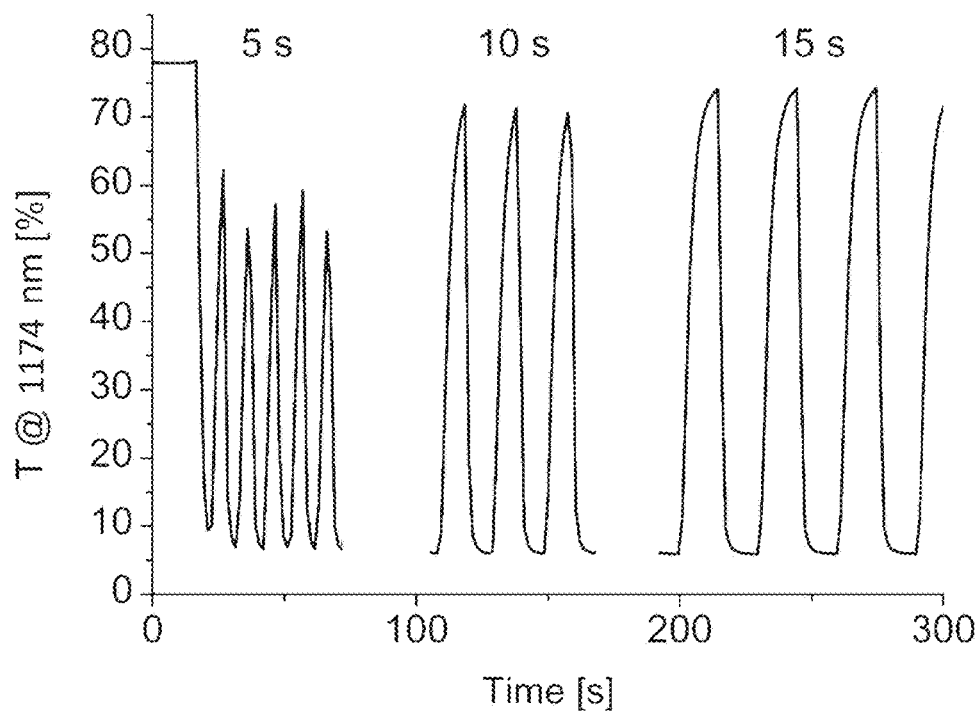
FIG. 39 is a graph showing the application interval dependence of the light transmittance change at 1,174 nm of a poly($Ru_2Zn$)$_{70}$ film due to the on/off of voltage.

FIG. 39 is a graph showing the applied voltage dependence of the light transmittance change at 1,174 nm of the poly(Ru$_2$Zn)$_{70}$ film due to the on/off of voltage.

Then, by repeatedly applying voltages of 0.05 V and 0.4 V alternately 50 times at 15 second intervals to the film of the branched organic/multimetallic hybrid polymer (poly(Ru$_2$Zn)$_{70}$), a change in the light transmittance at 1,174 nm was observed.

Figure 40:
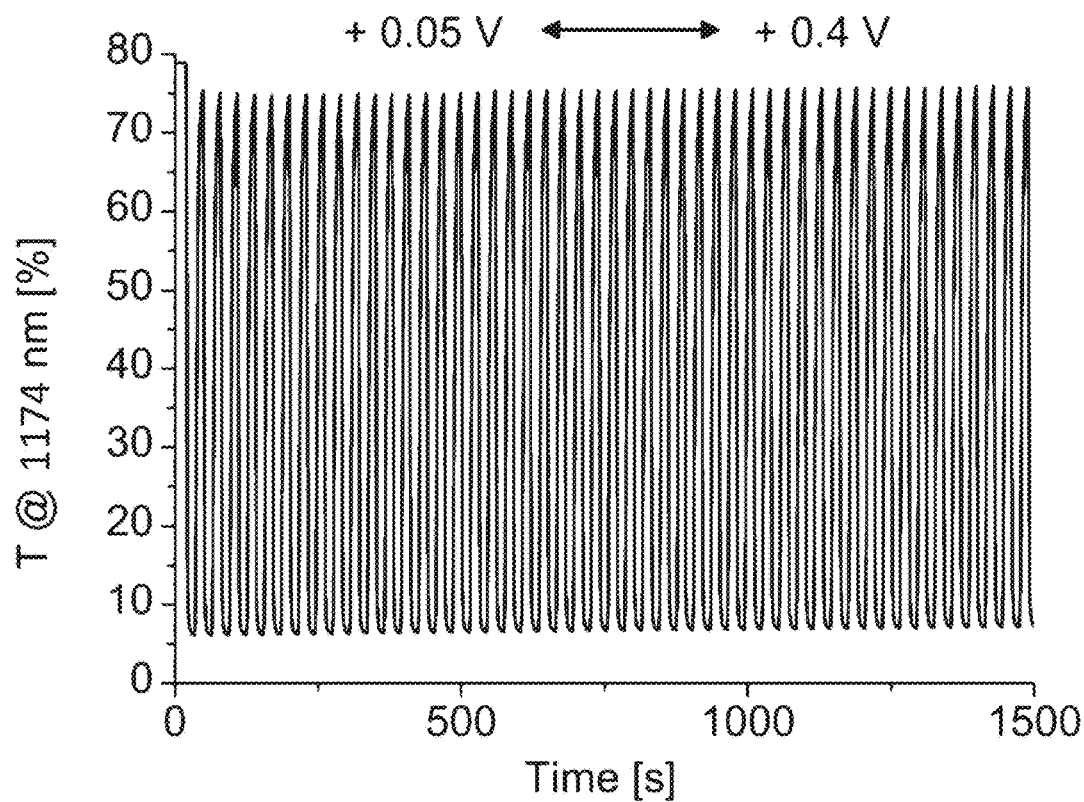
FIG. 40 is a graph showing the repetition characteristics of the light transmittance change at 1,174 nm of a poly($Ru_2Zn$)$_{70}$ film due to the on/off of voltage.

FIG. 40 is a graph showing the repetition characteristics of the light transmittance change at 1,174 nm of the poly(Ru$_2$Zn)$_{70}$ film due to the on/off of voltage.

The result showed that the coloration efficiency η=272 (cm$^2$/C), and ΔT>70%.

As described above, the change in the light transmittance was fast, which was highly reproducible.

Figure 41:
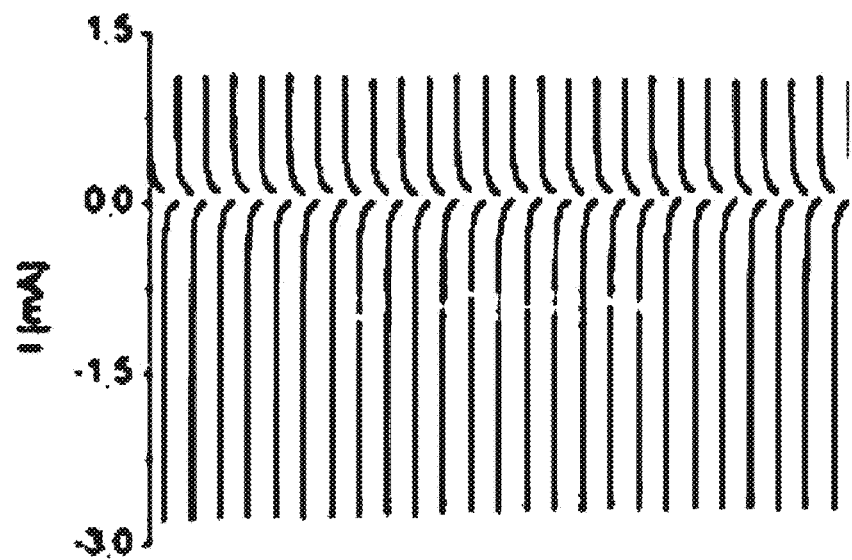
FIG. 41 is a graph showing the change in the current value of a poly($Ru_2Zn$)$_{70}$ film due to the on/off of voltage by the change in the optical absorption at 1,844 nm.

FIG. 41 is a graph showing the change in the current value of the poly(Ru$_2$Zn)$_{70}$ film due to the on/off of voltage by the change in the optical absorption at 1,844 nm.

Figure 42:
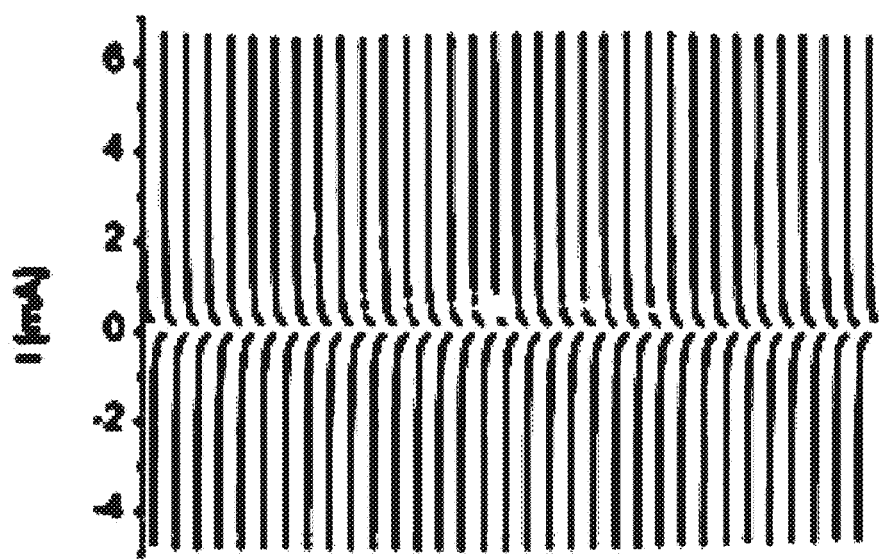
FIG. 42 is a graph showing the change in the current value of a poly($Ru_2Zn$)$_{70}$ film due to the on/off of voltage by the change in the optical absorption at 1,174 nm.

FIG. 42 is a graph showing the change in the current value of the poly(Ru$_2$Zn)$_{70}$ film due to the on/off of voltage by the change in the optical absorption at 1,174 nm.

INDUSTRIAL APPLICABILITY

An organic/heterometallic hybrid polymer, a method for producing the same, and an organic/heterometallic hybrid polymer film according to the present invention exhibit electrochromic properties and relate to a linear and stable organic/heterometallic hybrid polymer. In particular, it is possible to freely convert the optical absorption spectrum from the visible light region to the near infrared light region. Therefore, they can be used as a near infrared light-blocking electrochromic window or a near infrared light shutter, and is industrially applicable in the optical communication industry, optical device industry, window industry, and the like.

The organic/multimetallic hybrid polymer of the present invention is a newly synthesized compound, which is an organic/multimetallic hybrid polymer constituted of an organometal ligand obtained by linking two Ru(dppe)$_2$, exhibiting electrochromic properties in the infrared light region, and highly stable to repetitive oxidation-reduction of metals. In particular, it can be used as an optical communication device capable of blocking light by switching at two wavelengths of 1,310 nm and 1,550 nm that are used in optical communication. For this reason, it is industrially applicable in the optical communication industry, optical device indus-

REFERENCE SIGNS LIST

10: Organometal complex; 11A, 11B: Ligand; 13: Connector; 13: Porous film; 20: Organic/heterometallic hybrid polymer; 20OX: Oxidized organic/heterometallic hybrid polymer; 1': Linear organic/multimetallic hybrid polymer film; 2': Branched organic/multimetallic hybrid polymer film; 5': Linear organic/multimetallic hybrid polymer; 6': Branched organic/multimetallic hybrid polymer; 11'A, 11'B, 11'C: Ligand; 13': Connector; 15': Branch element (triphenylbenzene); 21': Organometal ligand; 31': Linear portion; 41': Branched portion (branched compound); 50': Glass substrate; 51': Transparent conductive film; M': Transition metal.

The invention claimed is:

1. An organic/heterometallic hybrid polymer comprising a plurality of organometal complexes and a plurality of transition metals,
wherein said plurality of organometal complexes are linked in a linear manner by sandwiching each of said plurality of transition metals therebetween,
said organometal complexes include two ligands each having a terpyridyl group and one connector having Ru(dppe)$_2$ and two ethynylene groups, and the two ligands are linked by the connector, so that a nitrogen atom at position 1' of said terpyridyl group is directed toward a terminal side of a molecule of said organometal complex, and
the terpyridyl groups of at least two different organometal complexes of said plurality of organometal complexes are bound to one of said transition metals through a coordinate bond, thereby linking said plurality of organometal complexes while sandwiching said plurality of transition metals alternately therebetween.

2. The organic/heterometallic hybrid polymer according to claim 1, wherein said transition metal is any one of Ru, Fe or Zn.

3. The organic/heterometallic hybrid polymer according to claim 1, wherein a molecular weight $M_W$ is at least $10.5 \times 10^4$ and not more than $29.2 \times 10^4$.

4. An organic/heterometallic hybrid polymer film comprising the organic/heterometallic hybrid polymer according to claim 1.

5. The organic/heterometallic hybrid polymer film according to claim 4, wherein a film thickness is at least 100 nm and not more than 1 mm.

6. The organic/heterometallic hybrid polymer film according to claim 4, wherein a transition metal contained in said organic/heterometallic hybrid polymer is either Fe or Zn.

7. An organic/multimetallic hybrid polymer comprising a plurality of organometal ligands and a plurality of transition metals,
wherein a linear portion in which said plurality of organometal ligands are linked in a linear manner by sandwiching each of said plurality of transition metals therebetween is included,
said organometal ligand is formed by linking two ligands to one connector,
said connector is formed with a benzene ring at the center by linking two Ru(dppe)$_2$ via two ethynylene groups bonded to the benzene ring, while connecting two phenyl groups to said two Ru(dppe)$_2$ via other two ethynylene groups,
said ligands are terpyridyl groups and are formed by being connected respectively to said two phenyl groups of said connector, and
said terpyridyl groups of at least two different organometal ligands of said plurality of organometal ligands are bound to one of said transition metals through a coordinate bond, thereby linking said plurality of organometal ligands while alternately sandwiching said plurality of transition metals therebetween.

8. The organic/multimetallic hybrid polymer according to claim 7, wherein said transition metal is Fe, Zn, Co or Ru.

9. The organic/multimetallic hybrid polymer according to claim 7 which is linear.

10. The organic/multimetallic hybrid polymer according to claim 7 which is branched.

11. The organic/multimetallic hybrid polymer according to claim 10 comprising a branched portion composed of 1,3,5-Tris[4-(2,2':6',2''-terpyridin-4'-yl)phenyl]benzene.

12. The organic/multimetallic hybrid polymer according to claim 10, wherein a content of said branched portion is at least 10 molar parts and not more than 30 molar parts, relative to the total number of moles of linear portions and branched portions constituting the organic/multimetallic hybrid polymer.

13. An organic/multimetallic hybrid polymer film comprising the organic/multimetallic hybrid polymer according to claim 7.

14. The organic/multimetallic hybrid polymer film according to claim 13, wherein a film thickness is at least 100 nm and not more than 1 mm.

15. A method of producing an organic/heterometallic hybrid polymer, the method comprising:
a step of synthesizing an organometal complex having Ru(dppe)$_2$ and a terminal terpyridyl group by reacting a terpyridine compound having an ethynyl group and a terpyridyl group with a compound containing Ru(dppe)$_2$ in an organic solvent; and
a step of synthesizing the organic/heterometallic hybrid polymer by reacting said organic metal complex and a transition metal compound in an organic solvent.

16. The method of producing an organic/heterometallic hybrid polymer according to claim 15, wherein 1.0 molar equivalent or more of the transition metal compound is reacted with respect to said organometal complex.

17. The method of producing an organic/heterometallic hybrid polymer according to claim 15, wherein said transition metal compound is any one of RuCl$_2$, Fe(BF$_4$)$_2$, or Zn(NTf$_2$)$_2$.

18. The method of producing an organic/heterometallic hybrid polymer according to claim 15, wherein a reaction time of said organic metal complex and said transition metal compound is equal to or more than 12 hours.

19. A method of synthesizing an organic/multimetallic hybrid polymer, the method comprising:
a step of synthesizing a binuclear organometallic site comprising two Ru(dppe)$_2$ by reacting 1 molar equivalent of diethynylbenzene and 2 molar equivalents of Ru(dppe)$_2$Cl(OTf) in an organic solvent;
a step of synthesizing an organometal ligand having a terpyridyl group at the terminal and two Ru(dppe)$_2$ by reacting 2 molar equivalents of a terpyridine compound having an ethynyl group and a terpyridyl group with one molar equivalent of a binuclear organometallic site in an organic solvent; and a step of synthesizing a linear organic/multimetallic hybrid polymer by reacting said organometal ligand and a transition metal compound in an organic solvent.

20. The method of synthesizing an organic/multimetallic hybrid polymer according to claim 19, wherein a branched organic/multimetallic hybrid polymer is synthesized by reacting said linear organic/multimetallic hybrid polymer, a branched compound branched into three or more directions with a branch element at the center and having a ligand at a branched molecule end, and a transition metal compound.

21. The method of synthesizing an organic/multimetallic hybrid polymer according to claim 20, wherein said branched compound is 1,3,5-Tris[4-(2,2':6',2''-terpyridin-4'-yl)phenyl]benzene.

22. The method of synthesizing an organic/multimetallic hybrid polymer according to claim 20, wherein a mixing amount of said branched compound is at least 10 molar parts and not more than 30 molar parts, relative to the combined total of 100 molar parts of linear portions constituting the linear organic/multimetallic hybrid polymer.

23. The method of synthesizing an organic/multimetallic hybrid polymer according to claim 19, wherein 1.0 molar equivalent or more of the transition metal compound is reacted with respect to said organometal ligand.

24. The method of synthesizing an organic/multimetallic hybrid polymer according to claim 19, wherein said transition metal compound is $Fe(BF_4)_2$ or $Zn(NTf_2)_2$.

25. The method of synthesizing an organic/multimetallic hybrid polymer according to claim 19, wherein a reaction time of said organometal ligand and said transition metal compound is equal to or more than 6 hours.

* * * * *